(12) United States Patent
Zhang et al.

(10) Patent No.: US 11,193,947 B2
(45) Date of Patent: Dec. 7, 2021

(54) B-TYPE NATRIURETIC PEPTIDE PROTEOLYTIC ASSAY FOR CARDIOVASCULAR DISEASE RISK ASSESSMENT

(71) Applicant: Cedars-Sinai Medical Center, Los Angeles, CA (US)

(72) Inventors: Shenyan Zhang, Beijing (CN); Koen Raedschelders, Venice, CA (US); Jennifer Van Eyk, Los Angeles, CA (US)

(73) Assignee: CEDARS-SINAI MEDICAL CENTER, Los Angeles, CA (US)

( * ) Notice: Subject to any disclaimer, the term of this patent is extended or adjusted under 35 U.S.C. 154(b) by 62 days.

(21) Appl. No.: 16/152,336

(22) Filed: Oct. 4, 2018

(65) Prior Publication Data

US 2019/0025333 A1    Jan. 24, 2019

Related U.S. Application Data

(63) Continuation-in-part of application No. PCT/US2017/035544, filed on Jun. 1, 2017.
(Continued)

(51) Int. Cl.
    *G01N 33/74*    (2006.01)
(52) U.S. Cl.
    CPC ......... *G01N 33/74* (2013.01); *G01N 2570/00* (2013.01); *G01N 2800/32* (2013.01); *G01N 2800/50* (2013.01)
(58) Field of Classification Search
    None
    See application file for complete search history.

(56) References Cited

U.S. PATENT DOCUMENTS

| 6,124,430 A | 9/2000 | Mischak et al. |
| 2005/0148024 A1* | 7/2005 | Buechler ............... A61K 38/05 |
| | | 435/7.1 |

(Continued)

FOREIGN PATENT DOCUMENTS

| EP | 3464339 A1 | 4/2019 |
| WO | 2008/030901 A2 | 3/2008 |
| WO | 2017210488 A1 | 12/2017 |

OTHER PUBLICATIONS

Tamm, Natalia N; et al; "Novel Immunoassay for Quantification of Brain Natriuretic Peptide and Its Precursor in Human Blood" Clinical Chemistry, 54, 1511-1518, 2008 (Year: 2008).*

(Continued)

*Primary Examiner* — David W Berke-Schlessel
(74) *Attorney, Agent, or Firm* — Nixon Peabody LLP

(57) ABSTRACT

Described herein are methods for assessing the risk of cardiovascular disease in a subject in need thereof by detecting the presence of one or more cleavage products of the one or more natriuretic peptides over a period of time, wherein the presence of one or more cleavage products is indicative of an increased risk of the subject developing cardiovascular disease. Provided herein are compositions and kits comprising a non-natural natriuretic peptide comprising one or more D-amino acids. Also provided herein are methods of diagnosing a subject for a disease and treating the subject for the disease, wherein the method comprises the use of a non-natural natriuretic peptide comprising one or more D-amino acids.

24 Claims, 33 Drawing Sheets

Specification includes a Sequence Listing.

CE separations are based on the specificity of molecular electrophoretic mobility.

$$\mu_{ep} = \frac{q}{6\pi r \eta}$$

molecular charge
molecular size
buffer viscosity

Sheathless ESI    MS inlet

Sample plug
Spacer
HIGH VOLTAGE

'Inlet'
(separation capillary)

'Outlet'
(conductive capillary)

CESI 8000 Plus High Performance Separation-ESI Module
(SCIEX Separation)

Q Exactive+
(Thermo Scientific)

Related U.S. Application Data

(60) Provisional application No. 62/345,595, filed on Jun. 3, 2016, provisional application No. 62/568,171, filed on Oct. 4, 2017.

(56) References Cited

U.S. PATENT DOCUMENTS

| | | |
|---|---|---|
| 2005/0244902 A1 | 11/2005 | Gotze et al. |
| 2011/0104813 A1 | 5/2011 | Amann-Zalan et al. |
| 2011/0256169 A1 | 10/2011 | Kas et al. |

OTHER PUBLICATIONS

Apple, Fred S; et al; "Quality Specifications for B-Type Natriuretic Peptide Assays" Clinical Chemistry, 51, 486-493, 2005 (Year: 2005).*

Zhang, Shenyan; et al; "Profiling B-Type Natriuretic Peptide Cleavage Peptidoforms in Human Plasma by Capillary Electrophoresis with Electrospray Ionization Mass Spectrometry" Journal of Proteome Research, 16, 4515-4522, 2017 (Year: 2017).*

EP 17807518.0 Extended European Search Report dated Nov. 26, 2019, 10 pages.

Foo et al., Circulating Fragments of N-Terminal Pro-B Type Natriuretic Peptides in Plasma of Heart Failure Patients, Clinical Chemistry, 2013, vol. 59(10), pp. 1523-1531.

Zhang et al., Association Between Serum Corin Levels and Risk of Acute Myocardial Infarction, Clinica Chimica Acta, 2016, vol. 452, pp. 134-137.

International Preliminary Report on Patentability for PCT/US2017/035544 dated Dec. 13, 2018, 8 pages.

International Search Report and Written Opinion for PCT/US2017/035544 dated Aug. 10, 2017, 10 pages.

Belenky et al., The effect of class-specific protease inhibitors on the stabilizaiton of B-type natriuretic peptide in human plasma, Clin. Chim. Acta, 2004, vol. 340 (1-2), pp. 163-172.

Buckley et al., Cardiac peptide stability, aprotinin and room temperature: importance for assessing cardiac function in clinical practice, Clin. Sci. (Lond), 1999, vol. 97 (6), pp. 689-695.

Cai et al., Top-down Proteomics: Technology Advancements and Applications to Heart Diseases, Expert Rev. Proteomics, 2016, vol. 13(8), pp. 717-730.

Chappell et al., Development and validation of an IA-LC/MS method to quantitate active and total B-type natriuretic peptide in human plasma, Bioanalysis, 2016, vol. 8 (22), pp. 2341-2349.

Clerico et al., Diagnostic accuracy and prognostic relevance of the measurement of cardiac natriuretic peptides: a review, Clin. Chem., 2004, vol. 50 (1), pp. 33-50.

Cummins et al., Radioimmunoassay of Human Cardiac Tropomyosin in Acute Myocardial Infarction, Clinical Science, 1981, vol. 60(3), pp. 251-259.

Fert-Bober et al., Citrullination of myofilament proteins in heart failure, Cardiovascular Research, 2015, vol. 108(2), pp. 232-242.

Hall, C., Essential biochemistry and physiology of (NT-pro)BNP, Eur. J. Heart Fail., 2004, vol. 6 (3), pp. 257-260.

Hirokawa et al., High-sensitive capillary zone electrophoresis analysis by electrokinetic injection with transient isotachophoretic preconcentration: electrokinetic supercharging, Electrophoresis, 2003, vol. 24 (3), pp. 498-504.

Huntley et al., ProBNP1-108 Processing and Degradation in Human Heart Failure, Circ. Heart Fail., 2015, vol. 8 (1), pp. 89-97.

Kirk et al., Cardiac resynchronization sensitizes the sarcomere to calcium by reactivating GSK-3B, J. Clin. Invest., 2014, vol. 124(1), pp. 129-139.

Kooij et al., Identification of Cardiac Myofilament Protein Isoforms Using Multiple Mass Spectrometry Based Approaches, Proteomics Clin. Appl., 2014, vol. 8(0), pp. 578-589.

Kuehnbaum et al., Multisegment injection-capillary electrophoresis-mass spectrometry: a high-throughput platform for metabolomics with high data fidelity, Anal. Chem., 2013, vol. 85 (22), pp. 10664-10669.

Lee et al., Phosphodiesterase 9A controls nitric-oxide-independent cGMP and hypertrophic heart disease, Nature, 2015, vol. 519, pp. 472-476.

Maisel, B-type natriuretic peptide levels: diagnostic and prognostic in congestive heart failure: what's next?, Circulation, 2002, vol. 105(20), pp. 2328-2331.

Murray et al., Alternative projections of mortality and disability by cause 1990-2020: Global Burden of Disease Study, Lancet, 1997, vol. 349 (9064), pp. 1498-1504.

Neuberger et al., Screening of Small Intact Proteins by Capillary Electrophoresis Electrospray Ionizatin-Mass Spectrometry (CE-ESI-MS), Methods Mol. Biol., 2016, vol. 1466, pp. 43-56.

Niederkofler et al., Detection of endogenous B-type natriuretic peptide at very low concentrations in patients with heart failure, Circ. Heart Fail., 2008, vol. 1 (4), pp. 258-264.

Norman et al., Degradation of brain natriuretic peptide by neutral endopeptidase: species specific sites of proteolysis determined by mass spectrometry, Biochem. Biophys. Res. Commun., 1991, vol. 175 (1), pp. 22-30.

Oefner et al., Structural analysis of neprilysin with various specific and potent inhibitors., Acta Crystallogr. D Biol. Crystallogr., 2004, vol. 60 (Pt 2), pp. 392-396.

Oefner et al., Structural studies of a bifunctional inhibitor of neprilysin and DPP-IV., Acta Crystallogr. D Biol. Crystallogr., 2007, vol. 63 (Pt 9), pp. 975-981.

Peng et al., Top-down Targeted Proteomics for Deep Sequencing of Tropomyosin Isoforms, J.Proteome Res., 2013, vol. 12(1), pp. 187-198.

Purcell et al., Functional analysis of human cardiac troponin by the in vitro motility assay: conmparison of adult, foetal and failing hearts, Cardiovascular Research, 1999, vol. 43, pp. 884-891.

Raedschelders et al., Development of a quantitative MS-based assay for intact BNP and its proteolytic variants: Early impressions with LC and CE from "high flow" to "No-flow", Poster Presentation (#50) Feb. 22, 2016, The Association for Mass Spectrometry: Applications to the Clinical Lab (MSACL) 2016 US, The 8th Annual International Conference, Feb. 21-25, 2016, Palm Springs, California, 1 page.

Rajan et al., Molecular and Functional Characterization of a Novel Cardiac-Specific Human Tropomyosin Isoform, 2010, vol. 121, pp. 410-418.

Shen et al., Structures of human insulin-degrading enzyme reveal a new substrate recognition mechanism., Nature, 2006, vol. 443 (7113), pp. 870-874.

Simons et al., Evaluation of natriuretic peptide recommendations in heart failure clinical practice guidelines, Clin. Biochem., 2016, vol. 49 (1-2), pp. 8-15.

Sun et al., Fast top-down intact protein characterization with capillary zone electrophoresis-electrospray ionization tandem mass spectrometry, Anal. Chem., 2013, vol. 85 (12), pp. 5989-5995.

Suzuki et al., Editor's Choice—Biomarkers of acute cardiovascular and pulmonary diseases, Eur. Heart J. Acute Cardiovasc. Care, 2016, vol. 5 (5), pp. 416-433.

Takimoto et al., Chronic inhibition of cyclic GMP phosphodiesterase 5A prevents and reverses cardiac hypertrophy, Nat. Med., 2005, vol. 11 (2), pp. 214-222.

Van Eyk, Analysis of the Natiuretic Peptides: a interesting twist for peptidoform profiling, Presentation, 2017 Global CESI-MS Symposium, Boston, MA, Oct. 5-6, 2017, 27 pages.

Volpe et al., Natriuretic peptides in cardiovascular diseases:current use and perspectives, European Heart Journal, 2014, vol. 35, pp. 419-425.

Zhang et al., Multiple Reaction Monitoring to Identify Site-Specific Troponin I Phosphorylated Residues in the Failing Human Heart, Circulation, 2012, vol. 126(15), pp. 1828-1837.

Zhang et al., Protein analysis by shotgun/buttom-up proteomics, Chem. Rev. 2013, vol. 113(4), pp. 2343-2394.

Zhang et al., Analysis of Native Proteolytic BNP Variants: Simultaneous Separation of Multiple Samples using Capillary Electrophoresis—Mass Spectrometry with Multi-Segment Injection, Poster Presentation (TP679) Jun. 7, 2016, 64th American Society for Mass Spectrometry (ASMS) Conference on Mass Spectrometry and Allied Topics, Jun. 5-9, 2016, San Antonio, Texas, 1 page.

(56) References Cited

OTHER PUBLICATIONS

Zhang et al., Profiling B-Type Natriuretic Peptide Cleavage Peptidoforms in Human Plasma by Capillary Electrophoresis with Electrospray Ionizaition Mass Spectrometry, J. Proteome Res., 2017, vol. 16 (12), pp. 4515-4522.
The 8th Annual International Conference of The Association for Mass Spectrometry: Applications to the Clinical Lab (MSACL 2016 US), Progam, Feb. 21-25, 2016, Palm Springs, California, pp. 1-156.
64th American Society for Mass Spectrometry (ASMS) Conference on Mass Spectrometry and Allied Topics, Program, Jun. 5-9, 2016, San Antonio, Texas, pp. 1-266.
2017 Global CESI-MS Symposium, Program, Boston, MA, Oct. 5-6, 2017, 2 pages.

\* cited by examiner

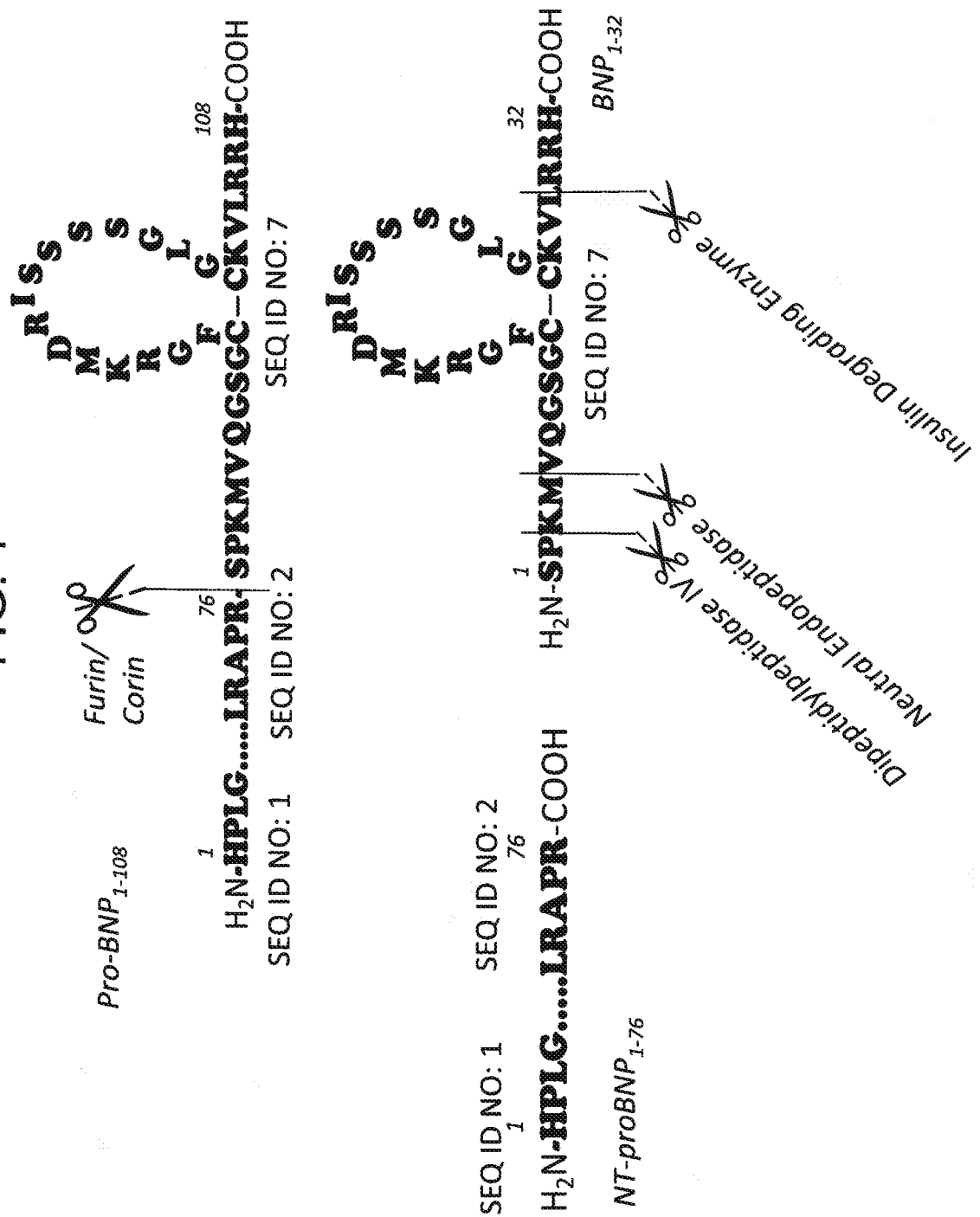

FIG. 2

Quantification of Brain (B-type) Natriuretic Peptide (BNP)

| | SEQ ID NO | amino acids | Localization | Molecular Weight |
|---|---|---|---|---|
| preproBNP | 4 | 1-134 | Cardiomyocyte | *glycosylation dependent* |
| proBNP | 5 | 1-108 | Cardiomyocyte | *glycosylation dependent* |
| NT-proBNP | 6 | 1-76 | Peripheral circulation | *glycosylation dependent* |
| BNP | 7 | 1-32 | Peripheral circulation | 3462 |

MDPQTAPSRALLLLLFLHLAFLGGRSHPLGSPGSAS

DLETSGLQEQRNHLQGKLSELQVEQTSLEPLQESPR

PTGVWKSREVATEGIRGHRKMVLYTLRAPRSPKMVQGS   SEQ ID NO: 4

GCFGRKMDRISSSSGLGCKVLRRH
⌞S-S⌟

*Enshadowed letters signifies known epitopes targeted by detection antibodies*
*Underlined amino acids signify putative O-glycosylation sites*

FIG. 3

- Materials and Methods:
  - Recombinant $BNP_{1-32}$ was purchased from Sigma Alrich (Cat#B5900).
  - Human serum was centrifuged for lipid removal and filtered by 0.22 μm filter tube.
  - $BNP_{1-32}$ at 250ng/μl was spiked into filtered serum prior to CE-MS analysis.

- Capillary electrophoresis-related materials:
  - Beckman CESI 8000 Plus High Performance Separation Module
  - Capillary: Neutral-coated OptiMS Cartridge (SCIEX);
  - Separation Voltage: 30kV.
  - Background electrolyte: 10% acetic acid
  - Separation method detailed in below:

| | Time (min) | Event | Value | Duration | Inlet vial | Outlet vial | Summary |
|---|---|---|---|---|---|---|---|
| 1 | | Rinse - Pressure | 100.0 psi | 3.00 min | BI:C1 | BO:A1 | forward | HCl rinse |
| 2 | | Rinse - Pressure | 100.0 psi | 5.00 min | BI:B1 | BO:A1 | forward | BGE rinse sep cap |
| 3 | | Rinse - Pressure | 75.0 psi | 3.00 min | BI:A1 | BO:A1 | reverse | BGE conductive cap |
| 4 | | Wait | | 0.00 min | BI:D1 | BO:A1 | | water dip |
| 5 | | Inject - Pressure | 2.0 psi | 5.0 sec | SI:A1 | BO:A1 | No override, forward | sample injection |
| 6 | | Inject - Pressure | 5.0 psi | 60.0 sec | SI:B1 | BO:A1 | No override, forward | Spacer injerction |
| 7 | | Wait | | 0.00 min | BI:D1 | BO:A1 | | water dip |
| 8 | | Inject - Pressure | 2.0 psi | 5.0 sec | SI:A1 | BO:A1 | No override, forward | sample injection |
| 9 | | Inject - Pressure | 5.0 psi | 60.0 sec | SI:B1 | BO:A1 | No override, forward | Spacer injerction |
| 10 | | Wait | | 0.00 min | BI:D1 | BO:A1 | | water dip |
| 11 | | Inject - Pressure | 2.0 psi | 5.0 sec | SI:A1 | BO:A1 | No override, forward | sample injection |
| 12 | | Inject - Pressure | 2.0 psi | 60.0 sec | SI:B1 | BO:A1 | No override, forward | Buffer Plug |
| 13 | 0.00 | Separate - Voltage | 30.0 KV | 13.00 min | BI:A1 | BO:A1 | 1.00 Min ramp, normal polarity, forward | |
| 14 | 1.00 | Relay On | | | | | 1:0.17;2:0.17 | MS initiation |
| 15 | 13.00 | Separate - Voltage | 1.0 KV | 5.00 min | BI:A1 | BO:A1 | 5.00 Min ramp, normal polarity, forward | 5min ramp down |
| 16 | 18.00 | End | | | | | | |

- Spray voltage 1.8kV; AGC:3e6; Max IT: 100ms; Scan range:200-1200; default charge: 4; Capillary temp: 50°C
- Full MS1 scan: R=70000; DD-MS2: R=17500
- Data analysis:
  - Tracefinder 3.1 (Thermo)
  - Biopharmfinder 1.0 SP1 (Thermo)

FIG. 4
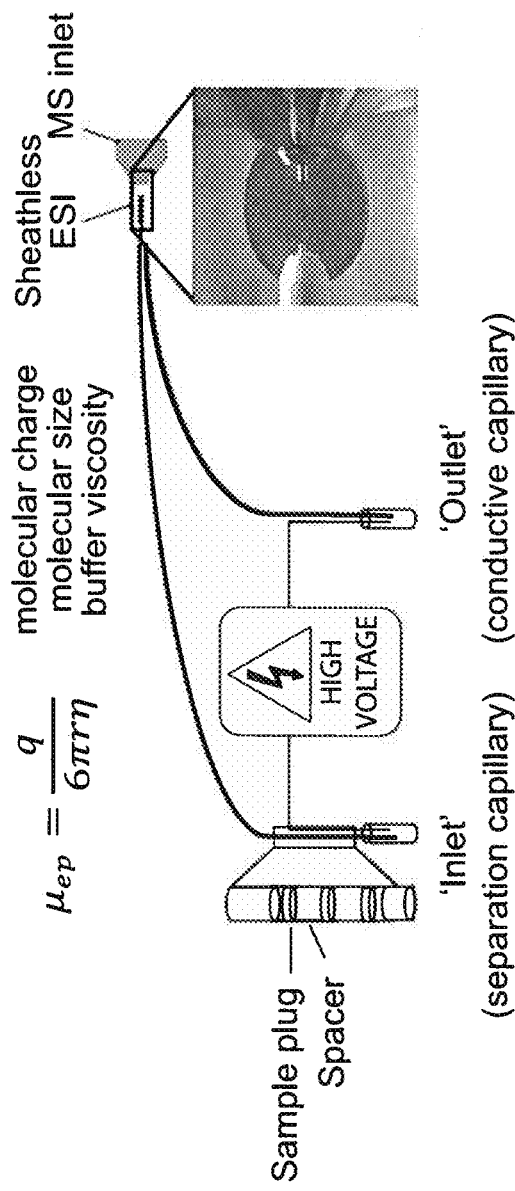
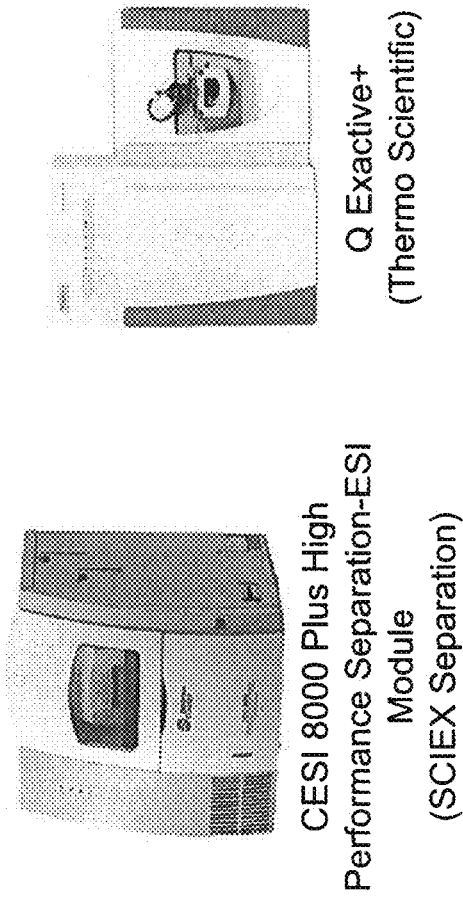

FIG. 8A

| Peak area | MSI | | | | | CV of intra-run | Average of intra-run CV | CV of inter run |
|---|---|---|---|---|---|---|---|---|
| Run | 1 | 2 | 3 | | | | | |
| 1 | 1.37E+08 | 1.01E+08 | 8.44E+07 | | | 25% | | |
| 2 | 1.03E+08 | 6.45E+07 | 5.75E+07 | | | 32% | | |
| 3 | 6.02E+07 | 5.42E+07 | 5.84E+07 | | | 5% | 18% | 35% |
| 4 | 6.75E+07 | 5.82E+07 | 4.64E+07 | | | 18% | | |
| 5 | 5.63E+07 | 6.01E+07 | 5.05E+07 | | | 9% | | |
| CV of inter-run | 41% | 28% | 25% | | | | | |
| Average of inter run CV | 31% | | | | | | | |

FIG. 8B

| Migration time (min) | Run | | | | | CV of inter-run migration time | std of inter run migration time (min) |
|---|---|---|---|---|---|---|---|
| MSI | 1 | 2 | 3 | 4 | 5 | | |
| 1 | 8.43 | 8.36 | 8.37 | 8.37 | 8.41 | 0.36% | 0.03 |
| 2 | 9.09 | 9.04 | 9.04 | 9.02 | 9.09 | 0.35% | 0.03 |
| 3 | 9.73 | 9.7 | 9.69 | 9.67 | 9.74 | 0.30% | 0.03 |

| Concentration of BNP ng/µl | 50 | 100 | 150 | 200 | 250 |
| --- | --- | --- | --- | --- | --- |
| RUN1 | 3.52E+07 | 4.76E+07 | 8.36E+07 | 1.47E+08 | 1.29E+08 |
| RUN2 | 2.45E+07 | 5.70E+07 | 7.72E+07 | 1.22E+08 | 1.45E+08 |
| RUN3 | 1.99E+07 | 5.47E+07 | 6.98E+07 | 9.66E+07 | 1.21E+08 |
| Average of peak area | 2.65E+07 | 5.31E+07 | 7.69E+07 | 1.22E+08 | 1.32E+08 |
| STD of Peak area | 7.86E+06 | 4.93E+06 | 6.88E+06 | 2.54E+07 | 1.22E+07 |
| CV | 30% | 9% | 9% | 21% | 9% |

Analytical requirements
- Specificity
- Reproducibility
- High-throughput
- Turnaround time
- Simple sample preparation
- Presence of intact plasma proteins in the matrix CE - MS Solution CESI 8000 Plus High Performance Separation - ESI Module (SCIEX)

Q Exactive plus (Thermo)

FIG. 22

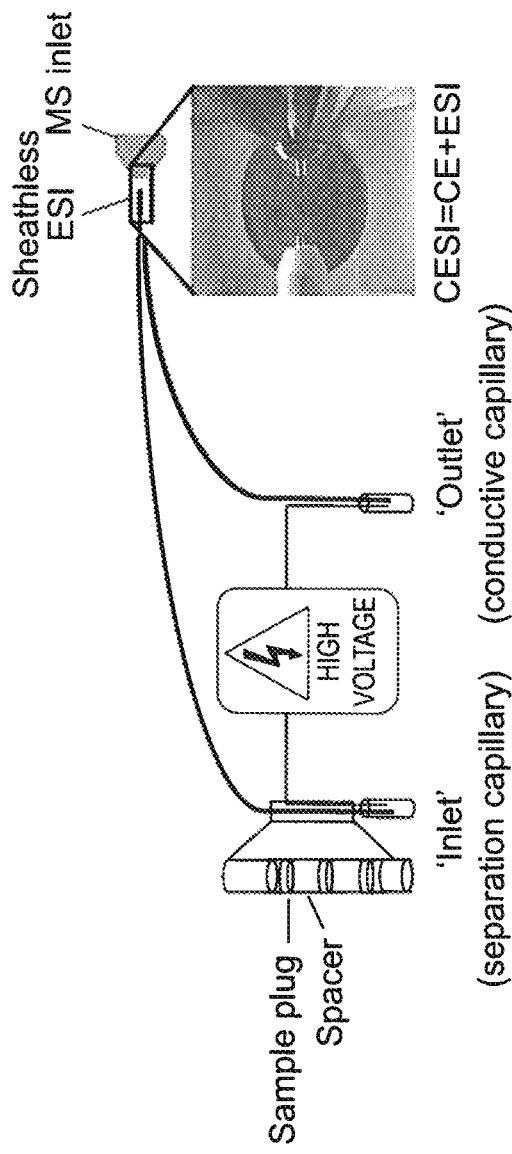

| Protein | Theoretical pI |
|---|---|
| $BNP_{1-32}$ | 12.14 |
| Neutral endopeptidase | 5.54 |
| Dipeptydilpeptidase IV | 5.67 |
| insulin degrading enzyme | 6.16 |

- Neutral coated capillaries are compatible with intact protein analysis from minimally processed plasma
- CE provides High resolution separation
- Electrokinetic injection can selectively inject high pI sample components
- Electrokinetic injection can reduced matrix effect of plasma
- Multisegment injeciton can increase throughput

FIG. 30
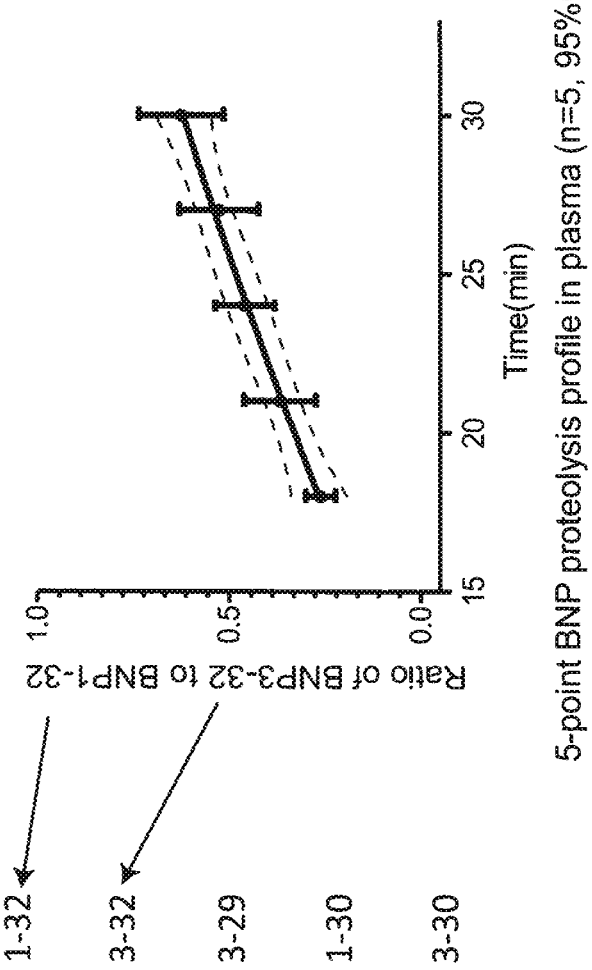
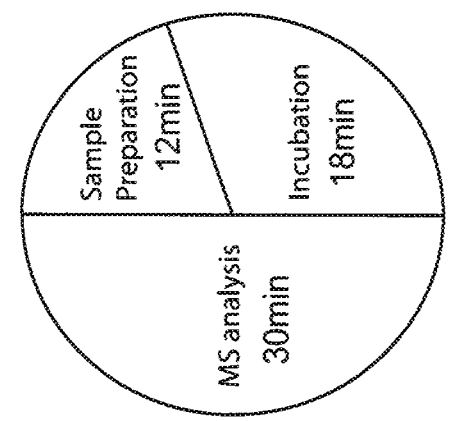
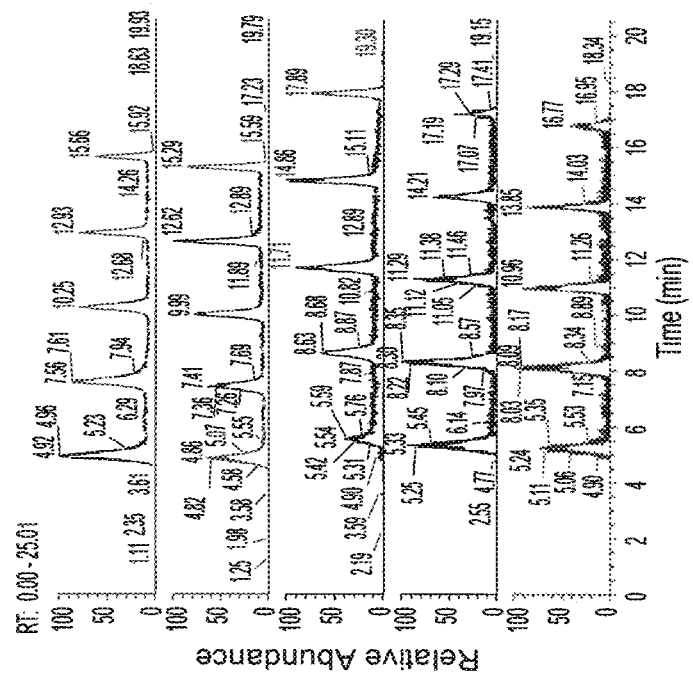

ANP and BNP bind the same receptors but released into the circulate with different cardiac stressors.

- Plasma levels of ANP of healthy individuals is ~20 pg/ml and increases by 10–100-fold with HF.
- Both ANP and NT-proANP have been used as markers for the HF diagnosis.
- ANP levels increases with atrial fibrillation.
- Little is know about ANP proteolytic forms

B-TYPE NATRIURETIC PEPTIDE PROTEOLYTIC ASSAY FOR CARDIOVASCULAR DISEASE RISK ASSESSMENT

CROSS-REFERENCE TO RELATED APPLICATIONS

This application is a continuation-in-part of International Application No. PCT/US2017/035544, filed on Jun. 1, 2017, which designated the U.S., was published under PCT Article 21(2) in English, and claims priority under 35 U.S.C. § 119(e) to U.S. provisional patent application No. 62/345,595, filed on Jun. 3, 2016. This application also claims priority under 35 U.S.C. § 119(e) to U.S. provisional patent application No. 62/568,171 filed on Oct. 4, 2017. The contents of all the related applications cross-referenced herein are herein incorporated by reference in their entirety as though fully set forth.

STATEMENT REGARDING FEDERALLY SPONSORED RESEARCH OR DEVELOPMENT

This invention was made with government support under Grant No. HL112730 awarded by the National Institutes of Health and Grant No. W81XWH-16-1-0592 awarded by the United States Department of Defense. The government has certain rights in the invention.

SEQUENCE LISTING

The instant application contains a Sequence Listing which has been filed electronically in ASCII format and is hereby incorporated by reference in its entirety. Said ASCII copy, created on Oct. 4, 2018 is named 065472-000630US00_SL.txt and is 6,226 bytes in size.

FIELD OF THE INVENTION

Described herein are methods for assessing risk of cardiovascular diseases. Described herein are compositions and methods for diagnosing and/or prognosing disease.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

BNP is a biologically active circulating hormone whose concentration is routinely used in the diagnosis of heart failure. There are two clinical assays NT-proBNP and BNP. NT-proBNP is a large fragment generated from the pre-hormone when BNP 1-32 is cleaved. BNP1-32 has been reported to be further cleaved in plasma (FIG. 1). However, antibody-based methods cannot distinguish those proteolytic variants.

Heart disease continues to persist as a major cause of worldwide mortality, which underscores the urgent need for improved diagnostic and risk stratification tools. B-type Natriuretic Peptide (BNP) is a key biomarker whose quantitative analysis is used to clinically assess heart failure. Brain Natriuretic Peptide (BNP) is a biologically active circulating hormone. BNP and cleavage peptidoforms derived therefrom are key biomarkers whose concentrations are routinely used in the diagnosis of heart failure.

Physiological plasma BNP levels reflect a state of dynamic equilibrium, in which the prohormone proBNP is cleaved and secreted by cardiomyocytes, and actively processed and degraded in plasma by at least 3 known peptidases, neutral endopeptidase (NEP), dipeptidylpeptidase IV (DPPIV), and insulin degrading enzyme (IDE) potentially in conjunction with additional putative enzymes. While plasma sampling eliminates the input of newly secreted BNP, the catabolic and processing steps that occur in plasma remain intact. The length and conditions of sample storage upstream of BNP analysis is therefore an important variable. Nevertheless, the extent to which BNP processing occurs in plasma as well as its relationship with heart disease remains poorly understood. Although routine clinical analysis of BNP is performed by immunoassays, it is challenging to use such techniques to account for cleaved or alternatively modified peptidoforms whose characterization may reveal important diagnostic and prognostic insights.

The absence of quantitative methods capable of identifying cleavage products is a bottleneck that obscures clinically important functional differences. The inventors have built an assay that monitor formation of two or more fragments of BNP and also can determine the enzymatic activity which should better reflect the biological status of patients.

While plasma sampling eliminates the input of newly secreted BNP, the dynamic enzymatic degradation of BNP and cleavage peptidoforms derived therefrom by endogenous enzymes makes reproducible and accurate quantification of BNP and cleavage peptidoforms concentrations in plasma samples difficult.

As such there exists an ongoing need for improved methods and tools for characterizing and quantifying BNP and cleavage peptidoforms derived therefrom in a biological sample. In various embodiments, the present invention meets that need by providing non-natural natriuretic peptides comprising one or more D-amino acids, which are not susceptible to the type of enzymatic cleavage in plasma that results in the degradation of BNP and cleavage peptidoforms derived therefrom. In some embodiments, the non-natural natriuretic peptides of the invention may be used as internal standards in various methods described herein for the diagnosis and/or prognosis of various diseases. Other non-limiting uses of the non-natural natriuretic peptides of the invention are described herein.

SUMMARY OF THE INVENTION

The following embodiments and aspects thereof are described and illustrated in conjunction with systems, articles of manufacture, compositions and methods which are meant to be exemplary and illustrative, not limiting in scope.

In various embodiments, the present invention provides a method, for determining the risk of developing cardiovascular disease in a subject, comprising: obtaining a biological sample comprising one or more proteases from the subject; adding a quantity of one or more natriuretic peptides to the biological sample; and detecting the presence of one or more cleavage products of the one or more natriuretic peptides over a period of time, wherein the presence of one or more cleavage products is indicative of an increased risk of the subject developing cardiovascular disease. In some embodiments, the method further comprises selecting one or more treatments for the subject if the increased risk of developing cardiovascular disease is determined. In some embodiments, the natriuretic peptides are any one or more of Brain natriuretic peptide (BNP), Atrial natriuretic peptide (ANP), C-type natriuretic peptide (CNP) or combinations thereof. In some embodiments, the proteases are any one or more of neutral endopeptidase, dipeptidylpeptidase IV, insulin degrading enzyme or combination thereof. In some embodiments, the sample is plasma, blood, or serum. In some embodiments, the period of time is up to 1 hour. In some embodiments, the period of time is up to 14 hours. In some embodiments, the cleavage products are any one or more of BNP 3-30, BNP 3-29, BNP 3-32, BNP 1-30 or combinations thereof. In some embodiments, the cleavage products are any one or more of BNP 3-30, BNP 3-29, BNP 3-32, BNP 1-30, BNP 5-29, BNP 4-29, BNP 1-28, BNP 1-29, BNP 4-31, BNP 4-32 or combinations thereof. In some embodiments, the cleavage products are any one or more of BNP 3-30, BNP 3-29, BNP 3-32, BNP 1-30, BNP 1-29, BNP 1-28, BNP 2-31, BNP 3-30, BNP 4-30, BNP 4-29, BNP 4-27, BNP 5-32, BNP 5-31, BNP 5-29, BNP 4-32, BNP 4-31, or combinations thereof. In some embodiments, the cleavage products are any one or more of 30-32, 25-30, 20-25, 25-32, 15-20, 10-15, 5-10, 10-20 or 20-30 consecutive amino acids of the natriuretic peptides. In some embodiments, the cleavage products are not modified. In some embodiments, the cleavage products are modified. In some embodiments, the modification is oxidation at the methionine residue. In some embodiments, the cleavage products are detected using any one or more of capillary electrophoresis/electrospray ionization-mass spectrometry (CESI-MS), capillary electrophoresis-mass spectrometry (CE-MS), liquid chromatography mass spectrometry (LC-MS), high pressure liquid chromatography mass spectrometry (HPLC-MS), or combinations thereof. In some embodiments, the quantity of one or more natriuretic peptides added to the sample is about any one or more of 10 ng/µL, 50 ng/µL, 75 ng/µL, 100 ng/µL, 125 ng/µL, 150 ng/µL, 175 ng/µL, 200 ng/µL, 225 ng/µL, 250 ng/µL, 275 ng/µL, 300 ng/µL, 350 ng/µL, 375 ng/µL, 400 ng/µL, 450 ng/µL, 475 ng/µL, 500 ng/µL or combinations thereof. In some embodiments, the cardiovascular disease is heart failure, arterial fibrillation or combination thereof. In some embodiments, the method further comprises comparing the presence of one or more cleavage products of the one or more natriuretic peptides from the subject to the presence of one or more cleavage products of the one or more natriuretic peptides from a reference sample. In some embodiments, the method further comprises making an assessment of the subject based on the comparison, wherein the assessment is a determination of the risk of developing cardiovascular disease. In some embodiments, the reference sample is obtained from a healthy subject. In some embodiments, the reference sample is obtained from a subject that has been treated for the cardiovascular disease. In some embodiments, the reference sample is obtained from the subject at an earlier point in time. In some embodiments, the reference sample is obtained from the subject before the subject is treated for the cardiovascular disease. In some embodiments, the method further comprises detecting the presence of one or more natriuretic peptides over a period of time.

As opposed to current assays that measure BNP as a marker for cardiovascular disease severity, our invention measures the activity of at least three proteases present in plasma (neutral endopeptidase, dipeptidylpeptidase IV, and insulin degrading enzyme) by measuring the extent to which they cleave BNP1-32 into its product fragments. Plasma proteases that affect the relative amounts of BNP cleavage products can modulate the relative strength with which BNP induces signaling. As such, their collective activities represent a fundamental mechanism of deleterious signaling in cardiovascular disease.

BRIEF DESCRIPTION OF THE DRAWINGS

Exemplary embodiments are illustrated in referenced figures. It is intended that the embodiments and figures disclosed herein are to be considered illustrative rather than restrictive.

FIG. 1 depicts in accordance with various embodiments of the invention, a schematic representation of B-type natriuretic peptide structure, cleavage processing, and degradation. ProBNP1-108 and signal peptide, cleaved to NT-proBNP1-76 and the active hormone BNP1-32. The solid black line with the scissors pictogram indicates the processing site of the enzymes Furin and Corin. Blue and green lines with scissor pictograms show the processing site on BNP that occur in the peripheral circulation as a result of three known circulating peptidases: neutral endopeptidase (NEP), dipeptidylpeptidase IV (DPPIV), and insulin degrading enzyme (IDE). FIG. 1 discloses SEQ ID NOs: 1, 2, and 7.

FIG. 2 depicts in accordance with various embodiments of the invention, the sequences of pre-proBNP, proBNP, NT-proBNP, and BNP itself, along with residues putatively modified by 0-glycosylation, and known epitope regions targeted by detection antibodies. FIG. 2 discloses SEQ ID NOs: 4, 5, 6, and 7.

FIG. 3 depicts in accordance with various embodiments of the invention, an overview of the materials and methods, as well as a representative time program of the CE separation with 3 sample segments injected by multi-segment injection.

FIG. 4 depicts in accordance with various embodiments of the invention, a schematic diagram of the CESI-MS interface and multi-segment injection (MSI), alongside the mathematic separation principle that underscores CE-based separations.

FIG. 8A-FIG. 8B depicts in accordance with various embodiments of the invention, the reproducibility of the CESI-MS with multi-segment injection using (FIG. 8A) the intra-run and inter-run peak area CV of $BNP_{1-32}$ of successive CE-MS experiments with three-segment multi-segment injection using standard $BNP_{1-32}$ dissolved in water, and (FIG. 8B). The inter-run migration time for each of the three segments within a run of standard $BNP_{1-32}$ dissolved in water.

(FIG. 12B) daughter ion mapping of $BNP_{3-32}$ fragments. FIG. 12B discloses SEQ ID NO: 8.

(FIG. 13A) Control human serum. (FIG. 13B) Patient (>40 years old) after spiked (adding) in serum sample, $BNP_{1-32}$ was rapidly cleaved in both group, however the $BNP_{3-29}$ profile showed a significant increase beyond the control.

(FIG. 17A) depicts representative electropherograms of the total ion chromatogram and extracted ion chromatogram for $BNP_{1-32}$, $BNP_{3-32}$, $BNP_{3-29}$, $BNP_{1-30}$ and $BNP_{3-30}$. We extracted the accurate $MS^1$ spectra of the most abundant charge state for each profiled BNP peptidoform: $BNP_{1-32}$ with 5+ charge, $BNP_{3-32}$ with 5+, $BNP_{3-29}$ with 4+ charge, $BNP_{1-30}$ with 5+ charge, and $BNP_{3-30}$ with 5+ charge. (FIG. 17B) depicts the time course profile of $BNP_{1-32}$ and each peptidoform as individual peak areas over a total of 14 hrs post-pulse (n=3). Note: Peaks below the quantitative threshold of 5e5 could not be accurately quantified and were excluded.

FIG. 20 discloses SEQ ID NOs: 1, 2 and 7.

FIG. 22 depicts in accordance with various embodiments of the invention, the concept of linking Capillary Electrophoresis with Mass Spectrometry, alongside the strengths of this technique as they pertain to the detection of $BNP_{1-32}$ processing in a plasma matrix.

FIG. 30 depicts in accordance with various embodiments of the invention, an iteration of our approach in which a 5-point proteolysis profile is produced from plasma within one hour. Upper panel depicts the time breakdown for each experimental phase. The lower left panel shows the representative extracted ion electropherograms, while the lower right panel shows the 5-point profile of the ratio of $BNP_{3-32}:BNP_{1-32}$ over 30 minutes.

FIG. 32 discloses SEQ ID NOs: 9, 10, and 11.

FIG. 33 discloses SEQ ID NO: 11.

DETAILED DESCRIPTION OF THE INVENTION

Figure 5:
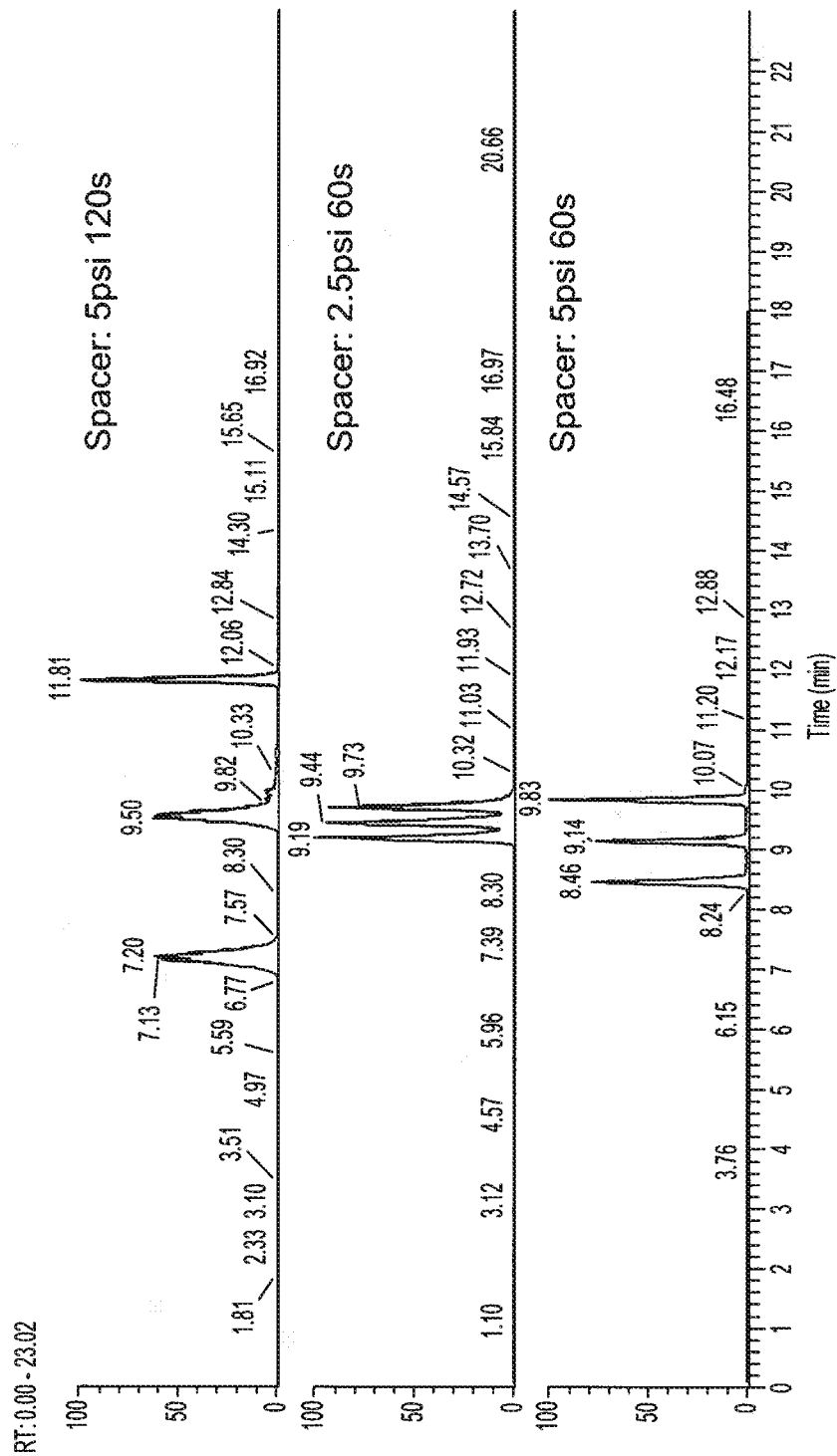
FIG. 5 depicts in accordance with various embodiments of the invention, the Total Ion Chromatogram of the effect of three spacer conditions to facilitate multi-segment injection with CESI-MS using standard $BNP_{1-32}$ dissolved in water. 10% HAc was used as spacer to separate samples injected in one run. Spacer was adjusted by injection time and pressure.
Figure 6:
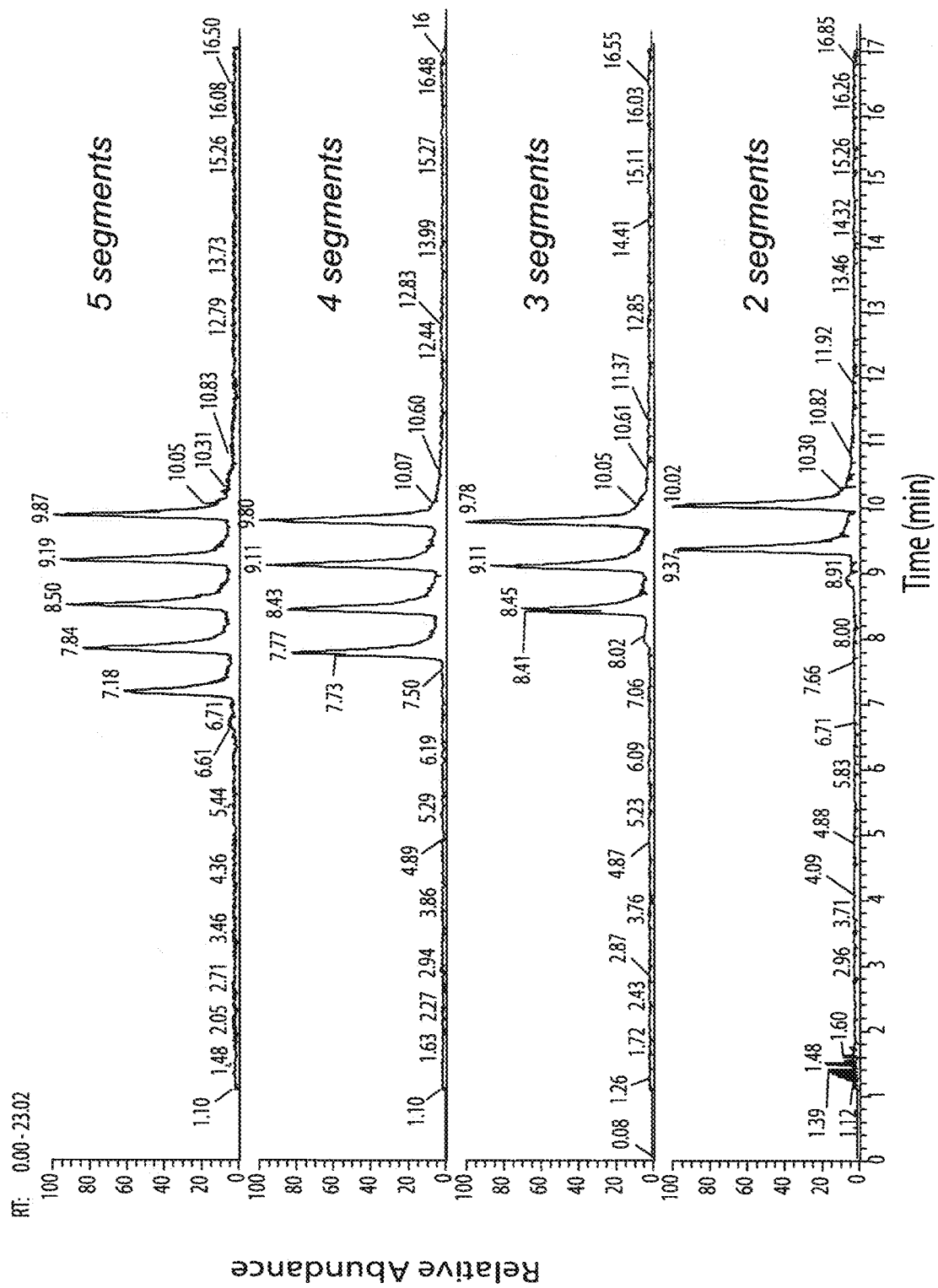
FIG. 6 depicts in accordance with various embodiments of the invention, the Total Ion Chromatogram upon injecting 2, 3, 4, or 5 segments on the within one CESI-MS run.
Figure 7:
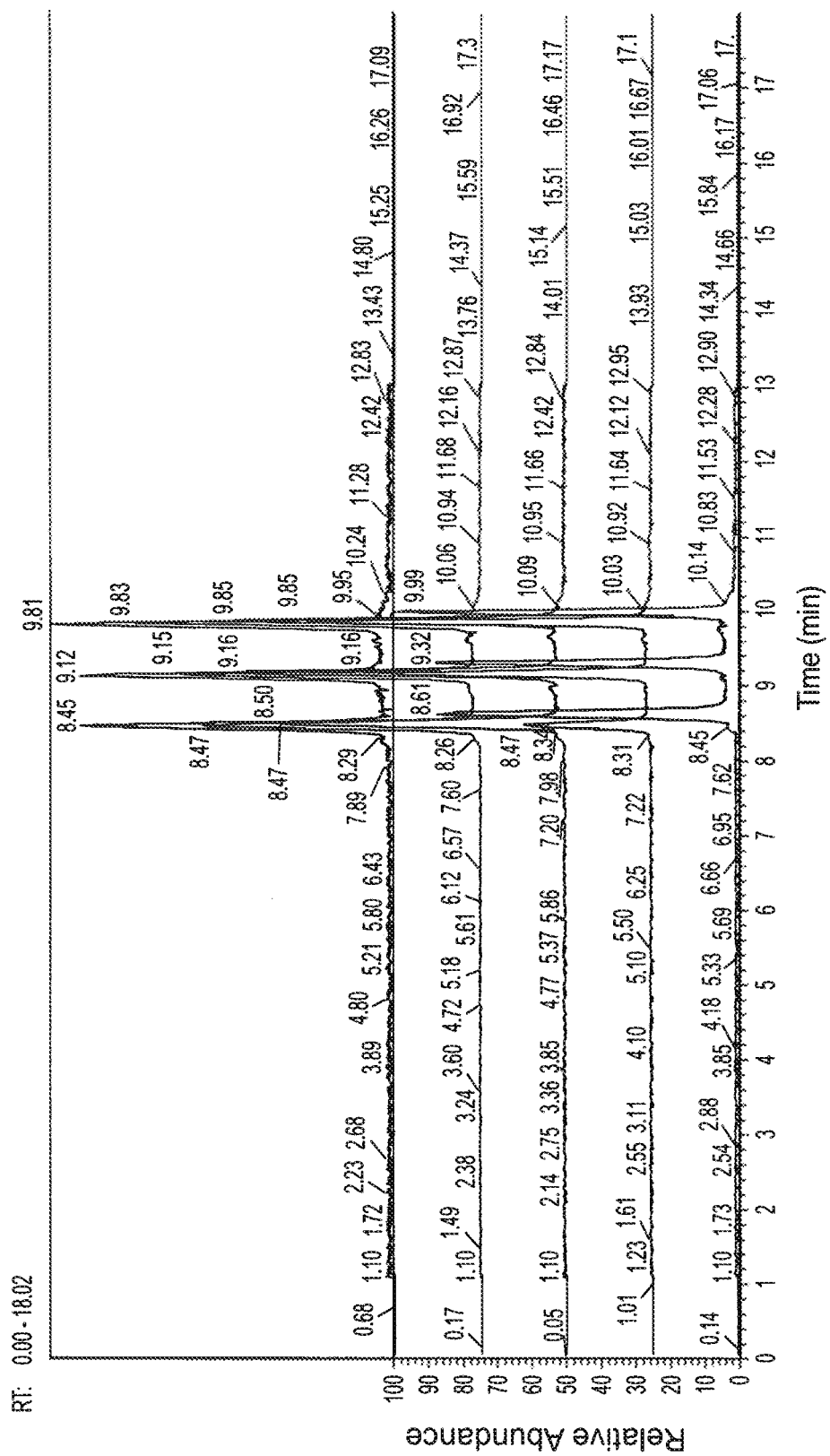
FIG. 7 depicts in accordance with various embodiments of the invention, the reproducibility of three sequentially injected standard samples of recombinant $BNP_{1-32}$, as depicted by the overlaid electropherograms of five separate experiments conducted by Capillary Electrophoresis.
Figure 9:
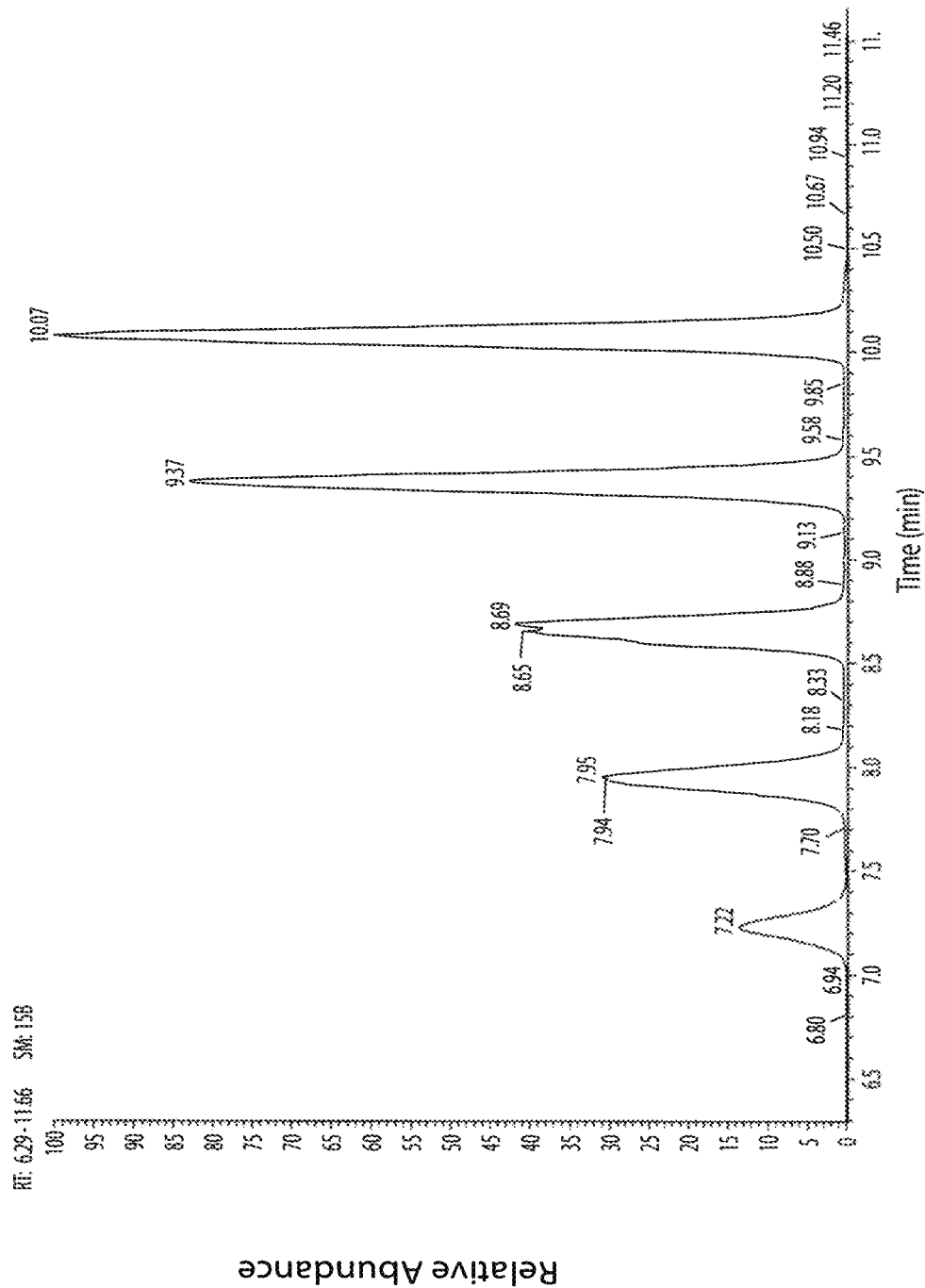
FIG. 9 depicts in accordance with various embodiments of the invention, the extracted ion chromatogram of $BNP_{1-32}$ (+5 charge state) by injecting 5 different concentrations of recombinant $BNP_{1-32}$ standard solution within one CESI-MS experiment using 5-segment multi-segment injection.
Figures 10A, 10B:
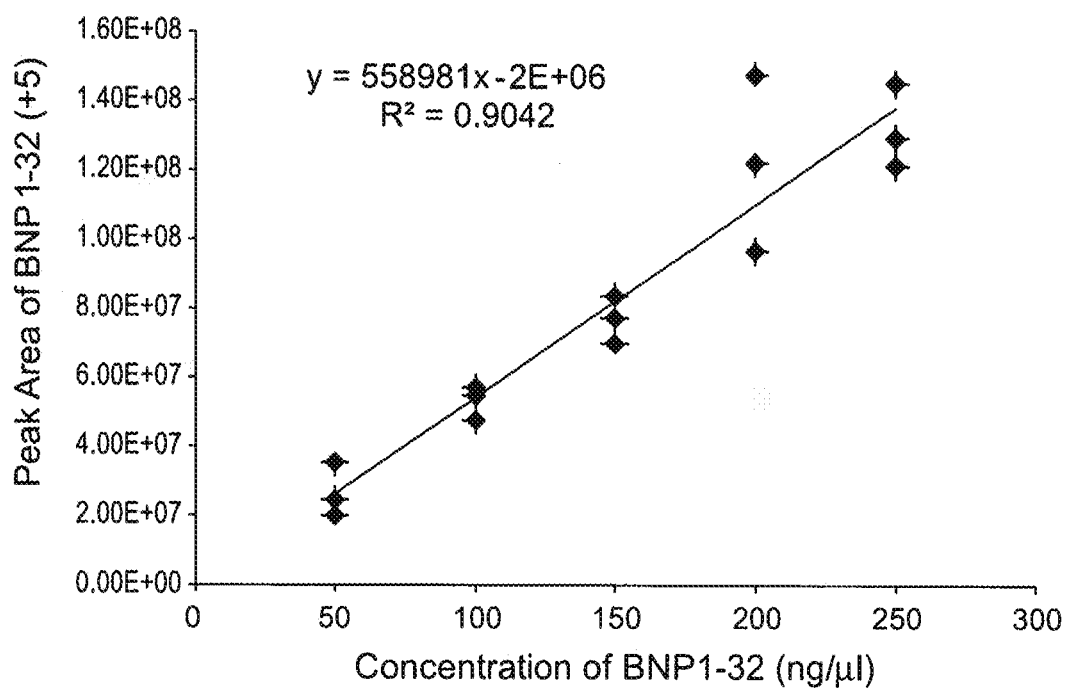
FIG. 10A-FIG. 10B depicts in accordance with various embodiments of the invention, (FIG. 10A) an initial calibration curve of $BNP_{1-32}$ by hydrodynamically injecting 5 segments consisting of different recombinant $BNP_{1-32}$ standard solution concentrations for CESI-MS analysis by 5-segment multi-segment injection. Each CESI-MS run produced a complete set of peaks for the five concentrations, and the experiment was performed in triplicate (n=3 runs) (FIG. 10B). The reproducibility of the 5-point $BNP_{1-32}$ calibration curves as measured by CESI-MS with five segment multi-segment injection (N=3).
Figure 11:
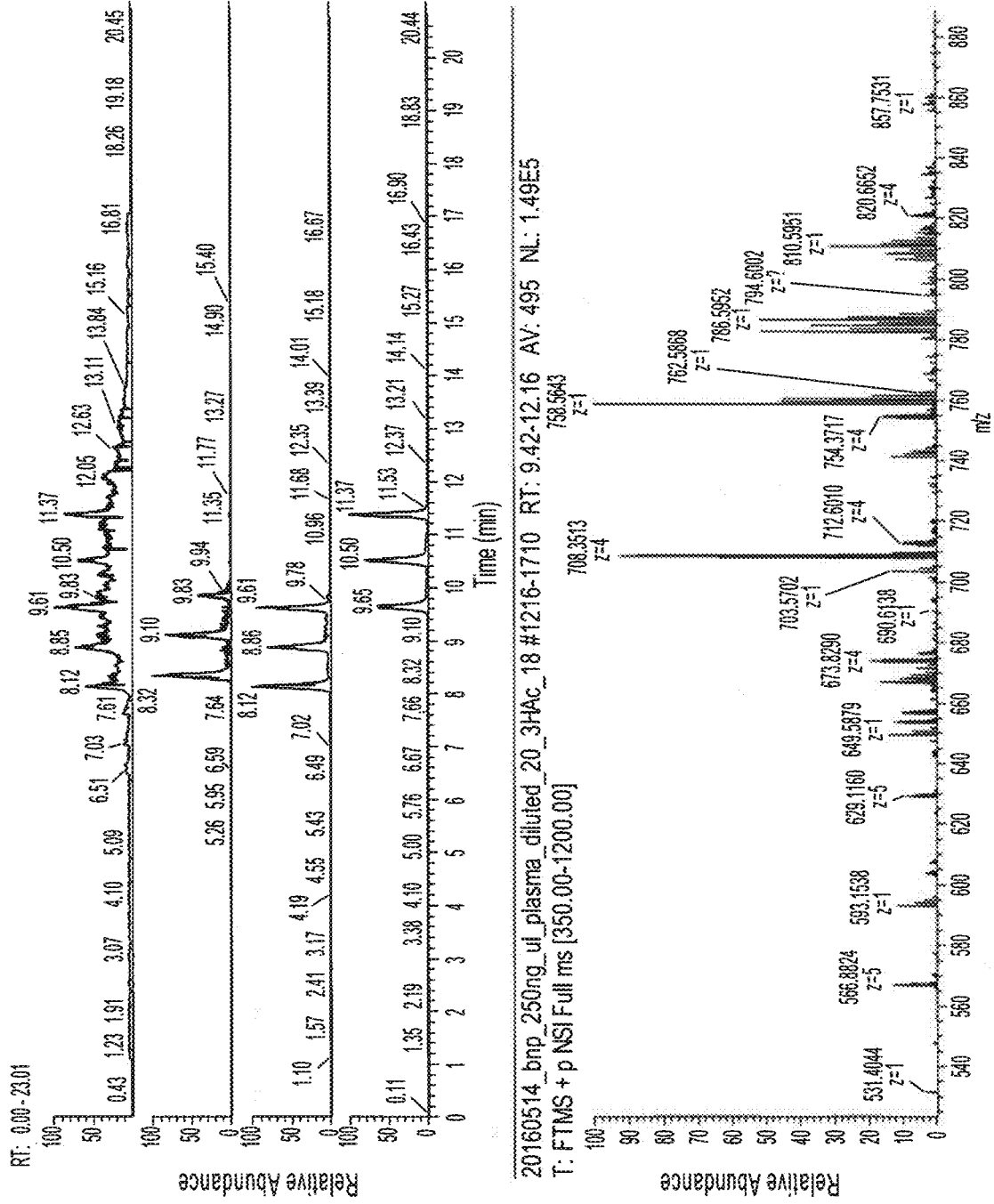
FIG. 11 depicts in accordance with various embodiments of the invention, the total ion chromatogram, the extracted ion chromatograms of $BNP_{1-32}$ $BNP_{3-32}$, and $BNP_{3-29}$, and the MS spectrum of $BNP_{1-32}$ spiked into patient serum (patient age >40). Unlike control serum, an unknown peak of m/z 708 was significantly increased in patient serum.
Figure 12A:
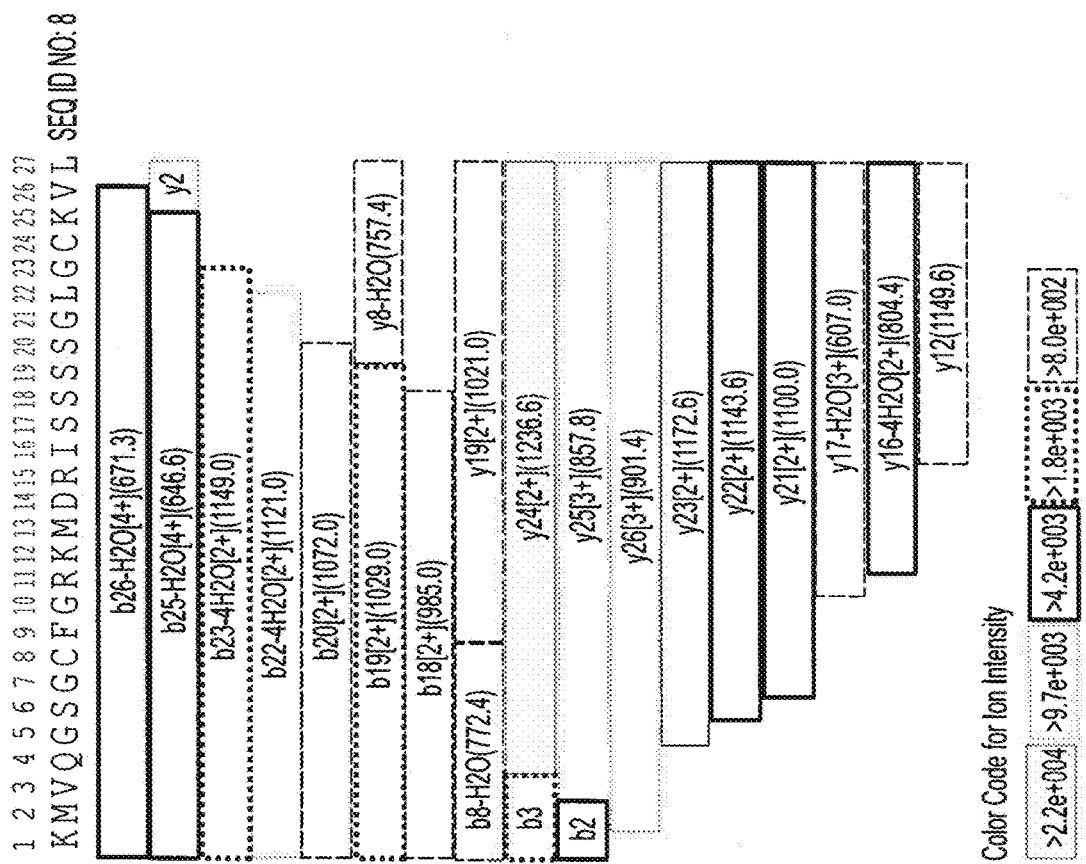
FIG. 12A-FIG. 12B depicts in accordance with various embodiments of the invention, (FIG. 12A) the comparison of the $MS^2$ spectrum of the unknown peak 708 and the in silica predicted $MS^2$ spectrum of $BNP_{3-29}$.
Figure 12B:
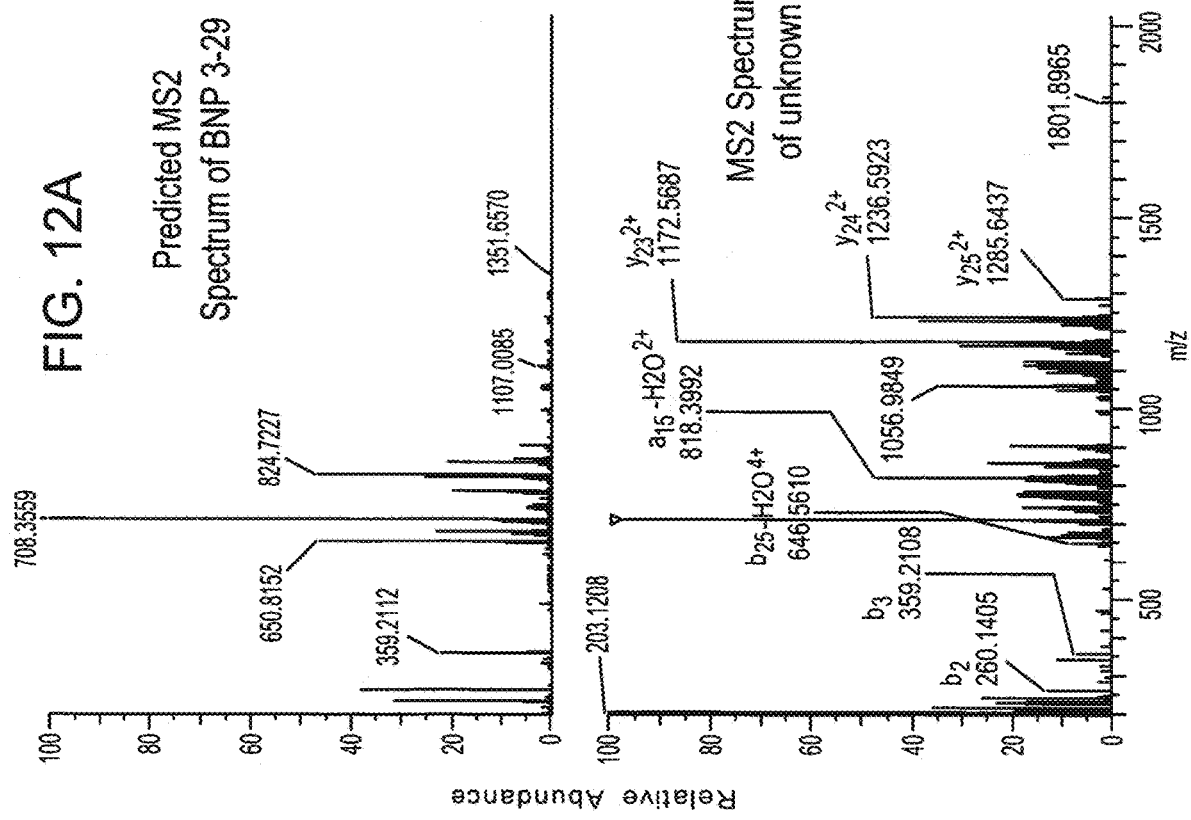
Figure 13A:
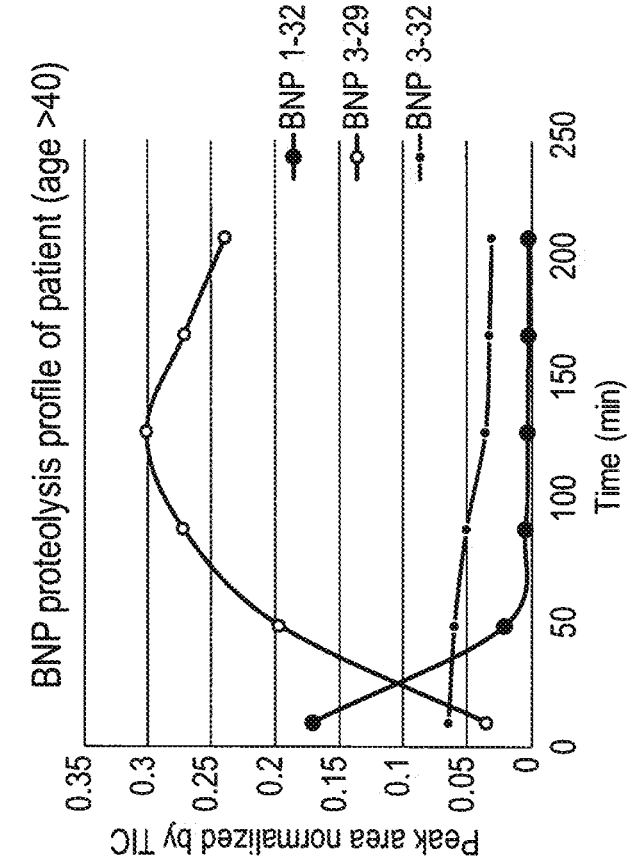
FIG. 13A-FIG. 13B depicts in accordance with various embodiments of the invention, the time-dependent profile curves of $BNP_{1-32}$, $BNP_{3-32}$ and $BNP_{3-29}$ in two different human samples.
Figure 13B:
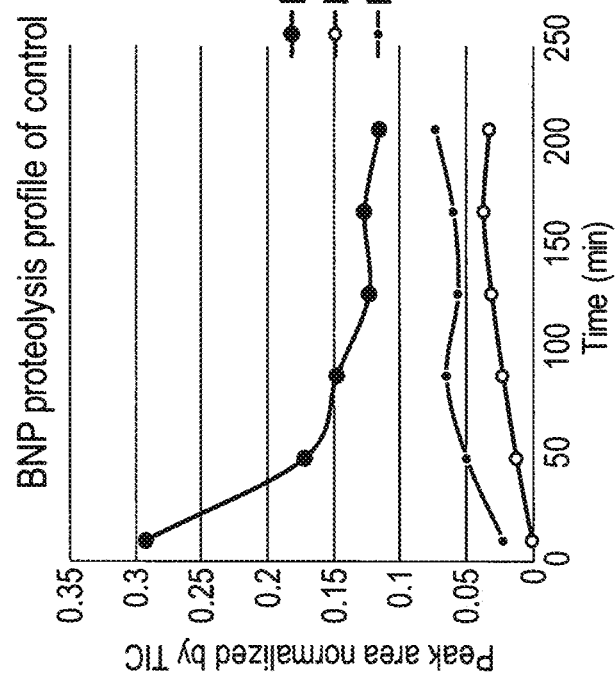

All references cited herein are incorporated by reference in their entirety as though fully set forth. Unless defined otherwise, technical and scientific terms used herein have the same meaning as commonly understood by one of ordinary skill in the art to which this invention belongs. Allen et al., *Remington: The Science and Practice of Pharmacy* $22^{nd}$ ed., Pharmaceutical Press (Sep. 15, 2012); Hornyak et al., *Introduction to Nanoscience and Nanotechnology*, CRC Press (2008); Singleton and Sainsbury, *Dictionary of Microbiology and Molecular Biology* $3^{rd}$ ed., revised ed., J. Wiley & Sons (New York, N.Y. 2006); Smith, *March's Advanced Organic Chemistry Reactions, Mechanisms and Structure* $7^{th}$ ed., J. Wiley & Sons (New York, N.Y. 2013); Singleton, *Dictionary of DNA and Genome Technology* $3^{rd}$ ed., Wiley-Blackwell (Nov. 28, 2012); and Green and Sambrook, *Molecular Cloning: A Laboratory Manual* 4th ed., Cold Spring Harbor Laboratory Press (Cold Spring Harbor, N.Y. 2012), provide one skilled in the art with a general guide to many of the terms used in the present application. For references on how to prepare antibodies, see Greenfield, *Antibodies A Laboratory Manual* $2^{nd}$ ed., Cold Spring Harbor Press (Cold Spring Harbor N.Y., 2013); Köhler and Milstein, *Derivation of specific antibody-producing tissue culture and tumor lines by cell fusion*, Eur. J. Immunol. 1976 Jul. 6(7):511-9; Queen and Selick, *Humanized immunoglobulins*, U.S. Pat. No. 5,585,089 (1996 December); and Riechmann et al., *Reshaping human antibodies for therapy*, Nature 1988 Mar. 24, 332(6162):323-7.

For references on mass spectrometry and proteomics, see e.g., Salvatore Sechi, *Quantitative Proteomics by Mass Spectrometry (Methods in Molecular Biology)* 2nd ed. 2016 Edition, Humana Press (New York, N.Y., 2009); Daniel Martins-de-Souza, Shotgun *Proteomics: Methods and Protocols* 2014 edition, Humana Press (New York, N.Y., 2014); Jörg Reinders and Albert Sickmann, *Proteomics: Methods and Protocols (Methods in Molecular Biology)* 2009 edition, Humana Press (New York, N.Y., 2009); and Jörg Reinders, *Proteomics in Systems Biology: Methods and Protocols (Methods in Molecular Biology)* $1^{st}$ ed. 2016 edition, Humana Press (New York, N.Y., 2009).

One skilled in the art will recognize many methods and materials similar or equivalent to those described herein, which could be used in the practice of the present invention. Other features and advantages of the invention will become apparent from the following detailed description, taken in conjunction with the accompanying drawings, which illustrate, by way of example, various features of embodiments of the invention. Indeed, the present invention is in no way limited to the methods and materials described. For convenience, certain terms employed herein, in the specification, examples and appended claims are collected here.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. It should be understood that this invention is not limited to the particular methodology, protocols, and reagents, etc., described herein and as such can vary. The definitions and terminology used herein are provided to aid in describing particular embodiments, and are not intended to limit the claimed invention, because the scope of the invention is limited only by the claims.

As used herein the term "comprising" or "comprises" is used in reference to compositions, methods, kits, systems, articles, and respective component(s) thereof, that are useful to an embodiment, yet open to the inclusion of unspecified elements, whether useful or not. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

Unless stated otherwise, the terms "a" and "an" and "the" and similar references used in the context of describing a particular embodiment of the application (especially in the context of claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. The abbreviation, "e.g." is derived from the Latin exempli gratia, and is used herein to indicate a non-limiting example. Thus, the abbreviation "e.g." is synonymous with the term "for example." No language in the specification should be construed as indicating any non-claimed element essential to the practice of the application.

As used herein, the terms "treat," "treatment," "treating," or "amelioration" when used in reference to a disease, disorder or medical condition, refer to both therapeutic treatment and prophylactic or preventative measures, wherein the object is to reverse, alleviate, ameliorate, inhibit, lessen, slow down or stop the progression or severity of a symptom, a condition, a disease, or a disorder The term "treating" includes reducing or alleviating at least one adverse effect or symptom of a condition, a disease, or a disorder. Treatment is generally "effective" if one or more symptoms or clinical markers are reduced. Alternatively, treatment is "effective" if the progression of a disease, disorder or medical condition is reduced or halted. That is, "treatment" includes not just the improvement of symptoms or markers, but also a cessation or at least slowing of progress or worsening of symptoms that would be expected in the absence of treatment. Also, "treatment" may mean to pursue or obtain beneficial results, or lower the chances of the individual developing the condition, disease, or disorder even if the treatment is ultimately unsuccessful. Those in need of treatment include those already with the condition, disease, or disorder as well as those prone to have the condition, disease, or disorder or those in whom the condition, disease, or disorder is to be prevented. Non-limiting examples of treatments or therapeutic treatments include pharmacological therapies (including but not limited to angiotensin receptor blockers, Acetylcholinesterase inhibitors, Aldosterone inhibitors, Beta-blockers, Diuretics) and/or interventional surgical treatments (including but not limited to bypass surgery, valve surgery, left ventricular assist devices).

In various embodiments, the treatments or kits may be provided as pharmaceutical compositions. In various embodiments, the pharmaceutical compositions may be formulated for delivery via any route of administration. "Route of administration" may refer to any administration pathway known in the art, including but not limited to aerosol, nasal, via inhalation, oral, transmucosal, transdermal, parenteral, enteral, topical or local. "Parenteral" refers to a route of administration that is generally associated with injection, including intracranial, intraventricular, intrathecal, epidural, intradural, intraorbital, infusion, intracapsular, intracardiac, intradermal, intramuscular, intraperitoneal, intrapulmonary, intraspinal, intrasternal, intrathecal, intrauterine, intravascular, intravenous, intraarterial, subarachnoid, subcapsular, subcutaneous, transmucosal, or transtracheal. Via the parenteral route, the compositions may be in the form of solutions or suspensions for infusion or for injection, or as lyophilized powders. Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release. Via the topical route, the pharmaceutical compositions can be in the form of aerosol, lotion, cream, gel, ointment, suspensions, solutions or emulsions. Methods for these administrations are known to one skilled in the art. In certain embodiments, the pharmaceutical compositions are formulated for intravascular, intravenous, or intraarterial administration.

In various embodiments, the pharmaceutical compositions can contain any pharmaceutically acceptable excipient. "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous. Examples of excipients include but are not limited to starches, sugars, microcrystalline cellulose, diluents, granulating agents, lubricants, binders, disintegrating agents, wetting agents, emulsifiers, coloring agents, release agents, coating agents, sweetening agents, flavoring agents, perfuming agents, preservatives, antioxidants, plasticizers, gelling agents, thickeners, hardeners, setting agents, suspending agents, surfactants, humectants, carriers, stabilizers, and combinations thereof.

In various embodiments, the pharmaceutical compositions can contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its imaging benefits.

The pharmaceutical compositions can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical compositions are made following the conventional techniques of pharmacy involving dry milling, mixing, and blending for powder forms; milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

Before administration to patients, formulants may be added to the pharmaceutical composition. A liquid formulation may be preferred. For example, these formulants may include oils, polymers, vitamins, carbohydrates, amino acids, salts, buffers, albumin, surfactants, bulking agents or combinations thereof.

Carbohydrate formulants include sugar or sugar alcohols such as monosaccharides, disaccharides, or polysaccharides, or water soluble glucans. The saccharides or glucans can include fructose, dextrose, lactose, glucose, mannose, sorbose, xylose, maltose, sucrose, dextran, pullulan, dextrin, alpha and beta cyclodextrin, soluble starch, hydroxethyl starch and carboxymethylcellulose, or mixtures thereof "Sugar alcohol" is defined as a C4 to C8 hydrocarbon having an —OH group and includes galactitol, inositol, mannitol, xylitol, sorbitol, glycerol, and arabitol. These sugars or sugar alcohols mentioned above may be used individually or in combination. There is no fixed limit to amount used as long as the sugar or sugar alcohol is soluble in the aqueous preparation. In one embodiment, the sugar or sugar alcohol concentration is between 1.0 w/v % and 7.0 w/v %, more preferable between 2.0 and 6.0 w/v %.

Amino acids formulants include levorotary (L) forms of carnitine, arginine, and betaine; however, other amino acids may be added.

Polymers formulants include polyvinylpyrrolidone (PVP) with an average molecular weight between 2,000 and 3,000, or polyethylene glycol (PEG) with an average molecular weight between 3,000 and 5,000.

A buffer may also be used in the pharmaceutical compositions to minimize pH changes in the solution before lyophilization or after reconstitution. Most any physiological buffer may be used including but not limited to citrate, phosphate, succinate, and glutamate buffers or mixtures thereof. In some embodiments, the concentration is from 0.01 to 0.3 molar. Surfactants that can be added to the formulation are shown in EP Nos. 270,799 and 268,110.

After the pharmaceutical composition is prepared, it may be lyophilized to prevent degradation and to preserve sterility. Methods for lyophilizing pharmaceutical compositions are known to those of ordinary skill in the art. Just prior to use, the pharmaceutical composition may be reconstituted with a sterile diluent (Ringer's solution, distilled water, or sterile saline, for example) which may include additional ingredients. Upon reconstitution, the pharmaceutical composition is administered to subjects using those methods that are known to those skilled in the art.

The pharmaceutical compositions may be sterilized by conventional, well-known sterilization techniques. The resulting solutions may be packaged for use or filtered under aseptic conditions and lyophilized, the lyophilized preparation being combined with a sterile solution prior to administration. The pharmaceutical compositions may contain pharmaceutically-acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, and stabilizers (e.g., 1-20% maltose, etc.).

Many variations and alternative elements have been disclosed in embodiments of the present invention. Still further variations and alternate elements will be apparent to one of skill in the art. Various embodiments of the invention can specifically include or exclude any of these variations or elements.

In some embodiments, the numbers expressing quantities of ingredients, properties such as concentration, reaction conditions, time, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

"Beneficial results" or "desired results" may include, but are in no way limited to, lessening or alleviating the severity of the disease condition, preventing the disease condition from worsening, curing the disease condition, preventing the disease condition from developing, lowering the chances of a patient developing the disease condition, lessening or alleviating the severity of the disease or condition, preventing the disease or condition from worsening, curing the disease or condition, preventing the disease or condition from developing, lowering the chances of a patient developing the disease or condition, decreasing morbidity and mortality, and prolonging a patient's life or life expectancy. As non-limiting examples, "beneficial results" or "desired results" may be alleviation of one or more symptom(s), diminishment of extent of the deficit, stabilized (i.e., not worsening) state of a cardiovascular disease, delay or slowing of a cardiovascular disease, and amelioration or palliation of symptoms associated with a cardiovascular disease.

As used herein, the term "administering," refers to the placement an agent or a treatment as disclosed herein into a subject by a method or route which results in at least partial localization of the agent or treatment at a desired site. "Route of administration" may refer to any administration pathway known in the art, including but not limited to aerosol, nasal, via inhalation, oral, anal, intra-anal, peri-anal, transmucosal, transdermal, parenteral, enteral, topical or local. "Parenteral" refers to a route of administration that is generally associated with injection, including intratumoral, intracranial, intraventricular, intrathecal, epidural, intradural, intraorbital, infusion, intracapsular, intracardiac, intradermal, intramuscular, intraperitoneal, intrapulmonary, intraspinal, intrasternal, intrathecal, intrauterine, intravascular, intravenous, intraarterial, subarachnoid, subcapsular, subcutaneous, transmucosal, or transtracheal. Via the parenteral route, the compositions may be in the form of solutions or suspensions for infusion or for injection, or as lyophilized powders. Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release. Via the topical route, the pharmaceutical compositions can be in the form of aerosol, lotion, cream, gel, ointment, suspensions, solutions or emulsions. In accordance with the present invention, "administering" can be self-administering. For example, it is considered as "administering" that a subject consumes a composition as disclosed herein.

The term "Brain natriuretic peptide" or "B type natriuretic peptide" or "BNP" or "BNP 1-32" as used herein refers to the mature 32-amino acid B type natriuretic peptide molecule.

A "cardiovascular disease," as used herein, refers to a disorder of the heart and blood vessels, and includes disorders of the arteries, veins, arterioles, venules, and capillaries. Non-limiting examples of cardiovascular diseases diagnosed by a method described herein can include congestive heart failure (HF), coronary artery disease (CAD), arrhythmia, pericarditis, and acute myocardial infarction (MI). Non-limiting examples of cardiovascular disease include: coronary artery disease, coronary heart disease, ischemic heart disease (IHD), cardiomyopathy, stroke, hypertensive heart disease, heart failure, pulmonary heart disease, ischemic syndrome, coronary microvascular disease, cardiac dysrhythmias, rheumatic heart disease (RHD), aortic aneurysms, cardiomyopathy, atrial fibrillation, congenital heart disease, endocarditis, inflammatory heart disease, endocarditis, inflammatory cardiomegaly, myocarditis, valvular heart disease, cerebrovascular disease, and peripheral artery disease (PAD). Additional non-limiting examples of cardiovascular diseases include heart failure subclasses (e.g. Heart failure with preserved ejection fraction, heart failure with reduced ejection fraction, ischemic or dilated cardiomyopathies) and atrial fibrillation or atrial septal defect).

As used herein, the term "heart failure" refers to the pathophysiological state in which the heart is unable to pump blood at a rate commensurate with the requirements of the metabolizing tissues or can do so only from an elevated filling pressure.

"Diagnostic" means identifying the presence or nature of a pathologic condition, disease, or disorder and includes identifying patients who are at risk of developing a specific condition, disease or disorder. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, a disease, or a disorder, it suffices if the method provides a positive indication that aids in diagnosis.

By "at risk of" is intended to mean at increased risk of, compared to a normal subject, or compared to a control group, e.g. a patient population. Thus a subject carrying a particular marker may have an increased risk for a specific condition, disease or disorder, and be identified as needing further testing. "Increased risk" or "elevated risk" mean any statistically significant increase in the probability, e.g., that the subject has the disorder. The risk is preferably increased by at least 10%, more preferably at least 20%, and even more preferably at least 50% over the control group with which the comparison is being made.

The term "statistically significant" or "significantly" refers to statistical evidence that there is a difference. It is defined as the probability of making a decision to reject the null hypothesis when the null hypothesis is actually true. The decision is often made using the p-value.

The terms "detection", "detecting" and the like, may be used in the context of detecting cleavage products of the natriuretic peptides, or of detecting a disease or disorder (e.g. when positive assay results are obtained). In the latter context, "detecting" and "diagnosing" are considered synonymous. The terms "detection", "detecting" and the like, may be used in the context of detecting one or more L-natriuretic peptides (for example, a natural natriuretic peptide or a cleavable synthetic natriuretic peptide, where the natural natriuretic peptide can be endogenous or exogenous), detecting one or more non-natural natriuretic peptides, detecting one or more of the cleavage products of the L-natriuretic peptides (e.g., L-natriuretic peptide cleavage product), detecting one or more non-natural cleavage peptidoforms, or of detecting a condition, a disease or a disorder (e.g. when positive assay results are obtained). In the latter context, "detecting" and "diagnosing" are considered synonymous.

The term "diagnosis," or "dx," refers to the identification of the nature and cause of a certain phenomenon. As used herein, a diagnosis typically refers to a medical diagnosis, which is the process of determining which disease or condition explains a symptoms and signs. A diagnostic procedure, often a diagnostic test or assay, can be used to provide a diagnosis. A diagnosis can comprise detecting the presence of a condition, disease or disorder or the risk of getting a condition, disease or disorder The term "prognosis," or "px," as used herein refers to predicting the likely outcome of a current standing. For example, a prognosis can include the expected duration and course of a condition, disease or disorder, such as progressive decline or expected recovery.

The term "theranosis," or "tx" as used herein refers to a diagnosis or prognosis used in the context of a medical treatment. For example, theranostics can include diagnostic testing used for selecting appropriate and optimal therapies (or the inverse) based on the context of genetic content or other molecular or cellular analysis. Theranostics includes pharmacogenomics, personalized and precision medicine.

"Antibody" refers to a polypeptide ligand substantially encoded by an immunoglobulin gene or immunoglobulin genes, or fragments thereof, which specifically binds and recognizes an epitope (e.g., an antigen). The recognized immunoglobulin genes include the kappa and lambda light chain constant region genes, the alpha, gamma, delta, epsilon and mu heavy chain constant region genes, and the myriad immunoglobulin variable region genes. Antibodies exist, e.g., as intact immunoglobulins or as a number of well characterized fragments produced by digestion with various peptidases. This includes, e.g., Fab' and F(ab)'2 fragments. The term "antibody," as used herein, also includes antibody fragments either produced by the modification of whole antibodies or those synthesized de novo using recombinant DNA methodologies. It also includes polyclonal antibodies, monoclonal antibodies, chimeric antibodies, humanized antibodies, or single chain antibodies. "Fc" portion of an antibody refers to that portion of an immunoglobulin heavy chain that comprises one or more heavy chain constant region domains, $CH_1$, $CH_2$ and $CH_3$, but does not include the heavy chain variable region.

Immunoassay" is an assay that uses an antibody to specifically bind an antigen (e.g., a marker). The immunoassay is characterized by the use of specific binding properties of a particular antibody to isolate, target, and/or quantify the antigen.

The terms "subject", "patient" or "individual" generally refer to a human, although the methods of the invention are not limited to humans, and should be useful in other animals (e.g. birds, reptiles, amphibians, mammals), particularly in mammals, since albumin is homologous among species. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, and canine species, e.g., dog, fox, wolf. The terms, "patient", "individual" and "subject" are used interchangeably herein. In an embodiment, the subject is mammal. The mammal can be a human, non-human primate, mouse, rat, dog, cat, horse, or cow, but are not limited to these examples. In addition, the methods described herein can be used to treat domesticated animals and/or pets. In various embodiments, the subject is a human.

In some embodiments, the subject is selected from the group consisting of a subject suspected of having cardiovascular disease, a subject that has cardiovascular disease, a subject diagnosed with cardiovascular disease, a subject that has been treated for cardiovascular disease, a subject that is being treated for cardiovascular disease, and a subject that is at risk of developing cardiovascular disease.

In some embodiments, the subject is selected from the group consisting of a subject suspected of having a disease, a subject that has a disease, a subject diagnosed with a disease, a subject that has been treated for a disease, a subject that is being treated for a disease, and a subject that is at risk of developing a disease.

"Mammal" as used herein refers to any member of the class Mammalia, including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term.

The terms "cleavage products" and "cleavage peptidoforms" have the same meaning and are used interchangeably herein, whereas the term "peptidoforms" encompasses the parent $BNP_{1-32}$ peptidoform as well as its cleavage peptidoforms.

The terms "cleavage products" and "cleavage peptidoforms" have the same meaning and are used interchangeably herein. The term "cleavage peptidoform" means a peptide that is derived from a natriuretic peptide, wherein the cleavage peptidoform contains at least one fewer amino acid (or amino acid residue) than the natriuretic peptide from which it is derived. In a non-limiting example, a cleavage peptidoform is formed through contact of a natriuretic peptide with a protease.

A subject can be one who has been previously diagnosed with or identified as suffering from or having a condition, disease, or disorder in need of treatment (e.g., a cardiovascular disease) or one or more complications related to the condition, disease, or disorder, and optionally, have already undergone treatment for the condition, disease, disorder, or the one or more complications related to the condition, disease, disorder. Alternatively, a subject can also be one who has not been previously diagnosed as having a condition, disease, or disorder or one or more complications related to the condition, disease, or disorder. For example, a subject can be one who exhibits one or more risk factors for a condition, disease, or disorder or one or more complications related to the condition, disease, or disorder or a subject who does not exhibit risk factors. A "subject in need" of treatment for a particular condition, disease, or disorder can be a subject suspected of having that condition, disease, or disorder, diagnosed as having that condition, disease, or disorder, already treated or being treated for that condition, disease, or disorder, not treated for that condition, disease, or disorder or at risk of developing that condition, disease, or disorder.

"Sample" is used herein in its broadest sense. The term "biological sample" as used herein denotes a sample taken or isolated from a biological organism. A sample or biological sample may comprise a bodily fluid including blood, serum, plasma, tears, aqueous and vitreous humor, spinal fluid; a soluble fraction of a cell or tissue preparation, or media in which cells were grown; or membrane isolated or extracted from a cell or tissue; polypeptides, or peptides in solution or bound to a substrate; a cell; a tissue; a tissue print; a fingerprint, skin or hair; fragments and derivatives thereof. Non-limiting examples of samples or biological samples include cheek swab; mucus; whole blood, blood, serum; plasma; urine; saliva; semen; lymph; fecal extract; sputum; other body fluid or biofluid; cell sample; and tissue sample etc. The term also includes a mixture of the above-mentioned samples or biological samples. The term "sample" also includes untreated or pretreated (or preprocessed) biological samples. In some embodiments, a sample or biological sample can comprise one or more cells from the subject. Subject samples or biological samples usually comprise derivatives of blood products, including blood, plasma and serum. In some embodiments, the sample is a biological sample. In some embodiments, the sample is plasma.

Sample collection procedures and devices known in the art are suitable for use with various embodiment of the present invention. Examples of sample collection procedures and devices include but are not limited to: phlebotomy tubes (e.g., a vacutainer blood/specimen collection device for collection and/or storage of the blood/specimen), dried blood spots, Microvette CB300 Capillary Collection Device (Sarstedt), HemaXis blood collection devices (microfluidic technology, Hemaxis), Volumetric Absorptive Microsampling (such as CE-IVD Mitra microsampling device for accurate dried blood sampling (Neoteryx), HemaSpot™-HF Blood Collection Device, a tissue collection device.

In some embodiments, the sample from the subject comprises one or more proteases from the subject. In some embodiments, the sample from the subject comprises one or more proteases. In some embodiments, the sample comprises one or more proteases. In some embodiments, the sample comprises one or more proteases from the subject.

The terms "proteases" and "peptidases" are used interchangeably herein to mean enzymes that breakdown proteins and peptides.

"Optional" or "optionally" means that the subsequently described circumstance may or may not occur, so that the description includes instances where the circumstance occurs and instances where it does not.

The term "condition" (biological state or health state) is understood in the present invention as status of a subject that can be described by physical, mental or social criteria. It includes as well so-called "healthy" and "diseased" conditions, therefore it is not limited to the WHO definition of health as "a state of complete physical, mental, and social well-being and not merely the absence of disease or infirmity." but includes disease and infirmity.

The term "disease" refers to an abnormal condition affecting the body of an organism. The term "disorder" refers to a functional abnormality or disturbance. The terms disease or disorder are used interchangeably herein unless otherwise noted or clear given the context in which the term is used.

The term "state of health" includes at least one condition as defined herein. It may also include a plurality of different conditions. In some embodiments, the state of health is a healthy state. In some embodiments, the state of health is a diseased state.

The term "healthy state" or "normal state" means that the state of a subject (e.g., biological state or health state, etc.) is not abnormal or does not comprise a disease or disorder. A "healthy subject" or "normal subject" is a subject that does not have a disease or disorder.

Non-limiting examples of diseases include, cardiovascular diseases (for example heart failure subclasses (e.g. Heart failure with preserved ejection fraction, heart failure with reduced ejection fraction, ischemic or dilated cardiomyopathies) and atrial fibrillation or atrial septal defect), heart transplant diseases, cancers, or kidney diseases, or neurological diseases, or a combination thereof.

The term "preventative treatment" means maintaining or improving a healthy state or non-diseased state of a healthy subject or subject that does not have a disease. The term "preventative treatment" also means to prevent or to slow the appearance of symptoms associated with a condition, disease, or disorder. The term "preventative treatment" also means to prevent or slow a subject from obtaining a condition, disease, or disorder.

The term "L-natriuretic peptide" as used herein means a natriuretic peptide that contains only L-amino acids or L-amino acid residues. In other words, without being bound by theory an L-natriuretic peptide does not contain D-amino acids or D-amino acid residues. Examples of L-natriuretic peptides are natural natriuretic peptides and cleavable synthetic natriuretic peptides. In some embodiments, the L-natriuretic peptide is selected from the group consisting of natural natriuretic peptide and cleavable synthetic natriuretic peptide.

The term "natural natriuretic peptide" as used herein means a naturally occurring natriuretic peptide or a natriuretic peptide that is synthesized in nature, for example by a biological organism (e.g., a mammal, a mouse, a human). Without being bound by theory, natural natriuretic peptides are synthesized in nature using L-amino acids. In other words, natural natriuretic peptides do not contain D-amino acids or D-amino acid residues. Non-limiting examples of natural natriuretic peptides include natural brain natriuretic peptide (natural BNP), natural atrial natriuretic peptide (natural ANP), and natural C-type natriuretic peptide (natural CNP), or combinations thereof. Natural natriuretic peptides may also contain one or more glycine (Gly) amino acids (or glycine (Gly) amino acid residues).

The term "natural brain natriuretic peptide (natural BNP)" as used herein means naturally occurring brain natriuretic peptide. Without being bound by theory, natural brain natriuretic peptide is synthesized in nature, for example by a biological organism, using L-amino acids. In other words, natural brain natriuretic peptide (natural BNP) does not contain D-amino acids or D-amino acid residues. Natural brain natriuretic peptide as used herein refers to the naturally occurring mature 32-amino acid B-type natriuretic peptide molecule. The terms "natural brain natriuretic peptide (natural BNP)" or "natural B-type natriuretic peptide" or "natural BNP" or "natural BNP 1-32" are used interchangeably herein. In one embodiment, natural BNP1-32 comprises, consists of, or consists essentially of the amino acid sequence SPKMVQGSGCFGRKMDRISSSSGLGCKVLRRH (SEQ ID NO: 7). In one embodiment, natural BNP 1-32 is amino acid sequence SPKMVQGSGCFGRKMDRISSSSGLGCKVLRRH (SEQ ID NO: 7).

The term "natural atrial natriuretic peptide (natural ANP)" as used herein means naturally occurring atrial natriuretic peptide. Without being bound by theory, natural atrial natriuretic peptide is synthesized in nature, for example by a biological organism, using L-amino acids. In other words, natural atrial natriuretic peptide (natural ANP) does not contain D-amino acids or D-amino acid residues. The terms "natural atrial natriuretic peptide (natural ANP)" or "natural A-type natriuretic peptide" or "natural ANP" or "natural ANP 1-28" are used interchangeably herein. In one embodiment, natural ANP1-28 comprises, consists of, or consists essentially of the amino acid sequence SLRRSSCFGGRMDRIGAQSGLGCNSFRY (SEQ ID NO: 11). In one embodiment, ANP 1-28 is amino acid sequence SLRRSSCFGGRMDRIGAQSGLGCNSFRY (SEQ ID NO: 11).

The term "natural C-type natriuretic peptide (natural CNP)" as used herein means naturally occurring C-type natriuretic peptide. Without being bound by theory, natural C-type natriuretic peptide is synthesized in nature, for example by a biological organism, using L-amino acids. In other words, natural C-type natriuretic peptide (natural CNP) does not contain D-amino acids or D-amino acid residues. The terms "natural C-type natriuretic peptide (natural CNP)" or "natural C-type natriuretic peptide" or "natural CNP" or "natural CNP 1-22" are used interchangeably herein. In one embodiment, natural CNP1-22 comprises, consists of, or consists essentially of the amino acid sequence GLSKGCFGLKLDRIGSMSGLGC (SEQ ID NO: 12). In one embodiment, CNP 1-22 is amino acid sequence GLSKGCFGLKLDRIGSMSGLGC (SEQ ID NO: 12).

The terms "natriuretic peptide" and "natural natriuretic peptide" have the same meaning and are used interchangeably herein.

The terms "Brain natriuretic peptide (BNP)" and "natural brain natriuretic peptide (natural BNP)" have the same meaning and are used interchangeably herein.

The terms "Atrial natriuretic peptide (ANP)" and "natural atrial natriuretic peptide (natural ANP)" have the same meaning and are used interchangeably herein.

The terms "C-type natriuretic peptide (CNP)" and "natural C-type natriuretic peptide (natural CNP)" have the same meaning and are used interchangeably herein.

The terms "BNP1-32" and "natural BNP1-32" have the same meaning and are used interchangeably herein.

The terms "ANP1-28" and "natural ANP1-28" have the same meaning and are used interchangeably herein.

The terms "CNP1-22" and "natural CNP1-22" have the same meaning and are used interchangeably herein.

The term "cleavable synthetic natriuretic peptide" as used herein means a natriuretic peptide that is artificially synthesized using L-amino acids. In other words, without being bound by theory, cleavable synthetic natriuretic peptides do not contain D-amino acids or D-amino acid residues. Cleavable synthetic natriuretic peptides are synthetic replicas of natural natriuretic peptides. Non-limiting examples of cleavable synthetic natriuretic peptides include cleavable synthetic brain natriuretic peptide (cleavable synthetic BNP), cleavable synthetic atrial natriuretic peptide (cleavable synthetic ANP), and cleavable synthetic C-type natriuretic peptide (cleavable synthetic CNP), or combinations thereof. Cleavable synthetic natriuretic peptides may also contain one or more glycine (Gly) amino acids (or glycine (Gly) amino acid residues).

The term "cleavable synthetic brain natriuretic peptide (cleavable synthetic BNP)" as used herein means brain natriuretic peptide that is artificially synthesized using L-amino acids. In other words, cleavable synthetic brain natriuretic peptide (BNP) does not contain D-amino acids or D-amino acid residues. Cleavable synthetic brain natriuretic peptide (cleavable synthetic BNP) is a synthetic replica of natural brain natriuretic peptide (natural BNP). The terms "cleavable synthetic brain natriuretic peptide (cleavable synthetic BNP)" or "cleavable synthetic B-type natriuretic peptide" or "cleavable synthetic BNP" are used interchangeably herein.

The term "cleavable synthetic atrial natriuretic peptide (ANP)" as used herein means atrial natriuretic peptide that is artificially synthesized using L-amino acids. In other words, cleavable synthetic atrial natriuretic peptide (ANP) does not contain D-amino acids or D-amino acid residues. Cleavable synthetic atrial natriuretic peptide (cleavable synthetic ANP) is a synthetic replica of natural atrial natriuretic peptide (natural ANP). The terms "cleavable synthetic atrial natriuretic peptide (cleavable synthetic ANP)" or "cleavable synthetic A-type natriuretic peptide" or "cleavable synthetic ANP" are used interchangeably herein.

The term "cleavable synthetic C-type natriuretic peptide (cleavable synthetic CNP)" as used herein means C-type natriuretic peptide that is artificially synthesized using L-amino acids. In other words, cleavable synthetic C-type natriuretic peptide (cleavable synthetic CNP) does not contain D-amino acids or D-amino acid residues. Cleavable synthetic C-type natriuretic peptide (cleavable synthetic CNP) is a synthetic replica of natural C-type natriuretic peptide (natural CNP). The terms "cleavable synthetic C-type natriuretic peptide" or "cleavable synthetic CNP" are used interchangeably herein.

The terms "endogenous L-natriuretic peptide" means an L-natriuretic peptide that is present in the sample at the point in time when the sample is obtained from the subject, and originates from the subject from which the sample was obtained. An example of an endogenous L-natriuretic peptide is a natural natriuretic peptide present in a plasma sample taken from a human subject.

The term "exogenous L-natriuretic peptide" means an L-natriuretic peptide that is added to a sample at a point in time after the sample was obtained from the subject and originates from an external source. Non-limiting examples of exogenous L-natriuretic peptides include natural natriuretic peptides and/or cleavable synthetic natriuretic peptides.

The terms "L-cleavage products" and "L-cleavage peptidoforms" and "L-natriuretic peptide cleavage products" have the same meaning and are used interchangeably herein. The term "L-cleavage peptidoform" means a peptide that is derived from an L-natriuretic peptide, wherein the L-cleavage peptidoform contains at least one fewer amino acid (or amino acid residue) than the L-natriuretic peptide from which it is derived. In a non-limiting example, an L-cleavage peptidoform is formed through contact of an L-natriuretic peptide with a protease.

As used herein the terms "cleavage products" and "L-cleavage products" have the same meaning and are used interchangeably herein.

In some embodiments, the length of the L-cleavage products of the natriuretic peptides is any one or more of 28-31, 25-30, 20-25, 25-32, 15-20, 10-15, 5-10, 10-20 or 20-30 amino acids long.

In some embodiments, the natriuretic peptide is BNP 1-32 and the L-cleavage products comprise any one or more of BNP 3-32, BNP 3-29, BNP 3-30, BNP 1-30, BNP 1-29, BNP 1-28, BNP 2-31, BNP 4-30, BNP 4-29, BNP 4-27, BNP 5-32, BNP 5-31, BNP 5-29, BNP 4-32, BNP 4-31, or combinations thereof, wherein each range indicates the amino acid position of mature BNP. For example, the full length mature BNP is 32 amino acids long and has amino acids 1-32. "BNP 3-29" refers to the proteolytic fragment of BNP that has amino acids 3-29 of the full length mature BNP. Similarly, "BNP 5-32" refers to the proteolytic fragment of BNP that has amino acids 5-32 of the full length mature BNP.

In some embodiments, the natriuretic peptide is BNP 1-32 and the L-cleavage products comprise BNP 3-32, BNP 3-29, BNP 3-30, BNP 1-30, BNP 5-29, BNP 4-29, BNP 1-28, BNP 1-29, BNP 4-31, BNP 4-32 or combinations thereof, wherein each range indicates the amino acid position of mature BNP.

In some embodiments, the natriuretic peptide is BNP 1-32 and the L-cleavage products comprise BNP 3-32, BNP 3-29, BNP 3-30, BNP 1-30, or combinations thereof, wherein each range indicates the amino acid position of mature BNP.

In some embodiments, the natriuretic peptide is BNP 1-32 and the L-cleavage products comprise BNP 3-32, or combinations thereof, wherein each range indicates the amino acid position of mature BNP.

TABLE 5

BNP 1-32 L-Cleavage Products

| L-Cleavage Product | SEQ ID NO. |
| --- | --- |
| BNP 3-32 | Amino acids 3-32 of SEQ ID NO: 7 |
| BNP 3-29 | Amino acids 3-29 of SEQ ID NO: 7 |
| BNP 3-30 | Amino acids 3-30 of SEQ ID NO: 7 |

TABLE 5-continued

BNP 1-32 L-Cleavage Products

| L-Cleavage Product | SEQ ID NO. |
| --- | --- |
| BNP 1-30 | Amino acids 1-30 of SEQ ID NO: 7 |
| BNP 1-29 | Amino acids 1-29 of SEQ ID NO: 7 |
| BNP 1-28 | Amino acids 1-28 of SEQ ID NO: 7 |
| BNP 2-31 | Amino acids 2-31 of SEQ ID NO: 7 |
| BNP 4-32 | Amino acids 4-32 of SEQ ID NO: 7 |
| BNP 4-31 | Amino acids 4-31 of SEQ ID NO: 7 |
| BNP 4-30 | Amino acids 4-30 of SEQ ID NO: 7 |
| BNP 4-29 | Amino acids 4-29 of SEQ ID NO: 7 |
| BNP 4-27 | Amino acids 4-27 of SEQ ID NO: 7 |
| BNP 5-32 | Amino acids 5-32 of SEQ ID NO: 7 |
| BNP 5-31 | Amino acids 5-31 of SEQ ID NO: 7 |
| BNP 5-29 | Amino acids 5-29 of SEQ ID NO: 7 |

In some embodiments, the natriuretic peptide is ANP 1-28 and the L-cleavage products comprise ANP 4-28, ANP 4-25, ANP 1-25, ANP 1-8, ANP 9-28, or combinations thereof, wherein each range indicates the amino acid position of mature ANP.

TABLE 6

ANP 1-28 L-Cleavage Products

| L-Cleavage Product | SEQ ID NO. |
| --- | --- |
| ANP 4-28 | Amino acids 4-28 of SEQ ID NO: 11 |
| ANP 4-25 | Amino acids 4-25 of SEQ ID NO: 11 |
| ANP 1-25 | Amino acids 1-25 of SEQ ID NO: 11 |
| ANP 1-8 | Amino acids 1-8 of SEQ ID NO: 11 |
| ANP 9-28 | Amino acids 9-28 of SEQ ID NO: 11 |

The term "L-peptidoform" and/or "L-peptidoforms" encompasses the parent L-peptidoform as well as its L-cleavage products (e.g., the parent natural natriuretic peptide as well as its cleavage peptidoforms, or the parent cleavable synthetic natriuretic peptide as well as its cleavage peptidoforms). A non-limiting example of the term "L-peptidoform" and/or "L-peptidoforms" encompasses the parent natural $BNP_{1-32}$ peptidoform as well as its cleavage peptidoforms. A non-limiting example of the term "L-peptidoform" and/or "L-peptidoforms" encompasses the parent cleavable synthetic $BNP_{1-32}$ peptidoform as well as its cleavage peptidoforms.

The term "L-amino acid" as used herein means a chiral amino acid in its L-enantiomeric form. The term "L-amino acid residue" as used herein means a chiral amino acid residue in its L-enantiomeric form.

The terms "L-enantiomeric form" or "L-enantiomer" or "L-form" have the same meaning and are used interchangeably herein.

The term "D-amino acid" as used herein means a chiral amino acid in its D-enantiomeric form. The term "D-amino acid residue" as used herein means a chiral amino acid residue in its D-enantiomeric form.

The terms "D-enantiomeric form" or "D-enantiomer" or "D-form" have the same meaning and are used interchangeably herein.

The term "non-natural natriuretic peptide" or "D-natriuretic peptide" or "non-cleavable synthetic natriuretic peptide" as used herein is an artificially synthesized natriuretic peptide comprising one or more D-amino acids (or D-amino acid residues). In general, without being bound by theory, non-natural natriuretic peptides are enantiomeric analogs of L-natriuretic peptides. Non-natural natriuretic peptides differ from their L-natriuretic peptide analogs in that one or more of the L-amino acids (or L-amino acid residues) in the L-natriuretic peptide is replaced with one or more D-amino acids (or D-amino acid residues). In some embodiments, all (or each) of the chiral amino acids (or chiral amino acid residues) in a non-natural natriuretic peptide are D-amino acids (or D-amino acid residues). The terms "non-natural natriuretic peptide" or "D-natriuretic peptide" or "non-cleavable synthetic natriuretic peptide" have the same meaning and are used interchangeably herein.

For example, without being bound by theory, one or more D-amino acids (or D-amino acid residues) may be located at any location or position in the amino acid sequence of the non-natural natriuretic peptide.

For example, without being bound by theory, one or more D-amino acids (or D-amino acid residues) may be located within a protease cleavage site motif of the non-natural natriuretic peptide. For example, in various embodiments, the present invention provides a non-natural natriuretic peptide comprising one or more protease cleavage site motifs, wherein the protease cleavage site motifs comprise an amino acid sequence motif, wherein the amino acid sequence motif comprises at least one D-amino acid (or D-amino acid residue). In some embodiments, the non-natural natriuretic peptide further comprises one or more additional amino acids (or amino acid residues), where the one or more amino acids (or amino acid residues) are selected from L-amino acids (or L-amino acid residues) and D-amino acids (or D-amino acid residues).

For example, without being bound by theory, one or more D-amino acids (or D-amino acid residues) may be located adjacent to a protease cleavage site motif of the non-natural natriuretic peptide. For example, in various embodiments, the present invention provides a non-natural natriuretic peptide comprising one or more protease cleavage site motifs; and one or more amino acids (or amino acid residues) adjacent to the protease cleavage site motif, wherein at least one of the amino acids (or amino acid residues) adjacent to the protease cleavage site motif is a D-amino acid (or D-amino acid residue). In some embodiments, at least one of the protease cleavage site motifs comprises an amino acid sequence motif, wherein the amino acid sequence motif comprises at least one D-amino acid (or D-amino acid residue). In some embodiments, the non-natural natriuretic peptide further comprises one or more additional amino acids (or amino acid residues), where the one or more amino acids (or amino acid residues) are selected from L-amino acids (or L-amino acid residues) and D-amino acids (or D-amino acid residues).

In general, without being bound by theory, non-natural natriuretic peptides are enantiomeric analogs of natural natriuretic peptides and/or cleavable synthetic natriuretic peptides. Non-natural natriuretic peptides differ from their natural natriuretic peptide analogs and/or cleavable synthetic natriuretic peptide analogs in that one or more of the L-amino acids (or L-amino acid residues) in the natural natriuretic peptide and/or cleavable synthetic natriuretic peptide is replaced with one or more D-amino acids (or D-amino acid residues).

For example, non-natural brain natriuretic peptide (non-natural BNP) is an enantiomeric analog of natural brain natriuretic peptide (natural BNP) and/or cleavable synthetic brain natriuretic peptide (cleavable synthetic BNP), wherein one or more of the L-amino acids (or L-amino acid residues) in the natural brain natriuretic peptide and/or cleavable synthetic brain natriuretic peptide is replaced with one or more D-amino acids (or D-amino acid residues). For example, non-natural atrial natriuretic peptide (non-natural ANP) is an enantiomeric analog of natural atrial natriuretic peptide (natural ANP) and/or cleavable synthetic atrial natriuretic peptide (cleavable synthetic ANP), wherein one or more of the L-amino acids (or L-amino acid residues) in the natural atrial natriuretic peptide and/or cleavable synthetic atrial natriuretic peptide is replaced with one or more D-amino acids (or D-amino acid residues). For example, non-natural C-type natriuretic peptide (non-natural CNP) is an enantiomeric analog of natural C-type natriuretic peptide (natural CNP) and/or cleavable synthetic C-type natriuretic peptide (cleavable synthetic CNP), wherein one or more of the L-amino acids (or L-amino acid residues) in the natural C-type natriuretic peptide and/or cleavable synthetic C-type natriuretic peptide is replaced with one or more D-amino acids (or D-amino acid residues).

Non-limiting examples of non-natural natriuretic peptides include non-natural brain natriuretic peptide (non-natural BNP), non-natural atrial natriuretic peptide (non-natural ANP), and non-natural C-type natriuretic peptide (non-natural CNP), or combinations thereof.

The term "non-natural natriuretic peptidoform" or "D-natriuretic peptidoform" or "non-cleavable synthetic natriuretic peptidoform" as used herein is an artificially synthesized natriuretic peptidoform comprising one or more D-amino acids (or D-amino acid residues). In general, without being bound by theory, non-natural natriuretic peptidoforms are enantiomeric analogs of L-peptidoforms. Non-natural natriuretic peptidoforms differ from their L-peptidoform analogs in that one or more of the L-amino acids (or L-amino acid residues) in the L-peptidoform is replaced with one or more D-amino acids (or D-amino acid residues). In general, without being bound by theory, non-natural natriuretic peptidoforms are enantiomeric analogs of natural natriuretic peptidoforms and/or cleavable synthetic natriuretic peptidoforms. Non-natural natriuretic peptidoforms differ from their natural natriuretic peptidoform analogs and/or cleavable synthetic natriuretic peptidoform analogs in that one or more of the L-amino acids (or L-amino acid residues) in the natural natriuretic peptidoform and/or cleavable synthetic natriuretic peptidoform is replaced with one or more D-amino acids (or D-amino acid residues). In some embodiments, all (or each) of the chiral amino acids (or chiral amino acid residues) in a non-natural natriuretic peptidoform are D-amino acids (or D-amino acid residues). In some embodiments the present invention provides a non-natural natriuretic peptidoform comprising a plurality of amino acids (or amino acid residues), wherein the amino acids (or amino acid residues) are selected from chiral amino acids (or chiral amino acid residues) and non-chiral amino acids (or non-chiral amino acid residues), wherein each chiral amino acid (or chiral amino acid residue) is a D-amino acid (or D-amino acid residue). In some embodiments, the non-chiral amino acid is glycine (Gly). In some embodiments, the non-chiral amino acid residue is a glycine (Gly) amino acid residue. In some embodiments, the non-chiral amino acid (or non-chiral amino acid residue) is glycine (Gly).

The term "non-natural cleavage products" or "non-natural cleavage peptidoforms" as used herein is an artificially synthesized cleavage peptidoform comprising one or more D-amino acids (or D-amino acid residues). Non-natural cleavage peptidoforms are artificially synthesized and are not produced biologically through cleavage of a non-natural natriuretic peptide by an enzyme (e.g., a protease). In general, without being bound by theory non-natural cleavage peptidoforms are enantiomeric analogs of L-cleavage peptidoforms derived from L-natriuretic peptides and/or L-peptidoforms. Non-natural cleavage peptidoforms differ from L-cleavage peptidoforms derived from L-natriuretic peptides and/or L-peptidoforms in that one or more L-amino acids (or L-amino acid residues) in the L-cleavage peptidoform derived from L-natriuretic peptides and/or L-peptidoforms is replaced with one or more D-amino acids (or D-amino acid residues). In general, without being bound by theory, non-natural cleavage peptidoforms are enantiomeric analogs of cleavage peptidoforms derived from natural natriuretic peptidoforms and/or cleavable synthetic natriuretic peptidoforms. Non-natural cleavage peptidoforms differ from cleavage peptidoforms derived from natural natriuretic peptidoforms and/or cleavable synthetic peptidoforms in that one or more L-amino acids (or L-amino acid residues) in the cleavage peptidoform derived from the natural natriuretic peptidoform and/or cleavable synthetic peptidoform is replaced with one or more D-amino acids (or D-amino acid residues). In some embodiments, all (or each) of the chiral amino acids (or chiral amino acid residues) in a non-natural cleavage peptidoform are D-amino acids (or D-amino acid residues). In some embodiments the present invention provides a non-natural cleavage peptidoform comprising a plurality of amino acids (or amino acid residues), wherein the amino acids (or amino acid residues) are selected from chiral amino acids (or chiral amino acid residues) and non-chiral amino acids (or non-chiral amino acid residues), wherein each chiral amino acid (or chiral amino acid residue) is a D-amino acid (or D-amino acid residue). In some embodiments, the non-chiral amino acid is glycine (Gly). In some embodiments, the non-chiral amino acid residue is a glycine (Gly) amino acid residue. In some embodiments, the non-chiral amino acid (or non-chiral amino acid residue) is glycine (Gly).

Amino acids may be referred to herein by either their commonly known three letter symbols or by the one-letter symbols recommended by the IUPAC-IUB.

As used herein the terms "one or more" and "at least one" are used interchangeably.

TABLE 7

SEQ ID NOs

| Sequence | SEQ ID NO |
|---|---|
| HPLG | 1 |
| LRAPR | 2 |
| SPKMVGSGCFCRKMDRISSSSGLCCKVLRRH | 3 |
| MDPQTAPSRALLLLLFLHLAFLGGRSHPLGSPGSASDLETSG LQEQRNHLQGKLSELQVEQTSLEPLQESPRPTGVWKSREVAT EGIRGHRKMVLYTLRAPRSPKMVQGSGCFGRKMDRISSSSGL GCKVLRRH | 4 |
| HPLGSPGSASDLETSGLQEQRNHLQGKLSELQVEQTSLEPLQ ESPRPTGVWKSREVATEGIRGHRKMVLYTLRAPRSPKMVQGS GCFGRKMDRISSSSGLGCKVLRRH | 5 |
| HPLGSPGSASDLETSGLQEQRNHLQGKLSELQVEQTSLEPLQ ESPRPTGVWKSREVATEGIRGHRKMVLYTLRAPR | 6 |
| SPKMVQGSGCFGRKMDRISSSSGLGCKVLRRH | 7 |
| KMVQGSGCFGRKMDRISSSSGLGCKVL | 8 |
| MSSFSTTTVSFLLLLAFQLLGQTRA | 9 |
| PEVPPWTGEVSPAQRDGGALGRGPWDSSDRSALLKSKL | 10 |

TABLE 7-continued

SEQ ID NOs

| Sequence | SEQ ID NO |
|---|---|
| SLRRSSCFGGRMDRIGAQSGLGCNSFRY | 11 |
| GLSKGCFGLKLDRIGSMSGLGC | 12 |

VARIOUS NON-LIMITING EMBODIMENTS OF THE INVENTION

An array of BNP precursors and cleavage products exist in blood in an equilibrium established by the rate at which precursors are produced and secreted, as well as the rate at which substrates are cleaved. The components of this equilibrium bind to receptors with unequal affinities, and the strength of the signaling cascades that they induce results from the collective sum of these unequal contributors. Assays that measure BNP are incapable of correctly measuring diverse BNP-like products and cannot analytically describe this equilibrium. As soon as plasma is sampled from a patient, the input of new BNP substrates ceases, but the activity of catabolic processes does not. This artificially skews the equilibrium. Secondly, analytical methods for BNP are either incapable of distinguishing between these peptidoforms, insufficiently sensitive, or both. The methods described herein bypass the sensitivity problem by spiking in excess BNP into plasma samples. The rate at which new BNP cleavage products appear over time is thus indicative of plasma peptidase activities. These activities are a fundamental component in establishing the aforementioned equilibrium, and therefore more directly related to maladaptive signaling in cardiovascular disease.

There is a controversy around which assay to use to monitor/assess heart failure and hemodynamic status of an individual. There are two clinical assays proNT and BNP. ProNT is a large fragment generated from the pre-hormone when BNP (32 amino acids), which is cleaved by a series of enzymes (neutral endopeptidase, dipeptidylpeptidase IV, and insulin degrading enzyme). BNP has been reported to be further cleaved in plasma. The inventors have built an assay that can provide a reliable measure of enzymatic activity which should better reflect the biological consequences of BNP-mediated signaling in cardiovascular disease. We can additionally monitor formation of two or more fragments of BNP. There are 2 major problems with existing methods: 1) BNP and NT-proBNP assays were developed and used in clinical lab for heart failure diagnosis. However, both of them are all antibody-based ELISA, and those antibodies cannot differentiate BNP, proBNP and their variants. So the measurement itself is not accurate. 2) Based on the inventors' studies, after blood collection, the enzymes are still active and keeping on digesting BNP. Unlike in vivo, the generation of BNP is stopped and the dynamic balance of BNP and its peptidoforms are changed before the test, so the current assay cannot tell the real status of patient by measuring unstable targets. Currently, there are no existing solutions to these problems. The inventors have identified unique peptides to the N- and C-terminus of BNP, such as BNP3-32, BNP 3-29 etc. This process maybe similar for the other natriuretic peptides (CNP and ANP) and similar enzymatic assays could be produced.

Our goal was to develop a mass spectrometry (MS) based method capable of identifying and profiling BNP cleavage peptidoforms formed in plasma samples, with a view to informing the degradation of intact BNP in plasma samples. In developing a technique that can account for BNP cleavage peptidoforms, we aimed to help clarify the extent to which BNP is degraded by endogenous factors in plasma with the ultimate goal of providing more accurate diagnostic and prognostic parameters for heart failure.

We identified several requirements and impediments to the development of such a method. First, in order to avoid skewing the proteolytic profile by disfavoring or outright elimination of potential peptidoforms during sample preparation, the method must almost certainly involve intact protein analysis. Second, since clinically useful BNP concentrations range between 100-400 pg/μL, we anticipated that the direct measurement of endogenous BNP cleavage peptidoforms would require analytical sensitivity into the low to sub-ng/μL range. Third, a method for endogenous BNP proteolytic profiling would have to achieve sufficient sensitivity and simultaneously overcome the inherently broad dynamic range of plasma, which often involves an enrichment step. Immunoprecipitation-based sample enrichment strategies represent the obvious approach, but these can also skew proteolytic profiles by disfavoring peptidoforms with altered epitopes. Furthermore, enrichment strategies and similarly complex sample preparation steps lengthen protocols and increase variance, and are unlikely to ultimately be adopted for routine clinical analyses.

In this study, we present an alternative approach for BNP proteolytic profiling based on using neutral-coated capillary electrophoresis with electrospray ionization in a single unit that is directly coupled to a mass spectrometry (CESI-MS), and that can measure individual BNP cleavage peptidoforms as they are generated over time in minimally processed plasma. In our approach, standard exogenous $BNP_{1-32}$ is pulsed into a plasma sample, where endogenous peptidases cleave $BNP_{1-32}$ into its peptidoforms, which are then detected and profiled over time. This reaction can proceed in a CE sample vial that can be sampled for analysis at any desired time interval. By integrating multisegment injection (MSI), where multiple samples are sequentially introduced into a single capillary for simultaneous analysis, our method allows for the parallel analysis of multiple plasma samples where successive CESI-MS runs providing a time course for BNP proteolytic profiling. Similarly, MSI can be used to produce a multi-point BNP proteolytic profile from one plasma sample across the protracted timeframe of a single CESI-MS run.

The methods described herein comprise adding recombinant intact BNP into patient serum/plasma, and utilize mass spectrometry to analyze the proteolysis profile or proteolytic profile of patients to establish a risk assessment method for cardiovascular diseases.

Provided herein is a method for assessing risk of cardiovascular disease in a subject in need thereof. The method includes obtaining a sample comprising one or more proteases from the subject; adding a quantity of one or more natriuretic peptides to the sample; determining the protease activity over time comprising quantifying cleavage products of the one or more natriuretic peptide over of time, wherein an increase in the one or more cleavage products over time is indicative of increased protease activity; and assessing the risk of cardiovascular disease. In one embodiment, the subject has increased risk of cardiovascular disease if the protease activity is increased over time relative to the reference sample. In another embodiment, the subject has a decreased risk of cardiovascular disease if the protease activity is decreased over time relative to the reference sample.

In various embodiments, the present invention provides a method for determining the risk of developing cardiovascular disease in a subject, comprising: obtaining a sample comprising one or more proteases from the subject; adding a quantity of one or more natriuretic peptides to the sample; measuring an amount of one or more cleavage products of the one or more natriuretic peptides over a period of time, wherein an increase in the amount of one or more cleavage products over the period of time is indicative of increased protease activity; determining that the subject has an increased risk of developing cardiovascular disease if the protease activity is increased over the period of time relative to a reference value; determining that the subject has a decreased risk of developing cardiovascular disease if the protease activity is decreased over the period of time relative to the reference value; and selecting a treatment for the subject if the increased risk of developing cardiovascular disease is determined. In some embodiments, the method further comprises measuring an amount of the one or more natriuretic peptides over a period of time.

Provided herein is a method for assessing risk of cardiovascular disease in a subject in need thereof. The method includes obtaining a sample comprising one or more proteases from the subject; adding a quantity of one or more natriuretic peptides to the sample; and determining the rate at which the cleavage products of the one or more natriuretic peptides appear over time. In various embodiments, the rate at which the cleavage products appear over time is indicative of the peptidase activity in the sample. In one embodiment, an increase in peptidase activity relative to reference value is indicative of increased likelihood of cardiovascular disease.

In various embodiments, the present invention provides a method for determining the risk of developing cardiovascular disease in a subject, comprising: obtaining a sample comprising one or more proteases from the subject; adding a quantity of one or more natriuretic peptides to the sample; measuring a rate at which one or more cleavage products of the one or more natriuretic peptides is detected over a period of time, wherein an increase in the rate at which the one or more cleavage products is detected over the period of time is indicative of increased protease activity; determining that the subject has an increased risk of developing cardiovascular disease if the protease activity is increased over the period of time relative to a reference value; determining that the subject has a decreased risk of developing cardiovascular disease if the protease activity is decreased over the period of time relative to the reference value; and selecting a treatment for the subject if the increased risk of developing cardiovascular disease is determined.

In various embodiments, the present invention provides a method for treating a subject at risk of developing cardiovascular disease, comprising: obtaining a sample comprising one or more proteases from the subject; adding a quantity of one or more natriuretic peptides to the sample; measuring an amount of one or more cleavage products of the one or more natriuretic peptides over a period of time, wherein an increase in the amount of one or more cleavage products over the period of time is indicative of increased protease activity; determining that the subject has an increased risk of developing cardiovascular disease if the protease activity is increased over the period of time relative to a reference value; determining that the subject has a decreased risk of developing cardiovascular disease if the protease activity is decreased over the period of time relative to the reference value; and treating the subject having increased protease activity to reduce the risk of developing cardiovascular disease.

In various embodiments, the present invention provides a method of obtaining a proteolytic profile of one or more cleavage products of one or more natriuretic peptides for a subject, the method comprising: obtaining a sample comprising one or more proteases from the subject; adding a quantity of one or more natriuretic peptides to the sample; and measuring an amount of the one or more cleavage products of the one or more natriuretic peptides over a period of time to obtain the proteolytic profile of the subject.

In various embodiments, the present invention provides a method of obtaining a proteolytic profile for a subject, the method comprising: obtaining one or more samples from the subject, each sample comprising one or more proteases; adding a quantity of one or more natriuretic peptides to each sample; measuring or quantifying the amount of the one or more natriuretic peptides in each sample over a period of time; and measuring or quantifying an amount of one or more cleavage products of the one or more natriuretic peptides in each sample over the period of time to obtain the proteolytic profile of the subject. In some embodiments, the measuring or quantifying of each sample is performed simultaneously. In some embodiments, the measuring or quantifying of each sample is performed sequentially. In some embodiments, the one or more samples is 1-2, 1-3, 1-4, 1 to 5, 2-3, 2-4, 2-5, 3-4, 3-5 or 4-5.

In various embodiments, the present invention provides a method of obtaining a proteolytic profile for a subject, the method comprising: obtaining a sample comprising one or more proteases from the subject; adding a quantity of one or more natriuretic peptides to the sample; measuring or quantifying the amount of the one or more natriuretic peptides over a period of time; and measuring or quantifying an amount of one or more cleavage products of the one or more natriuretic peptides over the period of time to obtain the proteolytic profile of the subject. In another embodiment, wherein a sample is one sample.

In various embodiments, the present invention provides a method of obtaining a proteolytic profile for a subject, the method comprising: obtaining a sample comprising one or more proteases from the subject; adding a quantity of one or more natriuretic peptides to the sample; measuring the amount of the one or more natriuretic peptides over a period of time; and measuring an amount of the one or more cleavage products of the one or more natriuretic peptides over the period of time to obtain the proteolytic profile of the subject. In some embodiments, the method further comprises comparing the proteolytic profile from the subject to a proteolytic profile from a reference sample. In some embodiments, the method further comprises making an assessment of the subject based on the comparison, wherein the assessment is a diagnosis of a cardiovascular disease. In some embodiments, the method further comprises treating the subject based on the assessment. In some embodiments, the method further comprises treating the subject for the cardiovascular disease based on the assessment.

In various embodiments, the present invention provides a method of obtaining a proteolytic profile for a subject, the method comprising: obtaining a sample comprising one or more proteases from the subject; adding a quantity of one or more natriuretic peptides to the sample; measuring the amount of the one or more natriuretic peptides over a period of time; and measuring an amount of the one or more cleavage products of the one or more natriuretic peptides over the period of time to obtain the proteolytic profile of the subject. In some embodiments, the method further comprises comparing the proteolytic profile from the subject to a proteolytic profile from a reference sample. In some embodiments, the method further comprises making an assessment of the subject based on the comparison, wherein the assessment is a prognosis of developing a cardiovascular disease. In some embodiments, the method further comprises treating the subject based on the assessment.

In various embodiments, the present invention provides a method of obtaining a proteolytic profile for a subject, the method comprising: obtaining a sample comprising one or more proteases from the subject; adding a quantity of one or more natriuretic peptides to the sample; measuring the amount of the one or more natriuretic peptides over a period of time; and measuring an amount of the one or more cleavage products of the one or more natriuretic peptides over the period of time to obtain the proteolytic profile of the subject. In some embodiments, the method further comprises comparing the proteolytic profile from the subject to a proteolytic profile from a reference sample, wherein a difference between the proteolytic profile of the subject and the proteolytic profile of the reference sample is indicative of a cardiovascular disease.

In various embodiments, the present invention provides a method of obtaining a proteolytic profile for a subject, the method comprising: obtaining a sample comprising one or more proteases from the subject; adding a quantity of one or more natriuretic peptides to the sample; measuring the amount of the one or more natriuretic peptides over a period of time; and measuring an amount of the one or more cleavage products of the one or more natriuretic peptides over the period of time to obtain the proteolytic profile of the subject. In some embodiments, the method further comprises comparing the proteolytic profile from the subject to a proteolytic profile from a reference sample, wherein a difference between the proteolytic profile of the subject and the proteolytic profile of the reference sample is an assessment of the subject, wherein the assessment is a diagnosis of a cardiovascular disease. In some embodiments, the method further comprises treating the subject based on the assessment. In some embodiments, the method further comprises treating the subject for the cardiovascular disease based on the assessment.

In various embodiments, the present invention provides a method of obtaining a proteolytic profile for a subject, the method comprising: obtaining a sample comprising one or more proteases from the subject; adding a quantity of one or more natriuretic peptides to the sample; measuring the amount of the one or more natriuretic peptides over a period of time; and measuring an amount of the one or more cleavage products of the one or more natriuretic peptides over the period of time to obtain the proteolytic profile of the subject. In some embodiments, the method further comprises comparing the proteolytic profile from the subject to a proteolytic profile from a reference sample, wherein a difference between the proteolytic profile of the subject and the proteolytic profile of the reference sample is an assessment of the subject, wherein the assessment is a prognosis of developing a cardiovascular disease. In some embodiments, the method further comprises treating the subject based on the assessment.

In various embodiments, the present invention provides a method of obtaining a proteolytic profile for a subject, the method comprising: obtaining a sample comprising one or more proteases from the subject; adding a quantity of one or more natriuretic peptides to the sample; measuring the amount of the one or more natriuretic peptides over a period of time; and measuring an amount of the one or more cleavage products of the one or more natriuretic peptides over the period of time to obtain the proteolytic profile of the subject. In some embodiments, the method further comprises making an assessment of the subject based on the proteolytic profile, wherein the assessment is a diagnosis of a cardiovascular disease. In some embodiments, the method further comprises treating the subject based on the assessment. In some embodiments, the method further comprises making an assessment of the subject based on the proteolytic profile, wherein the assessment is a diagnosis of a cardiovascular disease; and treating the subject based on the assessment.

In various embodiments, the present invention provides a method of obtaining a proteolytic profile for a subject, the method comprising: obtaining a sample comprising one or more proteases from the subject; adding a quantity of one or more natriuretic peptides to the sample; measuring the amount of the one or more natriuretic peptides over a period of time; and measuring an amount of the one or more cleavage products of the one or more natriuretic peptides over the period of time to obtain the proteolytic profile of the subject. In some embodiments, the method further comprises making an assessment of the subject based on the proteolytic profile, wherein the assessment is a prognosis of developing a cardiovascular disease. In some embodiments, the method further comprises treating the subject based on the assessment. In some embodiments, the method further comprises making an assessment of the subject based on the proteolytic profile, wherein the assessment is a prognosis of developing a cardiovascular disease; and treating the subject based on the assessment.

In various embodiments, the present invention provides a method for assessing the efficacy of a treatment, comprising: comparing a proteolytic profile from a subject to a proteolytic profile from a reference sample, wherein a change in the proteolytic profile from the subject relative to the proteolytic profile from the reference sample is indicative of the efficacy of the treatment.

In various embodiments, the present invention provides a method for assessing the efficacy of a treatment, comprising: comparing the one or more cleavage products of the one or more natriuretic peptides from a subject to the one or more cleavage products of the one or more natriuretic peptides from a reference sample, wherein a change in the one or more cleavage products from the subject relative to the one or more cleavage products from the reference sample is indicative of the efficacy of the treatment.

In some embodiments of the present invention, the reference sample is obtained from a control subject, wherein the control subject does not have a cardiovascular disease. In some embodiments of the present invention, the reference sample is obtained from the subject before the subject is treated for a cardiovascular disease. In some embodiments of the present invention, the reference sample is from a subject that has been treated for a cardiovascular disease. In some embodiments of the present invention, the reference sample is obtained from the subject at an earlier time point.

In various embodiments the present invention provides a method, for determining the risk of developing cardiovascular disease in a subject, comprising: obtaining a biological sample comprising one or more proteases from the subject; adding a quantity of one or more natriuretic peptides to the biological sample; and detecting the presence of one or more cleavage products of the one or more natriuretic peptides over a period of time, wherein the presence of one or more cleavage products is indicative of an increased risk of the subject developing cardiovascular disease.

In various embodiments, assessing the risk of cardiovascular disease in a subject is determining the likelihood of a subject developing cardiovascular diseases. In exemplary embodiments, the cardiovascular disease is heart failure, arterial fibrillation or combination thereof. Specifically, in various embodiments, the invention may provide prognostic or diagnostic information pertaining to categorization of heart failure, for example classification between heart failure with reduced ejection fraction or heart failure with preserved ejection fraction.

In some embodiments, the natriuretic peptides are any one or more of Brain natriuretic peptide (BNP), Atrial natriuretic peptide (ANP), C-type natriuretic peptide (CNP) or combinations thereof. In some embodiments, the natriuretic peptide is Brain natriuretic peptide (BNP).

In exemplary embodiments, the proteases are circulating proteases. In exemplary embodiments, the proteases are any one or more of neutral endopeptidase, dipeptidylpeptidase IV, insulin degrading enzyme or combination thereof.

In some embodiments, the sample is a biological sample. In some embodiments the sample is plasma, blood, or serum. In some embodiments, the sample is plasma. In some embodiments, the biological sample is plasma, blood, or serum. In some embodiments, the biological sample is plasma.

In exemplary embodiments, the quantity of one or more natriuretic peptides added to the sample is any one or more of about 10 ng/µL, 50 ng/µL, 75 ng/µL, 100 ng/µL, 125 ng/µL, 150 ng/µL, 175 ng/µL, 200 ng/µL, 225 ng/µL, 250 ng/µL, 275 ng/µL, 300 ng/µL, 350 ng/µL, 375 ng/µL, 400 ng/µL, 450 ng/µL, 475 ng/µL, 500 ng/µL or combinations thereof. In some embodiments, the quantity of one or more natriuretic peptides added to the sample is any one or more of about 50 ng/µL, 75 ng/µL, 100 ng/µL, 125 ng/µL, 150 ng/µL, 175 ng/µL, 200 ng/µL, 225 ng/µL, 250 ng/µL or combinations thereof. In some embodiments, the natriuretic peptide is BNP and is added in amounts described herein. The optimum amount of the natriuretic peptide to be added to the sample will be apparent to a person of skill in the art.

In exemplary embodiments, the time period over which the protease activity is determined is about 1 hour in any one or more of 1, 5, 10, 15, 20, 25 or 30 min intervals, about 2 hours in any one or more of 1, 5, 10, 15, 20, 25, 30, 40, 50 or 60 min intervals, about 3 hours in any one or more of 1, 5, 10, 15, 20, 25, 30, 40, 50, 60, 75 or 90 min intervals, about 4 hours in any one or more of 1, 5, 10, 15, 20, 25, 30, 40, 50, 60, 75, 90, 100, 110 or 120 min intervals or combinations thereof. The optimum time period will be apparent to a person of skill in the art. In some embodiments, the time period is less than 1 hour. In some embodiments, the time period is less than or equal to 1 hour. In some embodiments, the time period is about 1 hour. In some embodiments, the time period is about 2 hours. In some embodiments, the time period is about 14 hours. In some embodiments, the time period is about 15 hours. In some embodiments, the time period is up to 1 hour. In some embodiments, the time period is up to 14 hours. In some embodiments the time period is greater than 1 hour. In some embodiments, the time period is greater than 14 hours. In some embodiments, the time period is 0.5 hours to 24 hours. In some embodiments, the time period is 0.5 hours to 20 hours. In some embodiments, the time period is 0.5 hours to 15 hours.

In some embodiments, the length of the cleavage products of the natriuretic peptides is any one or more of 28-31, 25-30, 20-25, 25-32, 15-20, 10-15, 5-10, 10-20 or 20-30 amino acids long.

In some embodiments, the natriuretic peptide is BNP 1-32 and the cleavage products comprise any one or more of BNP 3-32, BNP 3-29, BNP 3-30, BNP 1-30, BNP 1-29, BNP 1-28, BNP 2-31, BNP 4-30, BNP 4-29, BNP 4-27, BNP 5-32, BNP 5-31, BNP 5-29, BNP 4-32, BNP 4-31, or combinations thereof, wherein each range indicates the amino acid position of mature BNP. For example, the full length mature BNP is 32 amino acids long and has amino acids 1-32. "BNP 3-29" refers to the proteolytic fragment of BNP that has amino acids 3-29 of the full length mature BNP. Similarly, "BNP 5-32" refers to the proteolytic fragment of BNP that has amino acids 5-32 of the full length mature BNP.

In some embodiments, the natriuretic peptide is BNP 1-32 and the cleavage products comprise BNP 3-32, BNP 3-29, BNP 3-30, BNP 1-30, BNP 5-29, BNP 4-29, BNP 1-28, BNP 1-29, BNP 4-31, BNP 4-32 or combinations thereof, wherein each range indicates the amino acid position of mature BNP.

In some embodiments, the natriuretic peptide is BNP 1-32 and the cleavage products comprise BNP 3-32, BNP 3-29, BNP 3-30, BNP 1-30, or combinations thereof, wherein each range indicates the amino acid position of mature BNP.

In some embodiments, the natriuretic peptide is BNP 1-32 and the cleavage products comprise BNP 3-32, or combinations thereof, wherein each range indicates the amino acid position of mature BNP.

TABLE 8

BNP 1-32 Cleavage Products

| Cleavage Product | SEQ ID NO. |
| --- | --- |
| BNP 3-32 | Amino acids 3-32 of SEQ ID NO: 7 |
| BNP 3-29 | Amino acids 3-29 of SEQ ID NO: 7 |
| BNP 3-30 | Amino acids 3-30 of SEQ ID NO: 7 |
| BNP 1-30 | Amino acids 1-30 of SEQ ID NO: 7 |
| BNP 1-29 | Amino acids 1-29 of SEQ ID NO: 7 |
| BNP 1-28 | Amino acids 1-28 of SEQ ID NO: 7 |
| BNP 2-31 | Amino acids 2-31 of SEQ ID NO: 7 |
| BNP 4-32 | Amino acids 4-32 of SEQ ID NO: 7 |
| BNP 4-31 | Amino acids 4-31 of SEQ ID NO: 7 |
| BNP 4-30 | Amino acids 4-30 of SEQ ID NO: 7 |
| BNP 4-29 | Amino acids 4-29 of SEQ ID NO: 7 |
| BNP 4-27 | Amino acids 4-27 of SEQ ID NO: 7 |
| BNP 5-32 | Amino acids 5-32 of SEQ ID NO: 7 |
| BNP 5-31 | Amino acids 5-31 of SEQ ID NO: 7 |
| BNP 5-29 | Amino acids 5-29 of SEQ ID NO: 7 |

In some embodiments, the cleavage products are not modified. In some embodiments, the cleavage products are modified. In some embodiments, the cleavage products are oxidated at methionine residues. Additional examples of modifications may be found at www.unimod.org. In some embodiments, the cleavage products of BNP are not modified. In some embodiments, the cleavage products of BNP are modified. In an exemplary embodiment, the cleavage product of BNP is oxidized at one or more methionine residues.

In some embodiments, the cleavage products are measured or quantified or detected using any one or more of capillary electrophoresis/electrospray ionization-mass spectrometry (CESI-MS), capillary electrophoresis-mass spectrometry (CE-MS), liquid chromatography mass spectrometry (LC-MS), high pressure liquid chromatography mass spectrometry (HPLC-MS), or combinations thereof. In some embodiments, the cleavage products are measured or quantified or detected using capillary electrophoresis-mass spectrometry (CE-MS). In some embodiments, the cleavage products are measured or quantified or detected using capillary electrophoresis/electrospray ionization-mass spectrometry (CESI-MS). In some embodiments, the cleavage products are measured or quantified or detected using capillary electrophoresis/electrospray ionization-mass spectrometry (CESI-MS) combined with multi-segment injection (MSI).

In some embodiments, the cleavage products are measured or quantified or detected using a mass spectrometer and a mass spectrometry method. In some embodiments, the mass spectrometry method comprises any one or more of capillary electrophoresis/electrospray ionization-mass spectrometry (CESI-MS), capillary electrophoresis-mass spectrometry (CE-MS), liquid chromatography mass spectrometry (LC-MS), high pressure liquid chromatography mass spectrometry (HPLC-MS), or combinations thereof. In some embodiments, mass spectrometry data is obtained from the mass spectrometer using the mass spectrometry method.

In some embodiments, the cleavage products are measured or quantified or detected using a method comprising any one or more of capillary electrophoresis/electrospray ionization-mass spectrometry (CESI-MS), capillary electrophoresis-mass spectrometry (CE-MS), liquid chromatography mass spectrometry (LC-MS), high pressure liquid chromatography mass spectrometry (HPLC-MS), or combinations thereof. In some embodiments, the cleavage products are measured or quantified or detected using a method comprising capillary electrophoresis-mass spectrometry (CE-MS). In some embodiments, the cleavage products are measured or quantified or detected using a method comprising capillary electrophoresis/electrospray ionization-mass spectrometry (CESI-MS). In some embodiments, the cleavage products are measured or quantified or detected using a method comprising capillary electrophoresis/electrospray ionization-mass spectrometry (CESI-MS) combined with multisegment injection (MSI).

In various embodiments, the cleavage products are measured or quantified or detected using a method comprising capillary electrophoresis/electrospray ionization-mass spectrometry (CESI-MS) combined with multisegment injection (MSI). In some embodiments, the method further comprises electrokinetic sample injection. In some embodiments, the method further comprises using one or more neutral-coated CESI capillaries.

In some embodiments, the reference value is the protease activity over time in a sample obtained from a healthy subject. In some embodiments, the reference value is the protease activity over time in a sample obtained from a subject that has been treated for cardiovascular disease. In further embodiments, the reference value is the protease activity over time in a sample obtained from the subject at an earlier time point. In some embodiments, the protease activity in a subject having or suspected of having cardiovascular disease is compared to the reference value is increased by at least or about 10%, 20%, 30%, 40%, 50%, 60%, 70%, 80%, 90% or 100%. In some embodiments, the protease activity in a subject having or suspected of having cardiovascular disease is compared to the reference value is increased by at least or about 1-fold, 2-fold, 3-fold, 4-fold, 5-fold, 10-fold, 15-fold, 20-fold, 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, 100-fold or a combination thereof.

ADDITIONAL NON-LIMITING EMBODIMENTS OF THE INVENTION

The absence of tools and methods capable of accurately and reproducibly quantifying concentrations of BNP and BNP cleavage peptidoforms (e.g., endogenous BNP and cleavage peptidoforms derived therefrom, natural BNP and cleavage peptidoforms derived therefrom, and cleavable synthetic BNP and cleavage peptidoforms derived therefrom) is a problem that obscures clinically important functional differences. As plasma BNP analysis is currently used in the diagnosis of heart failure, endogenous BNP levels and the profiles of its cleavage peptidoforms (either at a given time point or over a defined time period) is relevant for diagnostic and prognostic insights into various diseases and disorders and various research endeavors.

Without being bound by theory, one tool commonly used in various analytical methods for obtaining more accurate quantification data of chemical species of interest in a sample is an internal standard. Ideally, the internal standard is a compound or chemical substance that is very similar, but not identical to the chemical species of interest in the sample. Moreover, an internal standard used needs to provide a signal that is similar to the chemical species of interest in most ways, but sufficiently different so that the two signals are also readily distinguishable by the analytical method and/or testing equipment. One of skill in the art would be familiar with the concept of internal standards and their use.

Unfortunately, natural natriuretic peptides (e.g., natural BNP) and cleavage peptidoforms derived therefrom, and cleavable synthetic natriuretic peptides (e.g., cleavable synthetic BNP) and cleavage peptidoforms derived therefrom are not suitable for use as internal standards for natriuretic peptide analysis in biological samples (e.g., blood, whole blood, plasma, serum, or body fluid) because these peptides and their cleavage peptidoforms undergo robust and dynamic enzyme-mediated cleavage by various enzymes endogenous in the biological sample.

As is known to one of skill in the art, isotopically labeled analogs of any target represent the analytical gold-standard of internal standards. Unfortunately, isotopically labeled analogs of natural natriuretic peptides and cleavage peptidoforms derived therefrom, and isotopically labeled analogs of cleavable synthetic natriuretic peptides and cleavage peptidoforms derived therefrom, are also susceptible to enzymatic degradation by endogenous enzymes and therefore are not suitable for use as internal standards for natriuretic peptide analysis in biological samples. In some embodiments, the L-natriuretic peptide (e.g., natural natriuretic peptide and/or cleavable synthetic natriuretic peptide) is isotopically labeled with a stable isotope. In some embodiments, the L-natriuretic peptide (e.g., natural natriuretic peptide and/or cleavable synthetic natriuretic peptide) is not isotopically labeled with a stable isotope.

To overcome these limitations, the inventors conceived and developed various non-natural natriuretic peptides, wherein the non-natural natriuretic peptides comprise one or more D-amino acids or D-amino acid residues. In comparison to their L-natriuretic peptide, natural natriuretic peptide and cleavable synthetic natriuretic peptide analogs, the non-natural natriuretic peptides of the invention, in various embodiments, are not susceptible to enzyme-mediated cleavage, for example by an enzyme(s) endogenous in the biological sample (e.g., a protease). Therefore, without being bound by theory, since enzyme substrate recognition is stereospecific, non-natural natriuretic peptides comprising one or more D-amino acids (or D-amino acid residues) (e.g., non-natural BNP) will not be recognized by an enzyme(s) endogenous in the biological sample (e.g., enzyme(s) endogenous to a plasma sample, for example a protease) and the non-natural natriuretic peptide will remain intact and stable when added to a biological sample (e.g., a plasma sample). Without being bound by theory, this resistance to enzymatic degradation makes the non-natural natriuretic peptides of the invention ideal for use as internal standards in natriuretic peptide analysis in biological samples. In some embodiments, the non-natural natriuretic peptides of the invention may be used as internal standards in various methods described herein for the diagnosis and/or prognosis of various diseases. In various embodiments, the one or more D-amino acids (or D-amino acid residues) can be incorporated throughout the non-natural natriuretic peptide or at any specifically targeted location along the peptide sequence.

As such, in one non-limiting example, a non-natural natriuretic peptide (e.g., non-natural BNP) could be used as an internal standard for quantitative MS-based profiling of one or more endogenous natriuretic peptides (e.g., endogenous BNP) in a biological sample (e.g., human blood, mammalian blood, plasma, serum, or body fluid). For example, without being bound by theory, the use of a non-natural natriuretic peptide as an internal standard would enable the comparison of natriuretic peptide cleavage profiles (e.g., BNP-cleavage profiles, L-natriuretic peptide cleavage profiles) between one or more patients. Moreover, the use of a non-natural natriuretic peptide (e.g., non-natural BNP) as an internal standard in MS-based profiling of one or more endogenous natriuretic peptides (e.g., a natural natriuretic peptide) could be used in the diagnosis and/or prognosis of various diseases (e.g., cardiovascular disease, heart transplant disease, kidney diseases, etc.).

In another non-limiting example, a non-natural natriuretic peptide (e.g., non-natural BNP) could be used as an internal standard for quantitative MS-based profiling of one or more L-natriuretic peptides added to a biological sample (e.g., human blood, mammalian blood, plasma, serum, or body fluid). For example, without being bound by theory, the use of a non-natural natriuretic peptide as an internal standard would enable the comparison of L-natriuretic peptide cleavage profiles (e.g., L-BNP cleavage profiles) between one or more patients. Moreover, the use of a non-natural natriuretic peptide (e.g., non-natural BNP) as an internal standard in MS-based profiling of one or more of one or more L-natriuretic peptides added to a sample (e.g. an exogenous L-natriuretic peptide) could be used in the diagnosis and/or prognosis of various diseases (e.g., cardiovascular disease, heart transplant disease, kidney diseases, etc.).

In various embodiments, the present invention provides a non-natural natriuretic peptide. In some embodiments, the non-natural natriuretic peptide comprises one or more D-amino acids (or D-amino acid residues). In some embodiments, at least one of the D-amino acids (or D-amino acid residues) is isotopically labeled. In some embodiments, at least one of the D-amino acids (or D-amino acid residues) is not isotopically labeled. In some embodiments, the non-natural natriuretic peptides are not susceptible to enzyme-mediated cleavage, for example by an enzyme(s) endogenous in the biological sample (e.g., a protease).

In various embodiments, the present invention provides a non-natural natriuretic peptide comprising one or more D-amino acids. In various embodiments, the present invention provides a non-natural natriuretic peptide comprising one or more D-amino acid residues. In various embodiments, the present invention provides a non-natural natriuretic peptide comprising one or more D-amino acids (or D-amino acid residues), wherein at least one of D-amino acids (or D-amino acid residues) is isotopically labeled. In some embodiments, the D-amino acids (or D-amino acid residues) are not isotopically labeled. In some embodiments, the non-natural natriuretic peptides are not susceptible to enzyme-mediated cleavage, for example by an enzyme(s) endogenous in the biological sample (e.g., a protease).

In various embodiments, the present invention provides a non-natural natriuretic peptide comprising one or more L-amino acids (or L-amino acid residues); and one or more D-amino-acids (or D-amino acid residues). In some embodiments, at least one of the L-amino acids (or L-amino acid residues) is isotopically labeled. In some embodiments, the L-amino acids (or L-amino acid residues) are not isotopically labeled. In some embodiments, at least one of the D-amino acids (or D-amino acid residues) is isotopically labeled. In some embodiments, the D-amino acids (or D-amino acid residues) are not isotopically labeled. In some embodiments, the non-natural natriuretic peptides are not susceptible to enzyme-mediated cleavage, for example by an enzyme(s) endogenous in the biological sample (e.g., a protease).

In various embodiments, the present invention provides a non-natural natriuretic peptide comprising a plurality of amino acids (or amino acid residues), wherein one or more amino acid (or amino acid residue) is a D-amino acid (or D-amino acid residue). In some embodiments, at least one of the D-amino acids (or D-amino acid residues) is isotopically labeled. In some embodiments, the D-amino acids (or D-amino acid residues) are not isotopically labeled. In some embodiments, the non-natural natriuretic peptides are not susceptible to enzyme-mediated cleavage, for example by an enzyme(s) endogenous in the biological sample (e.g., a protease).

In various embodiments, the present invention provides a non-natural natriuretic peptide comprising a plurality of amino acids (or amino acid residues), wherein one or more amino acid (or amino acid residue) is a L-amino acid (or L-amino acid residue); and one or more amino acid (or amino acid residue) is a D-amino acid (or D-amino acid residue). In some embodiments, at least one of the L-amino acids (or L-amino acid residues) is isotopically labeled. In some embodiments, the L-amino acids (or L-amino acid residues) are not isotopically labeled. In some embodiments, at least one of the D-amino acids (or D-amino acid residues) is isotopically labeled. In some embodiments, the D-amino acids (or D-amino acid residues) is not isotopically labeled. In some embodiments, the non-natural natriuretic peptides are not susceptible to enzyme-mediated cleavage, for example by an enzyme(s) endogenous in the biological sample (e.g., a protease). In some embodiments, the present invention provides a non-natural natriuretic peptide comprising a plurality of amino acids (or amino acid residues), wherein the plurality of amino acids (or amino acid residues) are selected from chiral amino acids (or chiral amino acid residues) and non-chiral amino acids (or non-chiral amino acid residues). In some embodiments, the non-chiral amino acid is glycine (Gly). In some embodiments, the non-chiral amino acid residue is a glycine (Gly) amino acid residue. In some embodiments, the non-chiral amino acid (or non-chiral amino acid residue) is glycine (Gly).

In various embodiments, the present invention provides a non-natural natriuretic peptide comprising a plurality of amino acids (or amino acid residues), wherein the amino acids (or amino acid residues) are selected from chiral amino acids (or chiral amino acid residues) and non-chiral amino acids (or non-chiral amino acid residues), wherein each chiral amino acid (or chiral amino acid residue) is a D-amino acid (or D-amino acid residue). In some embodiments, at least one of the D-amino acids (or D-amino acid residues) is isotopically labeled. In some embodiments, the D-amino acids (or D-amino acid residues) are not isotopically labeled. In some embodiments, the non-natural natriuretic peptides are not susceptible to enzyme-mediated cleavage, for example by an enzyme(s) endogenous in the biological sample (e.g., a protease). In some embodiments, the non-chiral amino acid is glycine (Gly). In some embodiments, the non-chiral amino acid residue is a glycine (Gly) amino acid residue. In some embodiments, the non-chiral amino acid (or non-chiral amino acid residue) is glycine (Gly).

In various embodiments, the present invention provides a non-natural cleavage peptidoform. In some embodiments, the non-natural cleavage peptidoform comprises one or more D-amino acids (or D-amino acid residues). In some embodiments, at least one D-amino acid (or D-amino acid residue) is isotopically labeled. In some embodiments, the D-amino acids (or D-amino acid residues) are not isotopically labeled. In some embodiments, the non-natural cleavage peptidoform is not susceptible to enzyme-mediated cleavage, for example by an enzyme(s) endogenous in the biological sample (e.g., a protease). In some embodiments, the non-natural natriuretic peptide is artificially synthesized.

In various embodiments, the present invention provides a non-natural cleavage peptidoform. In some embodiments, the non-natural cleavage peptidoform comprises one or more D-amino acids (or D-amino acid residues); and one or more L-amino acids (or L-amino acid residues). In some embodiments, at least one D-amino acid (or D-amino acid residue) is isotopically labeled. In some embodiments, the D-amino acids (or D-amino acid residues) are not isotopically labeled. In some embodiments, at least one L-amino acid (or L-amino acid residue) is isotopically labeled. In some embodiments, the L-amino acids (or L-amino acid residues) is not isotopically labeled. In some embodiments, the non-natural cleavage peptidoform is not susceptible to enzyme-mediated cleavage, for example by an enzyme(s) endogenous in the biological sample (e.g., a protease). In some embodiments, the non-natural natriuretic peptide is artificially synthesized. In various embodiments, the present invention provides a non-natural cleavage peptidoform, comprising a plurality of amino acids (or amino acid residues). In some embodiments, the amino acids (or amino acid residues) are selected from chiral amino acids (or chiral amino acid residues) and non-chiral amino acids (or non-chiral amino acid residues).

In various embodiments, the non-natural natriuretic peptides of the invention are a therapeutic. For example, in various embodiments, the non-natural natriuretic peptides of the invention are supplementary drug delivery molecules or complementary drug delivery molecules. In some embodiments, the non-natural natriuretic peptide comprises one or more D-amino acids (or D-amino acid residues). In some embodiments, the non-natural natriuretic peptide further comprises one or more L-amino acids (or L-amino acid residues).

In various embodiments, the present invention provides a pharmaceutical composition comprising: one or more non-natural natriuretic peptides; and a pharmaceutically acceptable carrier. In some embodiments, the non-natural natriuretic peptide comprises one or more D-amino acids (or D-amino acid residues). In some embodiments, the non-natural natriuretic peptide further comprises one or more L-amino acids (or L-amino acid residues). In some embodiments, at least one of the D-amino acids (or D-amino acid residues) is isotopically labeled. In some embodiments, the D-amino acids (or D-amino acid residues) are not isotopically labeled. In some embodiments, at least one of the L-amino acids (or L-amino acid residues) is isotopically labeled. In some embodiments, the L-amino acids (or L-amino acid residues) are not isotopically labeled.

In various embodiments, the natural natriuretic peptides comprise a plurality of amino acids (or amino acid residues). In some embodiments, the amino acids (or amino acid residues) are selected from Ala, Ile, Leu, Met, Val, Phe, Trp, Tyr, Asn, Cys, Gln, Ser, Thr, Asp, Glu, Arg, His, Lys, Gly, and Pro. In some embodiments, the amino acids (or amino acid residues) are L-amino acids (or L-amino acid residues). In some embodiments, the L-amino acids (or L-amino acid residues) are selected from the group consisting of L-enantiomers of Ala, Ile, Leu, Met, Val, Phe, Trp, Tyr, Asn, Cys, Gln, Ser, Thr, Asp, Glu, Arg, His, Lys, and Pro. In some embodiments, the amino acids (or amino acid residues) are selected from chiral amino acids (or chiral amino acid residues) and non-chiral amino acids (or non-chiral amino acid residues), wherein each chiral amino acid (or chiral amino acid residue) is a L-amino acid (or L-amino acid residue). In some embodiments, the non-chiral amino acid (or non-chiral amino acid residue) is glycine (Gly). In some embodiments, the non-chiral amino acid is glycine (Gly). In some embodiments, the non-chiral amino acid residue is a glycine (Gly) amino acid residue.

In various embodiments, the cleavable synthetic natriuretic peptides comprise a plurality of amino acids (or amino acid residues). In some embodiments, the amino acids (or amino acid residues) are selected from Ala, Ile, Leu, Met, Val, Phe, Trp, Tyr, Asn, Cys, Gln, Ser, Thr, Asp, Glu, Arg, His, Lys, Gly, and Pro. In some embodiments, the amino acids (or amino acid residues) are L-amino acids. In some embodiments, the L-amino acids are selected from the group consisting of L-enantiomers of Ala, Ile, Leu, Met, Val, Phe, Trp, Tyr, Asn, Cys, Gln, Ser, Thr, Asp, Glu, Arg, His, Lys, and Pro. In some embodiments, the amino acids (or amino acid residues) are selected from chiral amino acids (or chiral amino acid residues) and non-chiral amino acids (or non-chiral amino acid residues), wherein each chiral amino acid (or chiral amino acid residue) is a L-amino acid (or L-amino acid residue). In some embodiments, the non-chiral amino acid is glycine (Gly). In some embodiments, the non-chiral amino acid residue is a glycine (Gly) amino acid residue. In some embodiments, the non-chiral amino acid (or non-chiral amino acid residue) is glycine (Gly).

In various embodiments, the non-natural natriuretic peptides comprise a plurality of amino acids (or amino acid residues). In some embodiments, the amino acids (or amino acid residues) are selected from Ala, Ile, Leu, Met, Val, Phe, Trp, Tyr, Asn, Cys, Gln, Ser, Thr, Asp, Glu, Arg, His, Lys, Gly, and Pro. In some embodiments, one or more of the amino acids (or amino acid residues) are L-amino acids (or L-amino acid residues). In some embodiments, the L-amino acids (or L-amino acid residues) are selected from the group consisting of L-enantiomers of Ala, Ile, Leu, Met, Val, Phe, Trp, Tyr, Asn, Cys, Gln, Ser, Thr, Asp, Glu, Arg, His, Lys, and Pro. In some embodiments, one or more of the amino acids (or amino acid residues) are D-amino acids (or D-amino acid residues). In some embodiments, the D-amino acids (or D-amino acid residues) are selected from the group consisting of D-enantiomers of Ala, Ile, Leu, Met, Val, Phe, Trp, Tyr, Asn, Cys, Gln, Ser, Thr, Asp, Glu, Arg, His, Lys, and Pro. In some embodiments, one or more of the amino acids (or amino acid residues) are L-amino acids (or L-amino acid residues); and one or more of the amino acids (or amino acid residues) are D-amino acids (or D-amino acid residues). In some embodiments, the amino acids (or amino acid residues) are selected from chiral amino acids (or chiral amino acid residues) and non-chiral amino acids (or non-chiral amino acid residues), In some embodiments, the amino acids (or amino acid residues) are selected from chiral amino acids (or chiral amino acid residues) and non-chiral amino acids (or non-chiral amino acid residues), wherein each chiral amino acid (or chiral amino acid residue) is a D-amino acid (or D-amino acid residue). In some embodiments, the non-chiral amino acid (or non-chiral amino acid residue) is glycine (Gly). In some embodiments, the non-chiral amino acid is glycine (Gly). In some embodiments, the non-chiral amino acid residue is a glycine (Gly) amino acid residue.

In various embodiments, one or more amino acids are selected from Ala, Ile, Leu, Met, Val, Phe, Trp, Tyr, Asn, Cys, Gln, Ser, Thr, Asp, Glu, Arg, His, Lys, Gly, and Pro.

In various embodiments, the chiral amino acid is selected from Ala, Ile, Leu, Met, Val, Phe, Trp, Tyr, Asn, Cys, Gln, Ser, Thr, Asp, Glu, Arg, His, Lys, and Pro.

In various embodiments, the chiral amino acid residue is selected from Ala, Ile, Leu, Met, Val, Phe, Trp, Tyr, Asn, Cys, Gln, Ser, Thr, Asp, Glu, Arg, His, Lys, and Pro. In various embodiments, the chiral amino acid residue is selected from an Ala, Ile, Leu, Met, Val, Phe, Trp, Tyr, Asn, Cys, Gln, Ser, Thr, Asp, Glu, Arg, His, Lys, and Pro amino acid residue.

In various embodiments, the non-chiral amino acid is Gly.

In various embodiments, the non-chiral amino acid residue is Gly. In various embodiments, the non-chiral amino acid residue is a Gly amino acid residue.

In various embodiments, one or more D-amino acids are selected from the group consisting of D-enantiomers of Ala, Ile, Leu, Met, Val, Phe, Trp, Tyr, Asn, Cys, Gln, Ser, Thr, Asp, Glu, Arg, His, Lys, and Pro.

In various embodiments, one or more D-amino acid residues are selected from the group consisting of D-enantiomers of Ala, Ile, Leu, Met, Val, Phe, Trp, Tyr, Asn, Cys, Gln, Ser, Thr, Asp, Glu, Arg, His, Lys, and Pro amino acid residues.

In various embodiments, one or more L-amino acids are selected from the group consisting of L-enantiomers of Ala, Ile, Leu, Met, Val, Phe, Trp, Tyr, Asn, Cys, Gln, Ser, Thr, Asp, Glu, Arg, His, Lys, and Pro.

In various embodiments, one or more L-amino acid residues are selected from the group consisting of L-enantiomers of Ala, Ile, Leu, Met, Val, Phe, Trp, Tyr, Asn, Cys, Gln, Ser, Thr, Asp, Glu, Arg, His, Lys, and Pro amino acid residues.

In some embodiments, the Gly amino acid is isotopically labeled. In some embodiments, the Gly amino acid is not isotopically labeled. In some embodiments, the Gly amino acid residue is isotopically labeled. In some embodiments, the Gly amino acid residue is not isotopically labeled.

In various embodiments, the present invention provides, a non-natural natriuretic peptide comprising one or more D-amino acids. In some embodiments, the non-natural natriuretic peptide is any one or more of non-natural brain natriuretic peptides (non-natural B-type natriuretic peptides), non-natural atrial natriuretic peptides (non-natural A-type natriuretic peptides), non-natural C-type natriuretic peptides, or combinations thereof. In some embodiments, at least one of the D-amino acids are isotopically labeled. In some embodiments, the D-amino acids are not isotopically labeled. In some embodiments, the one or more D-amino acids are selected from the group consisting of D-enantiomers of Ala, Ile, Leu, Met, Val, Phe, Trp, Tyr, Asn, Cys, Gln, Ser, Thr, Asp, Glu, Arg, His, Lys, and Pro. In some embodiments, the non-natural natriuretic peptide further comprises one or more L-amino acids. In some embodiments, at least one of the L-amino acids are isotopically labeled. In some embodiments, the L-amino acids are not isotopically labeled. In some embodiments, wherein the one or more L-amino acids are selected from the group consisting of L-enantiomers of Ala, Ile, Leu, Met, Val, Phe, Trp, Tyr, Asn, Cys, Gln, Ser, Thr, Asp, Glu, Arg, His, Lys, and Pro. In some embodiments, the non-natural natriuretic peptide further comprises one or more Gly amino acids.

In various embodiments, the present invention provides a kit, comprising: (a) an internal standard, wherein the internal standard comprises one or more non-natural natriuretic peptides, or one or more non-natural cleavage peptidoforms, or combination thereof; (b) one or more L-natriuretic peptides; and (c) instructions for using the kit. In some embodiments, the non-natural natriuretic peptide is non-natural brain natriuretic peptide, non-natural atrial natriuretic peptide, or non-natural C-type natriuretic peptide, or combinations thereof. In some embodiments, the L-natriuretic peptide is a natural natriuretic peptide, or a cleavable synthetic natriuretic peptide, or combination thereof. In some embodiments, the natural natriuretic peptide is natural brain natriuretic peptide, natural atrial natriuretic peptide, or natural C-type natriuretic peptide, or combinations thereof. In some embodiments, the cleavable synthetic natriuretic peptide is cleavable synthetic brain natriuretic peptide, cleavable synthetic atrial natriuretic peptide, or cleavable synthetic C-type natriuretic peptide, or combinations thereof. In some embodiments, the non-natural natriuretic peptide comprises one or more D-amino acids. In some embodiments, at least one of the D-amino acids are isotopically labeled. In some embodiments, the D-amino acids are not isotopically labeled. In some embodiments, the D-amino acids are selected from the group consisting of D-enantiomers of Ala, Ile, Leu, Met, Val, Phe, Trp, Tyr, Asn, Cys, Gln, Ser, Thr, Asp, Glu, Arg, His, Lys, and Pro. In some embodiments, an amount of non-natural natriuretic peptide and an amount of L-natriuretic peptide are the same. In some embodiments, the non-natural natriuretic peptide further comprises one or more L-amino acids. In some embodiments, at least one of the L-amino acids are isotopically labeled. In some embodiments, the L-amino acids are not isotopically labeled. In some embodiments, the one or more L-amino acids are selected from the group consisting of L-enantiomers of Ala, Ile, Leu, Met, Val, Phe, Trp, Tyr, Asn, Cys, Gln, Ser, Thr, Asp, Glu, Arg, His, Lys, and Pro. In some embodiments, the non-natural natriuretic peptide further comprises one or more Gly amino acids.

In various embodiments, the present invention provides a kit for obtaining a proteolytic profile from a sample comprising: (a) an internal standard, wherein the internal standard comprises one or more non-natural natriuretic peptides, wherein the non-natural natriuretic peptides comprise one or more D-amino acids; (b) one or more L-natriuretic peptides; and (c) instructions for using the kit to obtain the proteolytic profile for the sample. In some embodiments, the non-natural natriuretic peptide is non-natural brain natriuretic peptide, non-natural atrial natriuretic peptide, or non-natural C-type natriuretic peptide, or combinations thereof. In some embodiments, the L-natriuretic peptide is a natural natriuretic peptide, or a cleavable synthetic natriuretic peptide, or combination thereof. In some embodiments, the natural natriuretic peptide is natural brain natriuretic peptide, natural atrial natriuretic peptide, or natural C-type natriuretic peptide, or combinations thereof. In some embodiments, the cleavable synthetic natriuretic peptide is cleavable synthetic brain natriuretic peptide, cleavable synthetic atrial natriuretic peptide, or cleavable synthetic C-type natriuretic peptide, or combinations thereof. In some embodiments, at least one of the D-amino acids are isotopically labeled. In some embodiments, the D-amino acids are not isotopically labeled. In some embodiments, the D-amino acids are selected from the group consisting of D-enantiomers of Ala, Ile, Leu, Met, Val, Phe, Trp, Tyr, Asn, Cys, Gln, Ser, Thr, Asp, Glu, Arg, His, Lys, and Pro. In some embodiments, an amount of non-natural natriuretic peptide and an amount of L-natriuretic peptide are the same. In some embodiments, the non-natural natriuretic peptide further comprises one or more L-amino acids. In some embodiments, at least one of the L-amino acids are isotopically labeled. In some embodiments, the L-amino acids are not isotopically labeled. In some embodiments, the one or more L-amino acids are selected from the group consisting of L-enantiomers of Ala, Ile, Leu, Met, Val, Phe, Trp, Tyr, Asn, Cys, Gln, Ser, Thr, Asp, Glu, Arg, His, Lys, and Pro. In some embodiments, the non-natural natriuretic peptide further comprises one or more Gly amino acids.

In various embodiments, the present invention provides a kit for identifying and/or assessing a condition of a subject, the kit comprising: (a) an internal standard, wherein the internal standard comprises one or more non-natural natriuretic peptides, wherein the non-natural natriuretic peptides comprise one or more D-amino acids; (b) one or more L-natriuretic peptides; (c) reagents and instructions for sample processing and preparation; (d) instructions for using the kit to obtain a proteolytic profile for the subject; (e) one or more reference proteolytic profiles characteristic for one or more diseases; and (f) instructions for using the kit to identify and/or assess the condition of the subject. In some embodiments, the condition is a disease In some embodiments, the disease is a cardiovascular disease. In some embodiments, the non-natural natriuretic peptide is non-natural brain natriuretic peptide, non-natural atrial natriuretic peptide, or non-natural C-type natriuretic peptide, or combinations thereof. In some embodiments, the L-natriuretic peptide is a natural natriuretic peptide, or a cleavable synthetic natriuretic peptide, or combination thereof. In some embodiments, the natural natriuretic peptide is natural brain natriuretic peptide, natural atrial natriuretic peptide, or natural C-type natriuretic peptide, or combinations thereof. In some embodiments, the cleavable synthetic natriuretic peptide is cleavable synthetic brain natriuretic peptide, cleavable synthetic atrial natriuretic peptide, or cleavable synthetic C-type natriuretic peptide, or combinations thereof. In some embodiments, at least one of the D-amino acids are isotopically labeled. In some embodiments, the D-amino acids are not isotopically labeled. In some embodiments, the D-amino acids are selected from the group consisting of D-enantiomers of Ala, Ile, Leu, Met, Val, Phe, Trp, Tyr, Asn, Cys, Gln, Ser, Thr, Asp, Glu, Arg, His, Lys, and Pro. In some embodiments, an amount of non-natural natriuretic peptide and an amount of L-natriuretic peptide are the same. In some embodiments, the non-natural natriuretic peptide further comprises one or more L-amino acids. In some embodiments, at least one of the L-amino acids are isotopically labeled. In some embodiments, the L-amino acids are not isotopically labeled. In some embodiments, the one or more L-amino acids are selected from the group consisting of L-enantiomers of Ala, Ile, Leu, Met, Val, Phe, Trp, Tyr, Asn, Cys, Gln, Ser, Thr, Asp, Glu, Arg, His, Lys, and Pro. In some embodiments, the non-natural natriuretic peptide further comprises one or more Gly amino acids.

In various embodiments, the present invention provides a pharmaceutical composition, comprising: one or more non-natural natriuretic peptides, wherein the non-natural natriuretic peptide comprises one or more D-amino acids; and a pharmaceutically acceptable carrier.

In various embodiments, the present invention provides a method of obtaining a proteolytic profile of one or more cleavage products of one or more L-natriuretic peptides for a subject, the method comprising: obtaining a sample comprising one or more proteases from the subject; adding an amount of one or more L-natriuretic peptides to the sample; adding an amount of an internal standard to the sample, wherein the internal standard comprises one or more non-natural natriuretic peptides, one or more non-natural cleavage peptidoforms, or combination thereof; detecting and/or measuring an amount of one or more L-natriuretic peptides over a period of time; detecting and/or measuring an amount of the internal standard over a period of time; and quantifying the amount of one or more L-natriuretic peptide cleavage products by comparing the amount of one or more L-natriuretic peptide cleavage products with the amount of the internal standard to obtain the proteolytic profile of the subject. In some embodiments, the method further comprises comparing the proteolytic profile from the subject to a proteolytic profile from a reference sample, and making an assessment of the subject based on the comparison, wherein the assessment is a diagnosis of a disease. In some embodiments, the method further comprises treating the subject, selecting a treatment for the subject, and/or providing a treatment for the subject based on the assessment. In some embodiments, the disease is a cardiovascular disease. In some embodiments, the reference sample is obtained from a control subject, wherein the control subject does not have the disease. In some embodiments, the reference sample is obtained from the subject before the subject is treated for the disease. In some embodiments, the reference sample is from a subject that has been successfully treated for the disease. In some embodiments, the non-natural natriuretic peptide is non-natural brain natriuretic peptide, non-natural atrial natriuretic peptide, or non-natural C-type natriuretic peptide, or combinations thereof. In some embodiments, the L-natriuretic peptide is a natural natriuretic peptide, or a cleavable synthetic natriuretic peptide, or combination thereof. In some embodiments, the natural natriuretic peptide is natural brain natriuretic peptide, natural atrial natriuretic peptide, or natural C-type natriuretic peptide, or combinations thereof. In some embodiments, the cleavable synthetic natriuretic peptide is cleavable synthetic brain natriuretic peptide, cleavable synthetic atrial natriuretic peptide, or cleavable synthetic C-type natriuretic peptide, or combinations thereof. In some embodiments, the non-natural natriuretic peptide comprises one or more D-amino acids. In some embodiments, the non-natural natriuretic peptide is isotopically labeled. In some embodiments, the non-natural natriuretic peptide is not isotopically labeled. In some embodiments, at least one of the D-amino acids are isotopically labeled. In some embodiments, the D-amino acids are not isotopically labeled. In some embodiments, the D-amino acids are selected from the group consisting of D-enantiomers of Ala, Ile, Leu, Met, Val, Phe, Trp, Tyr, Asn, Cys, Gln, Ser, Thr, Asp, Glu, Arg, His, Lys, and Pro. In some embodiments, an amount of non-natural natriuretic peptide and an amount of L-natriuretic peptide are the same. In some embodiments, the non-natural natriuretic peptide further comprises one or more L-amino acids. In some embodiments, at least one of the L-amino acids are isotopically labeled. In some embodiments, the one or more L-amino acids are selected from the group consisting of L-enantiomers of Ala, Ile, Leu, Met, Val, Phe, Trp, Tyr, Asn, Cys, Gln, Ser, Thr, Asp, Glu, Arg, His, Lys, and Pro. In some embodiments, the method further comprises detecting and/or measuring the amount of one or more L-natriuretic peptides over a period of time; and quantifying the amount of one or more L-natriuretic peptides by comparing the amount of one or more L-natriuretic peptides with the amount of the internal standard. In some embodiments, the L-natriuretic peptides and/or the L-natriuretic peptide cleavage products are measured and/or quantified and/or detected using any one or more of capillary electrophoresis (CE), mass spectrometry (MS), capillary electrophoresis/electrospray ionization-mass spectrometry (CESI-MS), capillary electrophoresis-mass spectrometry (CE-MS), liquid chromatography mass spectrometry (LC-MS), high pressure liquid chromatography mass spectrometry (HPLC-MS), or combinations thereof. In some embodiments, the non-natural natriuretic peptides and/or the non-natural cleavage peptidoforms are measured and/or quantified and/or detected using any one or more of capillary electrophoresis (CE), mass spectrometry (MS), capillary electrophoresis/electrospray ionization-mass spectrometry (CESI-MS), capillary electrophoresis-mass spectrometry (CE-MS), liquid chromatography mass spectrometry (LC-MS), high pressure liquid chromatography mass spectrometry (HPLC-MS), or combinations thereof. In some embodiments, the proteases are any one or more of neutral endopeptidase (NEP), dipeptidylpeptidase IV (DPPIV), and insulin degrading enzyme (IDE), or combination thereof.

In various embodiments, the present invention provides a method for diagnosing a disease in a subject, comprising: obtaining a sample comprising one or more proteases from the subject; adding an amount of one or more L-natriuretic peptides to the sample; adding an amount of an internal standard to the sample, wherein the internal standard comprises one or more non-natural natriuretic peptides, one or more non-natural cleavage peptidoforms, or combination thereof detecting and/or measuring an amount of one or more L-natriuretic peptide cleavage products of the one or more L-natriuretic peptides over a period of time; detecting and/or measuring an amount of the internal standard over a period of time; quantifying the amount of one or more L-natriuretic peptide cleavage product by comparing the amount of one or more L-natriuretic peptide cleavage products with the amount of the internal standard to obtain the proteolytic profile of the subject; and comparing the proteolytic profile from the subject to a proteolytic profile from a reference sample, wherein a change in the proteolytic profile from the subject relative to the proteolytic profile from the reference sample is indicative of a disease in the subject. In some embodiments, the method further comprises treating the subject and/or selecting at treatment for the subject and/or providing a treatment for the subject. In some embodiments, the reference sample is obtained from a control subject, wherein the control subject does not have the disease. In some embodiments, the reference sample is obtained from the subject before the subject is treated for the disease. In some embodiments, the reference sample is from a subject that has been successfully treated for the disease. In some embodiments, the non-natural natriuretic peptide is non-natural brain natriuretic peptide, non-natural atrial natriuretic peptide, or non-natural C-type natriuretic peptide, or combinations thereof. In some embodiments, the L-natriuretic peptide is a natural natriuretic peptide, or a cleavable synthetic natriuretic peptide, or combination thereof. In some embodiments, the natural natriuretic peptide is natural brain natriuretic peptide, natural atrial natriuretic peptide, or natural C-type natriuretic peptide, or combinations thereof. In some embodiments, the cleavable synthetic natriuretic peptide is cleavable synthetic brain natriuretic peptide, cleavable synthetic atrial natriuretic peptide, or cleavable synthetic C-type natriuretic peptide, or combinations thereof. In some embodiments, the non-natural natriuretic peptide comprises one or more D-amino acids. In some embodiments, the non-natural natriuretic peptide is isotopically labeled. In some embodiments, the non-natural natriuretic peptide is not isotopically labeled. In some embodiments, at least one of the D-amino acids are isotopically labeled. In some embodiments, the D-amino acids are not isotopically labeled. In some embodiments, the D-amino acids are selected from the group consisting of D-enantiomers of Ala, Ile, Leu, Met, Val, Phe, Trp, Tyr, Asn, Cys, Gln, Ser, Thr, Asp, Glu, Arg, His, Lys, and Pro. In some embodiments, an amount of non-natural natriuretic peptide and an amount of L-natriuretic peptide are the same. In some embodiments, the non-natural natriuretic peptide further comprises one or more L-amino acids. In some embodiments, at least one of the L-amino acids are isotopically labeled. In some embodiments, the one or more L-amino acids are selected from the group consisting of L-enantiomers of Ala, Ile, Leu, Met, Val, Phe, Trp, Tyr, Asn, Cys, Gln, Ser, Thr, Asp, Glu, Arg, His, Lys, and Pro. In some embodiments, the method further comprises detecting and/or measuring the amount of one or more L-natriuretic peptides over a period of time; and quantifying the amount of one or more L-natriuretic peptides by comparing the amount of one or more L-natriuretic peptides with the amount of the internal standard. In some embodiments, the L-natriuretic peptides and/or the L-natriuretic peptide cleavage products are measured and/or quantified and/or detected using any one or more of capillary electrophoresis (CE), mass spectrometry (MS), capillary electrophoresis/electrospray ionization-mass spectrometry (CESI-MS), capillary electrophoresis-mass spectrometry (CE-MS), liquid chromatography mass spectrometry (LC-MS), high pressure liquid chromatography mass spectrometry (HPLC-MS), or combinations thereof. In some embodiments, the non-natural natriuretic peptides and/or the non-natural cleavage peptidoforms are measured and/or quantified and/or detected using any one or more of capillary electrophoresis (CE), mass spectrometry (MS), capillary electrophoresis/electrospray ionization-mass spectrometry (CESI-MS), capillary electrophoresis-mass spectrometry (CE-MS), liquid chromatography mass spectrometry (LC-MS), high pressure liquid chromatography mass spectrometry (HPLC-MS), or combinations thereof. In some embodiments, the proteases are any one or more of neutral endopeptidase (NEP), dipeptidylpeptidase IV (DPPIV), and insulin degrading enzyme (IDE), or combination thereof.

In various embodiments, the present invention provides a method for assessing and/or determining the risk of developing a disease in a subject, comprising: obtaining a sample comprising one or more proteases from the subject; adding an amount of one or more L-natriuretic peptides to the sample; adding an amount of an internal standard to the sample, wherein the internal standard comprises one or more non-natural natriuretic peptides, one or more non-natural cleavage peptidoforms, or combination thereof; detecting and/or measuring an amount of one or more L-natriuretic peptide cleavage products of the one or more L-natriuretic peptides over a period of time; detecting and/or measuring an amount of the internal standard over a period of time; quantifying the amount of one or more L-natriuretic peptide cleavage product by comparing the amount of one or more L-natriuretic peptide cleavage products with the amount of the internal standard to obtain the proteolytic profile of the subject; and comparing the proteolytic profile from the subject to a proteolytic profile from a reference sample, wherein a change in the proteolytic profile from the subject relative to the proteolytic profile from the reference sample is indicative of an increased risk of the subject developing the disease. In some embodiments, the reference sample is obtained from a control subject, wherein the control subject does not have the disease. In some embodiments, the reference sample is obtained from the subject before the subject is treated for the disease. In some embodiments, the reference sample is from a subject that has been successfully treated for the disease. In some embodiments, the non-natural natriuretic peptide is non-natural brain natriuretic peptide, non-natural atrial natriuretic peptide, or non-natural C-type natriuretic peptide, or combinations thereof. In some embodiments, the L-natriuretic peptide is a natural natriuretic peptide, or a cleavable synthetic natriuretic peptide, or combination thereof. In some embodiments, the natural natriuretic peptide is natural brain natriuretic peptide, natural atrial natriuretic peptide, or natural C-type natriuretic peptide, or combinations thereof. In some embodiments, the cleavable synthetic natriuretic peptide is cleavable synthetic brain natriuretic peptide, cleavable synthetic atrial natriuretic peptide, or cleavable synthetic C-type natriuretic peptide, or combinations thereof. In some embodiments, the non-natural natriuretic peptide comprises one or more D-amino acids. In some embodiments, the non-natural natriuretic peptide is isotopically labeled. In some embodiments, the non-natural natriuretic peptide is not isotopically labeled. In some embodiments, at least one of the D-amino acids are isotopically labeled. In some embodiments, the D-amino acids are not isotopically labeled. In some embodiments, the D-amino acids are selected from the group consisting of D-enantiomers of Ala, Ile, Leu, Met, Val, Phe, Trp, Tyr, Asn, Cys, Gln, Ser, Thr, Asp, Glu, Arg, His, Lys, and Pro. In some embodiments, an amount of non-natural natriuretic peptide and an amount of L-natriuretic peptide are the same. In some embodiments, the non-natural natriuretic peptide further comprises one or more L-amino acids. In some embodiments, at least one of the L-amino acids are isotopically labeled. In some embodiments, the one or more L-amino acids are selected from the group consisting of L-enantiomers of Ala, Ile, Leu, Met, Val, Phe, Trp, Tyr, Asn, Cys, Gln, Ser, Thr, Asp, Glu, Arg, His, Lys, and Pro. In some embodiments, the method further comprises detecting and/or measuring the amount of one or more L-natriuretic peptides over a period of time; and quantifying the amount of one or more L-natriuretic peptides by comparing the amount of one or more L-natriuretic peptides with the amount of the internal standard. In some embodiments, the L-natriuretic peptides and/or the L-natriuretic peptide cleavage products are measured and/or quantified and/or detected using any one or more of capillary electrophoresis (CE), mass spectrometry (MS), capillary electrophoresis/electrospray ionization-mass spectrometry (CESI-MS), capillary electrophoresis-mass spectrometry (CE-MS), liquid chromatography mass spectrometry (LC-MS), high pressure liquid chromatography mass spectrometry (HPLC-MS), or combinations thereof. In some embodiments, the non-natural natriuretic peptides and/or the non-natural cleavage peptidoforms are measured and/or quantified and/or detected using any one or more of capillary electrophoresis (CE), mass spectrometry (MS), capillary electrophoresis/electrospray ionization-mass spectrometry (CESI-MS), capillary electrophoresis-mass spectrometry (CE-MS), liquid chromatography mass spectrometry (LC-MS), high pressure liquid chromatography mass spectrometry (HPLC-MS), or combinations thereof. In some embodiments, the proteases are any one or more of neutral endopeptidase (NEP), dipeptidylpeptidase IV (DPPIV), and insulin degrading enzyme (IDE), or combination thereof.

In various embodiments, the present invention provides a method of diagnosing and/or prognosing a condition in a subject, comprising: obtaining a sample comprising one or more proteases from the subject; adding an amount of one or more L-natriuretic peptides to the sample; adding an amount of an internal standard to the sample, wherein the internal standard comprises one or more non-natural natriuretic peptides, one or more non-natural cleavage peptidoforms, or combination thereof; detecting and/or measuring an amount of one or more L-natriuretic peptide cleavage products of the one or more L-natriuretic peptides over a period of time; detecting and/or measuring an amount of the internal standard over a period of time; quantifying the amount of one or more L-natriuretic peptide cleavage products by comparing the amount of one or more L-natriuretic peptide cleavage products with the amount of the internal standard to obtain the proteolytic profile of the subject; comparing the proteolytic profile from the subject to a proteolytic profile from one or more reference samples; and diagnosing and/or prognosing the condition of the subject based on the comparison. In some embodiments, the reference sample is from a diseased subject having one or more diseases. In some embodiments, the reference sample is from a healthy subject. In some embodiments, the method further comprises treating the subject and/or selecting a treatment and/or providing a treatment and/or selecting a preventative treatment and/or providing a preventative treatment for the subject based on the diagnosis and/or prognosis. In some embodiments, the condition is a disease. In some embodiments, the disease is a cardiovascular disease. In some embodiments, the reference sample is obtained from a control subject, wherein the control subject does not have the disease. In some embodiments, the reference sample is obtained from the subject before the subject is treated for the disease. In some embodiments, the reference sample is from a subject that has been successfully treated for the disease. In some embodiments, the non-natural natriuretic peptide is non-natural brain natriuretic peptide, non-natural atrial natriuretic peptide, or non-natural C-type natriuretic peptide, or combinations thereof. In some embodiments, the L-natriuretic peptide is a natural natriuretic peptide, or a cleavable synthetic natriuretic peptide, or combination thereof. In some embodiments, the natural natriuretic peptide is natural brain natriuretic peptide, natural atrial natriuretic peptide, or natural C-type natriuretic peptide, or combinations thereof. In some embodiments, the cleavable synthetic natriuretic peptide is cleavable synthetic brain natriuretic peptide, cleavable synthetic atrial natriuretic peptide, or cleavable synthetic C-type natriuretic peptide, or combinations thereof. In some embodiments, the non-natural natriuretic peptide comprises one or more D-amino acids. In some embodiments, the non-natural natriuretic peptide is isotopically labeled. In some embodiments, the non-natural natriuretic peptide is not isotopically labeled. In some embodiments, at least one of the D-amino acids are isotopically labeled. In some embodiments, the D-amino acids are not isotopically labeled. In some embodiments, the D-amino acids are selected from the group consisting of D-enantiomers of Ala, Ile, Leu, Met, Val, Phe, Trp, Tyr, Asn, Cys, Gln, Ser, Thr, Asp, Glu, Arg, His, Lys, and Pro. In some embodiments, an amount of non-natural natriuretic peptide and an amount of L-natriuretic peptide are the same. In some embodiments, the non-natural natriuretic peptide further comprises one or more L-amino acids. In some embodiments, at least one of the L-amino acids are isotopically labeled. In some embodiments, the one or more L-amino acids are selected from the group consisting of L-enantiomers of Ala, Ile, Leu, Met, Val, Phe, Trp, Tyr, Asn, Cys, Gln, Ser, Thr, Asp, Glu, Arg, His, Lys, and Pro. In some embodiments, the method further comprises detecting and/or measuring the amount of one or more L-natriuretic peptides over a period of time; and quantifying the amount of one or more L-natriuretic peptides by comparing the amount of one or more L-natriuretic peptides with the amount of the internal standard. In some embodiments, the L-natriuretic peptides and/or the L-natriuretic peptide cleavage products are measured and/or quantified and/or detected using any one or more of capillary electrophoresis (CE), mass spectrometry (MS), capillary electrophoresis/electrospray ionization-mass spectrometry (CESI-MS), capillary electrophoresis-mass spectrometry (CE-MS), liquid chromatography mass spectrometry (LC-MS), high pressure liquid chromatography mass spectrometry (HPLC-MS), or combinations thereof in some embodiments, the non-natural natriuretic peptides and/or the non-natural cleavage peptidoforms are measured and/or quantified and/or detected using any one or more of capillary electrophoresis (CE), mass spectrometry (MS), capillary electrophoresis/electrospray ionization-mass spectrometry (CESI-MS), capillary electrophoresis-mass spectrometry (CE-MS), liquid chromatography mass spectrometry (LC-MS), high pressure liquid chromatography mass spectrometry (HPLC-MS), or combinations thereof. In some embodiments, the proteases are any one or more of neutral endopeptidase (NEP), dipeptidylpeptidase IV (DPPIV), and insulin degrading enzyme (IDE), or combination thereof.

In various embodiments, the present invention provides a non-natural natriuretic peptide comprising a plurality of amino acids, wherein the amino acids are selected from chiral and non-chiral amino acids, wherein each chiral amino acid is a D-amino acid. In some embodiments, the non-natural natriuretic peptide is any one or more of non-natural brain natriuretic peptides, non-natural atrial natriuretic peptides, non-natural C-type natriuretic peptides, or combinations thereof. In some embodiments, at least one of the D-amino acids are isotopically labeled. In some embodiments, the D-amino acids are not isotopically labeled. In some embodiments, the D-amino acids are selected from the group consisting of D-enantiomers of Ala, Ile, Leu, Met, Val, Phe, Trp, Tyr, Asn, Cys, Gln, Ser, Thr, Asp, Glu, Arg, His, Lys, and Pro. In some embodiments, the non-chiral amino acid is Gly.

ADDITIONAL METHODS OF THE INVENTION

Method for Monitoring and/or Assessing Efficacy of a Treatment and/or Therapy

In various embodiments, the present invention provides a method for monitoring and/or assessing efficacy of a treatment and/or therapy of a subject, comprising: obtaining a sample comprising one or more proteases from the subject, wherein the subject is being and/or has been treated and/or is/has received therapy for a disease; adding an amount of one or more L-natriuretic peptides to the sample; adding an amount of an internal standard to the sample, wherein the internal standard comprises one or more non-natural natriuretic peptides, one or more non-natural cleavage peptidoforms, or combination thereof; detecting and/or measuring an amount of one or more L-natriuretic peptide cleavage products over a period of time; detecting and/or measuring an amount of the internal standard over a period of time; quantifying the amount of one or more L-natriuretic peptide cleavage products by comparing the amount of one or more L-natriuretic peptide cleavage products with the amount of the internal standard to obtain the proteolytic profile of the subject; and comparing the proteolytic profile from the subject to a proteolytic profile from a reference sample, wherein a change in the proteolytic profile from the subject relative to the proteolytic profile from the reference sample provides for monitoring of the treatment/therapy and/or provides an assessment of the efficacy of the treatment/therapy. In some embodiments, the detecting and/or measuring of the internal standard comprises detecting and/or measuring the amount of the non-natural natriuretic peptide or the amount of the non-natural cleavage peptidoform. In some embodiments, the quantifying the amount of one or more L-natriuretic peptide cleavage products by comparing the amount of one or more L-natriuretic peptide cleavage products with the amount of the internal standard to obtain the proteolytic profile of the subject, comprises quantifying the amount of one or more L-natriuretic peptide cleavage products by comparing the amount of one or more L-natriuretic peptide cleavage products with the amount of the non-natural natriuretic peptide or the amount of the non-natural cleavage peptidoform.

Method for Assessing the Risk of Developing a Disease

In various embodiments, the present invention provides a method for assessing the risk of developing a disease in a subject, comprising: obtaining a sample comprising one or more proteases from the subject; adding an amount of one or more L-natriuretic peptides to the sample; adding an amount of an internal standard to the sample, wherein the internal standard comprises one or more non-natural natriuretic peptides, one or more non-natural cleavage peptidoforms, or combination thereof; detecting and/or measuring an amount of one or more L-natriuretic peptide cleavage products over a period of time; detecting and/or measuring an amount of the internal standard over a period of time; quantifying the amount of one or more L-natriuretic peptide cleavage products by comparing the amount of one or more L-natriuretic peptide cleavage products with the amount of the internal standard, where an increase in the amount of one or more L-natriuretic peptide cleavage products over a period of time is indicative of increased protease activity; determining that the subject has an increased risk of developing a disease if the protease activity is increased over the period of time relative to a reference value; and determining that the subject has a decreased risk of developing a disease if the protease activity is decreased over the period of time relative to the reference value. In some embodiments, the method further comprises selecting a treatment for the subject if the increased risk of developing a disease is determined. In some embodiments, the method further comprises detecting and/or measuring an amount of the one or more L-natriuretic peptides over a period of time. In some embodiments, the method further comprises quantifying the amount of the one or more L-natriuretic peptides over time by comparing the amount of one or more L-natriuretic peptides with the amount of the internal standard, wherein a decrease in the amount of one or more L-natriuretic peptides over a period of time is indicative of increased protease activity. In some embodiments, the disease is a cardiovascular disease. In some embodiments, the method further comprises treating the subject at risk of developing the disease. In some embodiments, the detecting and/or measuring of the internal standard comprises detecting and/or measuring the amount of the non-natural natriuretic peptide or the amount of the non-natural cleavage peptidoform.

Method of Obtaining a Proteolytic Profile

In various embodiments, the present invention provides a method of obtaining a proteolytic profile of one or more cleavage products of one or more L-natriuretic peptides for a subject, the method comprising: obtaining a sample comprising one or more proteases from the subject; adding an amount of one or more L-natriuretic peptides to the sample; adding an amount of an internal standard to the sample, wherein the internal standard comprises one or more non-natural natriuretic peptides, one or more non-natural cleavage peptidoforms, or combination thereof; detecting and/or measuring an amount of one or more L-natriuretic peptides over a period of time; detecting and/or measuring an amount of the internal standard over a period of time; and quantifying the amount of one or more L-natriuretic peptide cleavage products by comparing the amount of one or more L-natriuretic peptide cleavage products with the amount of the internal standard to obtain the proteolytic profile of the subject. In some embodiments, the method further comprises detecting and/or measuring an amount of the one or more L-natriuretic peptides over a period of time. In some embodiments, the method further comprises quantifying the amount of the one or more L-natriuretic peptides over time by comparing the amount of one or more L-natriuretic peptides with the amount of the internal standard to obtain the proteolytic profile of the subject. In some embodiments, the detecting and/or measuring of the internal standard comprises detecting and/or measuring the amount of the non-natural natriuretic peptide or the amount of the non-natural cleavage peptidoform. In some embodiments, the quantifying the amount of one or more L-natriuretic peptide cleavage products by comparing the amount of one or more L-natriuretic peptide cleavage products with the amount of the internal standard to obtain the proteolytic profile of the subject, comprises quantifying the amount of one or more L-natriuretic peptide cleavage products by comparing the amount of one or more L-natriuretic peptide cleavage products with the amount of the non-natural natriuretic peptide or the amount of the non-natural cleavage peptidoform.

In some embodiments, the method further comprises comparing the proteolytic profile from the subject to a proteolytic profile from a reference sample. In some embodiments, the method further comprises making an assessment of the subject based on the comparison, wherein the assessment is a diagnosis of a disease. In some embodiments, the method further comprises treating the subject based on the assessment. In some embodiments, the method further comprises treating the subject for the disease based on the assessment. In some embodiments, the disease is a cardiovascular disease.

In some embodiments, the method further comprises comparing the proteolytic profile from the subject to a proteolytic profile from a reference sample. In some embodiments, the method further comprises making an assessment of the subject based on the comparison, wherein the assessment is a prognosis of a disease. In some embodiments, the method further comprises treating the subject based on the assessment. In some embodiments, the disease is a cardiovascular disease.

In some embodiments, the method further comprises comparing the proteolytic profile from the subject to a proteolytic profile from a reference sample, wherein a difference between the proteolytic profile of the subject and the proteolytic profile of the reference sample is indicative of a cardio vascular disease.

In some embodiments, the method further comprises comparing the proteolytic profile from the subject to a proteolytic profile from a reference sample, wherein a difference between the proteolytic profile of the subject and the proteolytic profile of the reference sample is an assessment of the subject, wherein the assessment is a diagnosis of a disease. In some embodiments, the method further comprises treating the subject based on the assessment. In some embodiments, the method further comprises treating the subject for the disease based on the assessment. In some embodiments, the disease is a cardiovascular disease.

In some embodiments, the method further comprises comparing the proteolytic profile from the subject to a proteolytic profile from a reference sample, wherein a difference between the proteolytic profile of the subject and the proteolytic profile of the reference sample is an assessment of the subject, wherein the assessment is a prognosis of developing a disease. In some embodiments, the method further comprises treating the subject based on the assessment. In some embodiments, the disease is a cardiovascular disease.

In some embodiments, the method further comprises making an assessment of the subject based on the proteolytic profile, wherein the assessment is a diagnosis of a disease. In some embodiments, the method further comprises treating the subject based on the assessment. In some embodiments, the method further comprises making an assessment of the subject based on the proteolytic profile, wherein the assessment is a diagnosis of a disease; and treating the subject based on the assessment. In some embodiments, the disease is a cardiovascular disease.

In some embodiments, the method further comprises making an assessment of the subject based on the proteolytic profile, wherein the assessment is a prognosis of developing a disease. In some embodiments, the method further comprises treating the subject based on the assessment. In some embodiments, the method further comprises making an assessment of the subject based on the proteolytic profile, wherein the assessment is a prognosis of developing a disease; and treating the subject based on the assessment. In some embodiments, the disease is a cardiovascular disease.

In various embodiments, the present invention provides a method for assessing the efficacy of a treatment, comprising: comparing a proteolytic profile from a subject to a proteolytic profile from a reference sample, wherein a change in the proteolytic profile from the subject relative to the proteolytic profile from the reference sample is indicative of the efficacy of the treatment.

In some embodiments of the present invention, the reference sample is obtained from a control subject, wherein the control subject does not have a disease (e.g., a cardiovascular disease). In some embodiments of the present invention, the reference sample is obtained from the subject before the subject is treated for a disease (e.g., a cardiovascular disease). In some embodiments of the present invention, the reference sample is from a subject that has been treated for a disease (e.g., a cardiovascular disease). In some embodiments of the present invention, the reference sample is obtained from the subject at an earlier time.

Method for Diagnosing a Disease

In various embodiments, the present invention provides a method for diagnosing a disease in a subject, comprising obtaining a sample comprising one or more proteases from the subject; adding an amount of one or more L-natriuretic peptides to the sample; adding an amount of an internal standard to the sample, wherein the internal standard comprises one or more non-natural natriuretic peptides, one or more non-natural cleavage peptidoforms, or combination thereof; detecting and/or measuring an amount of one or more L-natriuretic peptide cleavage products of the one or more L-natriuretic peptides over a period of time; detecting and/or measuring an amount of the internal standard over a period of time; and quantifying the amount of one or more L-natriuretic peptide cleavage products by comparing the amount of one or more L-natriuretic peptide cleavage products with the amount of the internal standard to obtain the proteolytic profile of the subject; and comparing the proteolytic profile from the subject to a proteolytic profile from a reference sample, wherein a change in the proteolytic profile from the subject relative to the proteolytic profile from the reference sample is indicative of a disease in the subject. In some embodiments, the detecting and/or measuring of the internal standard comprises detecting and/or measuring the amount of the non-natural natriuretic peptide or the amount of the non-natural cleavage peptidoform. In some embodiments, the quantifying the amount of one or more L-natriuretic peptide cleavage products by comparing the amount of one or more L-natriuretic peptide cleavage products with the amount of the internal standard to obtain the proteolytic profile of the subject, comprises quantifying the amount of one or more L-natriuretic peptide cleavage products by comparing the amount of one or more L-natriuretic peptide cleavage products with the amount of the non-natural natriuretic peptide or the amount of the non-natural cleavage peptidoform.

Method for Assessing and/or Determining the Risk of Developing a Disease

In various embodiments, the present invention provides a method for assessing and/or determining the risk of developing a disease in a subject, comprising: obtaining a sample comprising one or more proteases from the subject; adding an amount of one or more L-natriuretic peptides to the sample; adding an amount of an internal standard to the sample, wherein the internal standard comprises one or more non-natural natriuretic peptides, one or more non-natural cleavage peptidoforms, or combination thereof; detecting and/or measuring an amount of one or more L-natriuretic peptide cleavage products of the one or more L-natriuretic peptides over a period of time; detecting and/or measuring an amount of the internal standard over a period of time; and quantifying the amount of one or more L-natriuretic peptide cleavage products by comparing the amount of one or more L-natriuretic peptide cleavage products with the amount of the internal standard to obtain the proteolytic profile of the subject; and comparing the proteolytic profile from the subject to a proteolytic profile from a reference sample, wherein a change in the proteolytic profile from the subject relative to the proteolytic profile from the reference sample is indicative of an increased risk of the subject developing the disease. In some embodiments, the detecting and/or measuring of the internal standard comprises detecting and/or measuring the amount of the non-natural natriuretic peptide or the amount of the non-natural cleavage peptidoform. In some embodiments, the quantifying the amount of one or more L-natriuretic peptide cleavage products by comparing the amount of one or more L-natriuretic peptide cleavage products with the amount of the internal standard to obtain the proteolytic profile of the subject, comprises quantifying the amount of one or more L-natriuretic peptide cleavage products by comparing the amount of one or more L-natriuretic peptide cleavage products with the amount of the non-natural natriuretic peptide or the amount of the non-natural cleavage peptidoform.

Method for Assessing and/or Determining State of Health

In various embodiments, the present invention provides a method for assessing and/or determining state of health of a subject, comprising: obtaining a sample comprising one or more proteases from the subject; adding an amount of one or more L-natriuretic peptides to the sample; adding an amount of an internal standard to the sample, wherein the internal standard comprises one or more non-natural natriuretic peptides, one or more non-natural cleavage peptidoforms, or combination thereof; detecting and/or measuring an amount of one or more L-natriuretic peptide cleavage products of the one or more L-natriuretic peptides over a period of time; detecting and/or measuring an amount of the internal standard over a period of time; and quantifying the amount of one or more L-natriuretic peptide cleavage products by comparing the amount of one or more L-natriuretic peptide cleavage products with the amount of the internal standard to obtain the proteolytic profile of the subject; comparing the proteolytic profile from the subject to a proteolytic profile from one or more reference samples; and assessing the state of health of the subject based on the comparison. In some embodiments, the detecting and/or detecting and/or measuring of the internal standard comprises detecting and/or measuring the amount of the non-natural natriuretic peptide or the amount of the non-natural cleavage peptidoform. In some embodiments, the quantifying the amount of one or more L-natriuretic peptide cleavage products by comparing the amount of one or more L-natriuretic peptide cleavage products with the amount of the internal standard to obtain the proteolytic profile of the subject, comprises quantifying the amount of one or more L-natriuretic peptide cleavage products by comparing the amount of one or more L-natriuretic peptide cleavage products with the amount of the non-natural natriuretic peptide or the amount of the non-natural cleavage peptidoform.

Method for Identifying and/or Assessing a Condition

In various embodiments, the present invention provides method for identifying and/or assessing a condition of a subject, comprising: obtaining a sample comprising one or more proteases from the subject; adding an amount of one or more L-natriuretic peptides to the sample; adding an amount of an internal standard to the sample, wherein the internal standard comprises one or more non-natural natriuretic peptides, one or more non-natural cleavage peptidoforms, or combination thereof; detecting and/or measuring an amount of one or more L-natriuretic peptide cleavage products of the one or more L-natriuretic peptides over a period of time; detecting and/or measuring an amount of the internal standard over a period of time; and quantifying the amount of one or more L-natriuretic peptide cleavage products by comparing the amount of one or more L-natriuretic peptide cleavage products with the amount of the internal standard to obtain the proteolytic profile of the subject; comparing the proteolytic profile from the subject to a proteolytic profile from one or more reference samples; and identifying and/or assessing the condition of the subject based on the comparison. In some embodiments, the detecting and/or measuring of the internal standard comprises detecting and/or measuring the amount of the non-natural natriuretic peptide or the amount of the non-natural cleavage peptidoform. In some embodiments, the quantifying the amount of one or more L-natriuretic peptide cleavage products by comparing the amount of one or more L-natriuretic peptide cleavage products with the amount of the internal standard to obtain the proteolytic profile of the subject, comprises quantifying the amount of one or more L-natriuretic peptide cleavage products by comparing the amount of one or more L-natriuretic peptide cleavage products with the amount of the non-natural natriuretic peptide or the amount of the non-natural cleavage peptidoform.

Method of Diagnosing and/or Prognosing State of Health

In various embodiments, the present invention provides a method of diagnosing and/or prognosing state of health of a subject, comprising: obtaining a sample comprising one or more proteases from the subject; adding an amount of one or more L-natriuretic peptides to the sample; adding an amount of an internal standard to the sample, wherein the internal standard comprises one or more non-natural natriuretic peptides, one or more non-natural cleavage peptidoforms, or combination thereof; detecting and/or measuring an amount of one or more L-natriuretic peptide cleavage products of the one or more L-natriuretic peptides over a period of time; detecting and/or measuring an amount of the internal standard over a period of time; and quantifying the amount of one or more L-natriuretic peptide cleavage products by comparing the amount of one or more L-natriuretic peptide cleavage products with the amount of the internal standard to obtain the proteolytic profile of the subject; comparing the proteolytic profile from the subject to a proteolytic profile from one or more reference samples; and diagnosing and/or prognosing the state of health of the subject based on the comparison. In some embodiments, the detecting and/or measuring of the internal standard comprises detecting and/or measuring the amount of the non-natural natriuretic peptide or the amount of the non-natural cleavage peptidoform. In some embodiments, the quantifying the amount of one or more L-natriuretic peptide cleavage products by comparing the amount of one or more L-natriuretic peptide cleavage products with the amount of the internal standard to obtain the proteolytic profile of the subject, comprises quantifying the amount of one or more L-natriuretic peptide cleavage products by comparing the amount of one or more L-natriuretic peptide cleavage products with the amount of the non-natural natriuretic peptide or the amount of the non-natural cleavage peptidoform.

Method of Diagnosing and/or Prognosing a Condition

In various embodiments, the present invention provides a method of diagnosing and/or prognosing a condition in subject, comprising: obtaining a sample comprising one or more proteases from the subject; adding an amount of one or more L-natriuretic peptides to the sample; adding an amount of an internal standard to the sample, wherein the internal standard comprises one or more non-natural natriuretic peptides, one or more non-natural cleavage peptidoforms, or combination thereof; detecting and/or measuring an amount of one or more L-natriuretic peptide cleavage products of the one or more L-natriuretic peptides over a period of time; detecting and/or measuring an amount of the internal standard over a period of time; and quantifying the amount of one or more L-natriuretic peptide cleavage products by comparing the amount of one or more L-natriuretic peptide cleavage products with the amount of the internal standard to obtain the proteolytic profile of the subject; comparing the proteolytic profile from the subject to a proteolytic profile from one or more reference sample; and diagnosing and/or prognosing the condition of the subject based on the comparison. In some embodiments, the detecting and/or measuring of the internal standard comprises detecting and/or measuring the amount of the non-natural natriuretic peptide or the amount of the non-natural cleavage peptidoform. In some embodiments, the quantifying the amount of one or more L-natriuretic peptide cleavage products by comparing the amount of one or more L-natriuretic peptide cleavage products with the amount of the internal standard to obtain the proteolytic profile of the subject, comprises quantifying the amount of one or more L-natriuretic peptide cleavage products by comparing the amount of one or more L-natriuretic peptide cleavage products with the amount of the non-natural natriuretic peptide or the amount of the non-natural cleavage peptidoform.

Method for Determining the Amount of L-Natriuretic Peptides and/or L-Natriuretic Peptide Cleavage Products In various embodiments, the present invention provides method for determining the amount of one or more L-natriuretic peptides and/or one or more L-natriuretic peptide cleavage products of one or more L-natriuretic peptides in a sample from a subject, the method comprising: obtaining a sample comprising one or more proteases from the subject; adding an amount of an internal standard to the sample, wherein the internal standard comprises one or more non-natural natriuretic peptides, one or more non-natural cleavage peptidoforms, or combination thereof; detecting and/or measuring an amount of one or more L-natriuretic peptides and/or one or more L-natriuretic peptide cleavage products over a period of time; detecting and/or measuring an amount of the internal standard over a period of time; and quantifying the amount of one or more L-natriuretic peptides and/or one or more L-natriuretic peptide cleavage products by comparing the amount of one or more L-natriuretic peptides and/or one or more L-natriuretic peptide cleavage products with the amount of the internal standard to determine the amount of one or more L-natriuretic peptides and/or one or more L-natriuretic peptide cleavage products. In some embodiments, the detecting and/or measuring of the internal standard comprises detecting and/or measuring the amount of the non-natural natriuretic peptide or the amount of the non-natural cleavage peptidoform.

In exemplary embodiments, the proteases are circulating proteases. In exemplary embodiments, the proteases are any one or more of neutral endopeptidase, dipeptidylpeptidase IV, insulin degrading enzyme or combination thereof. In some embodiments, the proteases are endogenous proteases. In some embodiments, the endogenous protease is selected from neutral endopeptidase, dipeptidylpeptidase IV, insulin degrading enzyme, and combinations thereof. In some embodiments, an endogenous protease is present in the sample at the point in time when the sample is obtained from the subject, and originates from the subject from which the sample was obtained.

In some embodiments, the sample is a biological sample. In some embodiments the sample is plasma, blood, or serum. In some embodiments, the sample is plasma. In some embodiments, the biological sample is plasma, blood, or serum. In some embodiments, the biological sample is plasma.

In exemplary embodiments, the quantity of one or more L-natriuretic peptides added to the sample is any one or more of about 10 ng/μL, 50 ng/μL, 75 ng/μL, 100 ng/μL, 125 ng/μL, 150 ng/μL, 175 ng/μL, 200 ng/μL, 225 ng/μL, 250 ng/μL, 275 ng/μL, 300 ng/μL, 350 ng/μL, 375 ng/μL, 400 ng/μL, 450 ng/μL, 475 ng/μL, 500 ng/μL or combinations thereof. In some embodiments, the quantity of one or more L-natriuretic peptides added to the sample is any one or more of about 50 ng/μL, 75 ng/μL, 100 ng/μL, 125 ng/μL, 150 ng/μL, 175 ng/μL, 200 ng/μL, 225 ng/μL, 250 ng/μL or combinations thereof. In some embodiments, the L-natriuretic peptide added to the sample is natural natriuretic peptide and is added in amounts described herein. In some embodiments, the L-natriuretic peptide added to the sample is cleavable synthetic natriuretic peptide and is added in amounts described herein. In some embodiments, the L-natriuretic peptide added to the sample is natural BNP and is added in amounts described herein. In some embodiments, the L-natriuretic peptide added to the sample is cleavable synthetic BNP and is added in amounts described herein. The optimum amount of the L-natriuretic peptide to be added to the sample will be apparent to a person of skill in the art.

In exemplary embodiments, the quantity of one or more internal standards (or quantity of one or more non-natural natriuretic peptides, or quantity of one or more non-natural cleavage peptidoforms) added to the sample is any one or more of about 10 ng/µL, 50 ng/µL, 75 ng/µL, 100 ng/µL, 125 ng/µL, 150 ng/µL, 175 ng/µL, 200 ng/µL, 225 ng/µL, 250 ng/µL, 275 ng/µL, 300 ng/µL, 350 ng/µL, 375 ng/µL, 400 ng/µL, 450 ng/µL, 475 ng/µL, 500 ng/µL or combinations thereof. In some embodiments, the quantity of one or more internal standards (or quantity of one or more non-natural natriuretic peptides, or quantity of one or more non-natural cleavage peptidoforms) added to the sample is any one or more of about 50 ng/µL, 75 ng/µL, 100 ng/µL, 125 ng/µL, 150 ng/µL, 175 ng/µL, 200 ng/µL, 225 ng/µL, 250 ng/µL or combinations thereof. In some embodiments, the internal standard comprises one or more non-natural natriuretic peptides, one or more non-natural cleavage peptidoforms, or combination thereof. In some embodiments, the internal standard is added in amounts described herein. In some embodiments, the non-natural natriuretic peptide is added in amounts described herein. In some embodiments, the non-natural cleavage peptidoform is added in amounts described herein. In some embodiments, the internal standard is one or more non-natural natriuretic peptides, or one or more non-natural cleavage peptidoforms, or combination thereof. In some embodiments, the non-natural peptide is non-natural BNP and is added in amounts described herein. The optimum amount of the internal standard to be added to the sample will be apparent to a person of skill in the art.

In some embodiments, the amount of internal standard and the amount of L-natriuretic peptide added to the sample is the same. In some embodiments, the amount of internal standard and the amount of L-natriuretic peptide added to the sample are different. In some embodiments, the internal standard comprises one or more non-natural natriuretic peptides, one or more non-natural cleavage peptidoforms, or combination thereof. In some embodiments, the amount of non-natural natriuretic peptide and the amount of L-natriuretic peptide added to the sample is the same. In some embodiments, the amount of non-natural natriuretic peptide and the amount of L-natriuretic peptide added to the sample are different. In some embodiments, the amount of non-natural cleavage peptidoform and the amount of L-natriuretic peptide added to the sample is the same. In some embodiments, the amount of non-natural cleavage peptidoform and the amount of L-natriuretic peptide added to the sample are different.

In exemplary embodiments, the time period over which the protease activity is determined is about 1 hour in any one or more of 1, 5, 10, 15, 20, 25 or 30 min intervals, about 2 hours in any one or more of 1, 5, 10, 15, 20, 25, 30, 40, 50 or 60 min intervals, about 3 hours in any one or more of 1, 5, 10, 15, 20, 25, 30, 40, 50, 60, 75 or 90 min intervals, about 4 hours in any one or more of 1, 5, 10, 15, 20, 25, 30, 40, 50, 60, 75, 90, 100, 110 or 120 min intervals or combinations thereof. The optimum time period will be apparent to a person of skill in the art. In some embodiments, the time period is less than 1 hour. In some embodiments, the time period is less than or equal to 1 hour. In some embodiments, the time period is about 1 hour. In some embodiments, the time period is about 2 hours. In some embodiments, the time period is about 14 hours. In some embodiments, the time period is about 15 hours. In some embodiments, the time period is up to 1 hour. In some embodiments, the time period is up to 14 hours. In some embodiments the time period is greater than 1 hour. In some embodiments, the time period is greater than 14 hours. In some embodiments, the time period is 0.5 hours to 24 hours. In some embodiments, the time period is 0.5 hours to 20 hours. In some embodiments, the time period is 0.5 hours to 15 hours.

In some embodiments, the length of the cleavage products of the L-natriuretic peptides (e.g., natural natriuretic peptides and/or cleavable synthetic natriuretic peptides) is any one or more of 28-31, 25-30, 20-25, 25-32, 15-20, 10-15, 5-10, 10-20 or 20-30 amino acids long. In some embodiments, the length of the cleavage products of the natural natriuretic peptides is any one or more of 28-31, 25-30, 20-25, 25-32, 15-20, 10-15, 5-10, 10-20 or 20-30 amino acids long. In some embodiments, the length of the cleavage products of the cleavable synthetic natriuretic peptides is any one or more of 28-31, 25-30, 20-25, 25-32, 15-20, 10-15, 5-10, 10-20 or 20-30 amino acids long.

In some embodiments, the L-natriuretic peptide is natural BNP 1-32 and the cleavage products (i.e., natural cleavage products) comprise any one or more of natural BNP 3-32, natural BNP 3-29, natural BNP 3-30, natural BNP 1-30, natural BNP 1-29, natural BNP 1-28, natural BNP 2-31, natural BNP 4-30, natural BNP 4-29, natural BNP 4-27, natural BNP 5-32, natural BNP 5-31, natural BNP 5-29, natural BNP 4-32, natural BNP 4-31, or combinations thereof, wherein each range indicates the amino acid position of mature natural BNP. For example, the full length mature natural BNP is 32 amino acids long and has amino acids 1-32. "Natural BNP 3-29" refers to the proteolytic fragment of natural BNP that has amino acids 3-29 of the full length mature natural BNP. Similarly, "natural BNP 5-32" refers to the proteolytic fragment of natural BNP that has amino acids 5-32 of the full length mature natural BNP. For example, in some embodiments, the natural BNP cleavage product can be of any length that is shorter than the natural BNP 1-32.

In some embodiments, the L-natriuretic peptide is cleavable synthetic BNP 1-32 and the cleavage products (i.e., cleavable synthetic cleavage products) comprise any one or more of cleavable synthetic BNP 3-32, cleavable synthetic BNP 3-29, cleavable synthetic BNP 3-30, cleavable synthetic BNP 1-30, cleavable synthetic BNP 1-29, cleavable synthetic BNP 1-28, cleavable synthetic BNP 2-31, cleavable synthetic BNP 4-30, cleavable synthetic BNP 4-29, cleavable synthetic BNP 4-27, cleavable synthetic BNP 5-32, cleavable synthetic BNP 5-31, cleavable synthetic BNP 5-29, cleavable synthetic BNP 4-32, cleavable synthetic BNP 4-31, or combinations thereof, wherein each range indicates the amino acid position of cleavable synthetic BNP 1-32. For example, the full length cleavable synthetic BNP is 32 amino acids long and has amino acids 1-32. "Cleavable synthetic BNP 3-29" refers to the proteolytic fragment of cleavable synthetic BNP that has amino acids 3-29 of the full length cleavable synthetic BNP 1-32. Similarly, "cleavable synthetic BNP 5-32" refers to the proteolytic fragment of cleavable synthetic BNP that has amino acids 5-32 of the full length cleavable synthetic BNP 1-32. For example, in some embodiments, the cleavable synthetic BNP cleavage product can be of any length that is within the 1-32 sequence. For example, in some embodiments, the cleavable synthetic BNP cleavage product can be of any length that is shorter than the cleavable synthetic BNP 1-32.

In some embodiments, the length of the artificially synthesized non-natural cleavage peptidoforms is any one or more of 28-31, 25-30, 20-25, 25-32, 15-20, 10-15, 5-10, 10-20 or 20-30 amino acids long or any length within the 1-32 sequence. For example, in some embodiments, the artificially synthesized non-natural cleavage peptidoform can be of any length that is shorter than the full length of non-natural BNP1-32.

In some embodiments, the non-natural natriuretic peptide is non-natural BNP 1-32.

In some embodiments, the non-natural cleavage peptidoforms comprise any one or more of non-natural BNP 3-32, non-natural BNP 3-29, non-natural BNP 3-30, non-natural BNP 1-30, non-natural BNP 1-29, non-natural BNP 1-28, non-natural BNP 2-31, non-natural BNP 4-30, non-natural BNP 4-29, non-natural BNP 4-27, non-natural BNP 5-32, non-natural BNP 5-31, non-natural BNP 5-29, non-natural BNP 4-32, non-natural BNP 4-31, or combinations thereof, wherein each range indicates the amino acid position of non-natural BNP 1-32. For example, the full length non-natural BNP is 32 amino acids long and has amino acids 1-32. "Non-natural BNP 3-29" refers to the artificially synthesized fragment of non-natural BNP1-32 that has amino acids 3-29 of the full length non-natural BNP 1-32. Similarly, "non-natural BNP 5-32" refers to the artificially synthesized fragment of non-natural BNP1-32 that has amino acids 5-32 of the full length non-natural BNP 1-32. In some embodiments, the artificially synthesized fragment of non-natural BNP1-32 can be of any length that is shorter than the full length of non-natural BNP1-32.

In some embodiments, the L-natriuretic peptides and/or the cleavage products of the L-natriuretic peptides are measured and/or quantified and/or detected using any one or more of capillary electrophoresis (CE), mass spectrometry (MS), capillary electrophoresis/electrospray ionization-mass spectrometry (CESI-MS), capillary electrophoresis-mass spectrometry (CE-MS), liquid chromatography mass spectrometry (LC-MS), high pressure liquid chromatography mass spectrometry (HPLC-MS), or combinations thereof. In some embodiments, the L-natriuretic peptide cleavage products of the L-natriuretic peptides are measured and/or quantified and/or detected using capillary electrophoresis/electrospray ionization-mass spectrometry (CESI-MS) combined with multi-segment injection (MSI).

In some embodiments, the non-natural natriuretic peptides, or artificially synthesized non-natural natriuretic peptidoforms are measured and/or quantified and/or detected using a method comprising any one or more of capillary electrophoresis (CE), mass spectrometry (MS), capillary electrophoresis/electrospray ionization-mass spectrometry (CESI-MS), capillary electrophoresis-mass spectrometry (CE-MS), liquid chromatography mass spectrometry (LC-MS), high pressure liquid chromatography mass spectrometry (HPLC-MS), or combinations thereof. In some embodiments, the non-natural natriuretic peptides, or artificially synthesized non-natural natriuretic peptidoforms are measured and/or quantified and/or detected using capillary electrophoresis/electrospray ionization-mass spectrometry (CESI-MS) combined with multi-segment injection (MSI).

In some embodiments, the reference value is the protease activity over time in a sample obtained from a healthy subject. In some embodiments, the reference value is the protease activity over time in a sample obtained from a subject that has been treated for a disease (e.g., cardiovascular disease). In further embodiments, the reference value is the protease activity over time in a sample obtained from the subject at an earlier time point. In some embodiments, the protease activity in a subject having or suspected of having a disease (e.g., cardiovascular disease) is compared to the reference value is increased by at least or about 10%, 20%, 30%, 40%, 50%, 60%, 70%, 80%, 90% or 100%. In some embodiments, the protease activity in a subject having or suspected of having a disease (e.g., cardiovascular disease) is compared to the reference value is increased by at least or about 1-fold, 2-fold, 3-fold, 4-fold, 5-fold, 10-fold, 15-fold, 20-fold, 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, 100-fold or a combination thereof.

Method for the Quantitative Profiling of L-Natriuretic Peptides and/or L-Natriuretic Peptide Cleavage Products In various embodiments, the present invention provides a method for the quantitative profiling of one or more L-natriuretic peptides and/or one or more L-natriuretic peptide cleavage products in a sample from a subject, comprising obtaining a sample comprising one or more proteases from the subject; adding an amount of one or more L-natriuretic peptides to the sample; adding an amount of an internal standard to the sample, wherein the internal standard comprises one or more non-natural natriuretic peptides, one or more non-natural cleavage peptidoforms, or combination thereof; detecting and/or measuring an amount of one or more L-natriuretic peptide cleavage products of the one or more L-natriuretic peptides over a period of time; detecting and/or measuring an amount of the internal standard over a period of time; and quantifying the amount of one or more L-natriuretic peptide cleavage products by comparing the amount of one or more L-natriuretic peptide cleavage products with the amount of the internal standard to obtain the proteolytic profile of the subject. In some embodiments, the detecting and/or measuring of the internal standard comprises detecting and/or measuring the amount of the non-natural natriuretic peptide or the amount of the non-natural cleavage peptidoform. In some embodiments, the quantifying the amount of one or more L-natriuretic peptide cleavage products by comparing the amount of one or more L-natriuretic peptide cleavage products with the amount of the internal standard to obtain the proteolytic profile of the subject, comprises quantifying the amount of one or more L-natriuretic peptide cleavage products by comparing the amount of one or more L-natriuretic peptide cleavage products with the amount of the non-natural natriuretic peptide or the amount of the non-natural cleavage peptidoform.

Method for Determining the Stability of Endogenous L-Natriuretic Peptides

In various embodiments, the present invention provides a method for determining the stability of endogenous L-natriuretic peptides in a sample from a subject, comprising obtaining a sample comprising one or more proteases from the subject; adding an amount of an internal standard to the sample, wherein the internal standard comprises one or more non-natural natriuretic peptides, one or more non-natural cleavage peptidoforms, or combination thereof; detecting and/or measuring an amount of one or more L-natriuretic peptide cleavage products of the one or more endogenous L-natriuretic peptides over a period of time; detecting and/or measuring an amount of the internal standard over a period of time; and quantifying the amount of one or more L-natriuretic peptide cleavage products by comparing the amount of one or more L-natriuretic peptide cleavage products with the amount of the internal standard to determine the stability of endogenous L-natriuretic peptides in a sample. In some embodiments, the endogenous L-natriuretic peptide is BNP1-32. In some embodiments, the detecting and/or measuring of the internal standard comprises detecting and/or measuring the amount of the non-natural natriuretic peptide or the amount of the non-natural cleavage peptidoform. In some embodiments, the amount of the endogenous L-natriuretic peptide is detected and/or measured, and the amount of the endogenous L-natriuretic peptide is quantified by comparing the amount of the endogenous L-natriuretic peptide with the amount of the internal standard.

Method for Detecting and/or Measuring and/or Quantifying Endogenous Natural Natriuretic Peptides and/or Cleavage Products of the Endogenous Natural Natriuretic Peptides In various embodiments, the present invention provides a method for detecting and/or measuring and/or quantifying one or more endogenous natural natriuretic peptides and/or one or more cleavage products of the endogenous natural natriuretic peptides in a sample from a subject, comprising obtaining a sample from the subject; adding an amount of an internal standard to the sample, wherein the internal standard comprises one or more non-natural natriuretic peptides, one or more non-natural cleavage peptidoforms, or combination thereof; detecting and/or measuring an amount of the endogenous natural natriuretic peptide and/or one or more cleavage products of the endogenous natural natriuretic peptide over a period of time; detecting and/or measuring an amount of the internal standard over a period of time; and quantifying the amount of the endogenous natural natriuretic peptide and/or one or more cleavage products of the endogenous natural natriuretic peptide by comparing the amount of endogenous natural natriuretic peptide and/or one or more cleavage products of the endogenous natural natriuretic peptide with the amount of the internal standard in the sample. In some embodiments, the endogenous natural natriuretic peptide is natural BNP1-32. In some embodiments, the detecting and/or measuring of the internal standard comprises detecting and/or measuring the amount of the non-natural natriuretic peptide or the amount of the non-natural cleavage peptidoform. In some embodiments, the non-natural natriuretic peptide is D-BNP. In some embodiments, the endogenous natural natriuretic peptide and/or one or more cleavage products of the endogenous natural natriuretic peptide are enriched using an antibody (or any enrichment method or capture method). In one non-limiting example, the enrichment is performed using an anti-antibody to the loop or central region that is common to the endogenous natural natriuretic peptide and/or one or more cleavage products of the endogenous natural natriuretic peptide that are produced in vivo. In some embodiments, the quantification of the endogenous natural natriuretic peptide and/or one or more cleavage products of the endogenous natural natriuretic peptide is performed by adding in one or more non-natural natriuretic peptides, one or more non-natural cleavage peptidoforms, or combination thereof prior to enrichment of the endogenous natural natriuretic peptide and/or one or more cleavage products of the endogenous natural natriuretic peptide. In some embodiments, the endogenous natural natriuretic peptide, one or more cleavage products of the endogenous natural natriuretic peptide, one or more non-natural natriuretic peptides, and/or one or more non-natural cleavage peptidoforms are analyzed and/or detected and/or measured and/or quantified using mass spectrometry.

Method for Identifying L-Natriuretic Peptide Cleavage Products

In various embodiments, the present invention provides a method for identifying one or more L-natriuretic peptide cleavage products, comprising: obtaining a sample comprising one or more proteases from the subject; adding an amount of one or more L-natriuretic peptides to the sample; adding an amount of an internal standard to the sample, wherein the internal standard comprises one or more non-natural natriuretic peptides, one or more non-natural cleavage peptidoforms, or combination thereof; detecting and/or measuring an amount of one or more L-natriuretic peptide cleavage products of the one or more L-natriuretic peptides over a period of time; detecting and/or measuring an amount of the internal standard over a period of time; and quantifying the amount of one or more L-natriuretic peptide cleavage products by comparing the amount of one or more L-natriuretic peptide cleavage products with the amount of the internal standard to obtain the proteolytic profile of the subject; and comparing the proteolytic profile from the subject to a proteolytic profile from one or more reference samples to identify one or more L-natriuretic peptide cleavage products in the sample. In some embodiments, the detecting and/or measuring of the internal standard comprises detecting and/or measuring the amount of the non-natural natriuretic peptide or the amount of the non-natural cleavage peptidoform. In some embodiments, the quantifying the amount of one or more L-natriuretic peptide cleavage products by comparing the amount of one or more L-natriuretic peptide cleavage products with the amount of the internal standard to obtain the proteolytic profile of the subject, comprises quantifying the amount of one or more L-natriuretic peptide cleavage products by comparing the amount of one or more L-natriuretic peptide cleavage products with the amount of the non-natural natriuretic peptide or the amount of the non-natural cleavage peptidoform.

Method for Monitoring and/or Determining Progression of Cardiovascular Disease

In various embodiments, the present invention provides a method for monitoring and/or determining progression of cardiovascular disease in a subject, the method comprising: obtaining a sample from the subject, wherein the sample comprises one or more proteases; adding an amount of one or more L-natriuretic peptides to the sample; adding an amount of an internal standard to the sample, wherein the internal standard comprises one or more non-natural natriuretic peptides, one or more non-natural cleavage peptidoforms, or combination thereof; detecting and/or measuring an amount of one or more L-natriuretic peptide cleavage products of the one or more L-natriuretic peptides over a period of time; detecting and/or measuring an amount of the internal standard over a period of time; quantifying the amount of one or more L-natriuretic peptide cleavage products by comparing the amount of one or more L-natriuretic peptide cleavage products with the amount of the internal standard to obtain the proteolytic profile of the subject; and comparing the proteolytic profile from the subject to a proteolytic profile from a reference sample, wherein a change in the proteolytic profile from the subject relative to the proteolytic profile from the reference sample is indicative of progression of cardiovascular disease in the subject. In some embodiments, the method further comprises administering a treatment to the subject. In some embodiments, the method further comprises assessing the efficacy of the treatment, comprising: obtaining a post treatment sample from the subject; obtaining a post treatment proteolytic profile for the post treatment sample from the subject; comparing the proteolytic profile from the subject before administration of the treatment to the post treatment proteolytic profile from the post treatment sample, wherein a change in the post treatment proteolytic profile from the post treatment sample relative to the proteolytic profile from the subject before administration of the treatment is indicative of the efficacy of the treatment. In some embodiments, the subject is selected from the group consisting of a subject that has cardiovascular disease, and a subject that has been diagnosed with cardiovascular disease.

Method for Monitoring and/or Determining Progression of a Disease

In various embodiments, the present invention provides a method for monitoring and/or determining progression of a disease in a subject, the method comprising: obtaining a sample from the subject, wherein the sample comprises one or more proteases; adding an amount of one or more L-natriuretic peptides to the sample; adding an amount of an internal standard to the sample, wherein the internal standard comprises one or more non-natural natriuretic peptides, one or more non-natural cleavage peptidoforms, or combination thereof; detecting and/or measuring an amount of one or more L-natriuretic peptide cleavage products of the one or more L-natriuretic peptides over a period of time; detecting and/or measuring an amount of the internal standard over a period of time; quantifying the amount of one or more L-natriuretic peptide cleavage products by comparing the amount of one or more L-natriuretic peptide cleavage products with the amount of the internal standard to obtain the proteolytic profile of the subject; and comparing the proteolytic profile from the subject to a proteolytic profile from a reference sample, wherein a change in the proteolytic profile from the subject relative to the proteolytic profile from the reference sample is indicative of progression of the disease in the subject. In some embodiments, the method further comprises administering a treatment to the subject. In some embodiments, the method further comprises assessing the efficacy of the treatment, comprising: obtaining a post treatment sample from the subject; obtaining a post treatment proteolytic profile for the post treatment sample from the subject; comparing the proteolytic profile from the subject before administration of the treatment to the post treatment proteolytic profile from the post treatment sample, wherein a change in the post treatment proteolytic profile from the post treatment sample relative to the proteolytic profile from the subject before administration of the treatment is indicative of the efficacy of the treatment. In some embodiments, the subject is selected from the group consisting of a subject that has the disease, and a subject that has been diagnosed with the disease.

Method for Determining a Treatment Course of Action

In various embodiments, the present invention provides a method for determining a treatment course of action for a subject, the method comprising: obtaining a sample from the subject, wherein the sample comprises one or more proteases; adding an amount of one or more L-natriuretic peptides to the sample; adding an amount of an internal standard to the sample, wherein the internal standard comprises one or more non-natural natriuretic peptides, one or more non-natural cleavage peptidoforms, or combination thereof; detecting and/or measuring an amount of one or more L-natriuretic peptide cleavage products of the one or more L-natriuretic peptides over a period of time; detecting and/or measuring an amount of the internal standard over a period of time; quantifying the amount of one or more L-natriuretic peptide cleavage products by comparing the amount of one or more L-natriuretic peptide cleavage products with the amount of the internal standard to obtain the proteolytic profile of the subject; comparing the proteolytic profile from the subject to a proteolytic profile from a reference sample; and determining a treatment course of action based on the proteolytic profile from the subject and/or comparison to the proteolytic profile from the reference sample.

Method for Monitoring a Response to a Treatment

A method for monitoring a response to a treatment administered to a subject, comprising: obtaining a sample from the subject, wherein the sample comprises one or more proteases; adding an amount of one or more L-natriuretic peptides to the sample; adding an amount of an internal standard to the sample, wherein the internal standard comprises one or more non-natural natriuretic peptides, one or more non-natural cleavage peptidoforms, or combination thereof; detecting and/or measuring an amount of one or more L-natriuretic peptide cleavage products of the one or more L-natriuretic peptides over a period of time; detecting and/or measuring an amount of the internal standard over a period of time; quantifying the amount of one or more L-natriuretic peptide cleavage products by comparing the amount of one or more L-natriuretic peptide cleavage products with the amount of the internal standard to obtain the proteolytic profile of the subject; comparing the amount of the one or more L-natriuretic peptides in the sample over time, wherein a change in the amount of the one or more L-natriuretic peptides after treatment compared to the amount of the one or more L-natriuretic peptides before treatment is indicative of a favorable response to the treatment.

Method for Determining an Effect of a Treatment

A method for determining an effect of a treatment for a disease, the method comprising: obtaining a sample from the subject, wherein the sample comprises one or more proteases, and the subject has the disease and has been treated with the treatment; adding an amount of one or more L-natriuretic peptides to the sample; adding an amount of an internal standard to the sample, wherein the internal standard comprises one or more non-natural natriuretic peptides, one or more non-natural cleavage peptidoforms, or combination thereof; detecting and/or measuring an amount of one or more L-natriuretic peptide cleavage products of the one or more L-natriuretic peptides over a period of time; detecting and/or measuring an amount of the internal standard over a period of time; quantifying the amount of one or more L-natriuretic peptide cleavage products by comparing the amount of one or more L-natriuretic peptide cleavage products with the amount of the internal standard; comparing the amount of the one or more L-natriuretic peptide cleavage products in the sample from the subject to an amount of the one or more L-natriuretic peptide cleavage products in a reference sample; and determining that the treatment is effective when there is a change in the amount of the one or more L-natriuretic peptide cleavage products in the sample form the subject compared to the amount of the one or more L-natriuretic peptide cleavage products in the reference sample.

Method for Diagnosing and Treating a Disease

In various embodiments, the present invention provides a method for diagnosing and treating a disease in a subject, comprising obtaining a sample comprising one or more proteases from the subject; adding an amount of one or more L-natriuretic peptides to the sample; adding an amount of an internal standard to the sample, wherein the internal standard comprises one or more non-natural natriuretic peptides, one or more non-natural cleavage peptidoforms, or combination thereof; detecting and/or measuring an amount of one or more L-natriuretic peptide cleavage products of the one or more L-natriuretic peptides over a period of time; detecting and/or measuring an amount of the internal standard over a period of time; and quantifying the amount of one or more L-natriuretic peptide cleavage products by comparing the amount of one or more L-natriuretic peptide cleavage products with the amount of the internal standard to obtain the proteolytic profile of the subject; comparing the proteolytic profile from the subject to a proteolytic profile from a reference sample, wherein a change in the proteolytic profile from the subject relative to the proteolytic profile from the reference sample is indicative of and/or a diagnosis of the disease in the subject; and administering a treatment to the subject. In some embodiments, the detecting and/or measuring of the internal standard comprises detecting and/or measuring the amount of the non-natural natriuretic peptide or the amount of the non-natural cleavage peptidoform. In some embodiments, the quantifying the amount of one or more L-natriuretic peptide cleavage products by comparing the amount of one or more L-natriuretic peptide cleavage products with the amount of the internal standard to obtain the proteolytic profile of the subject, comprises quantifying the amount of one or more L-natriuretic peptide cleavage products by comparing the amount of one or more L-natriuretic peptide cleavage products with the amount of the non-natural natriuretic peptide or the amount of the non-natural cleavage peptidoform.

In some embodiments, the disease is cardiovascular disease. In some embodiments, the treatment and/or therapy is selected from the group consisting of cholesterol-lowering agent, glucose-lowering agent, lipid-lowering agent, fat/adipose tissue mass-lowering agent, blood pressure lowering agent, dietary therapy, physical therapy, behavior therapy, drug therapy, and combinations thereof.

In some embodiments, the disease is cancer. In some embodiments, the treatment and/or therapy is selected from the group consisting of pharmacological therapy, biological therapy, cell therapy, gene therapy, chemotherapy, radiation therapy, hormonal therapy, surgery, immunotherapy, brachytherapy, and combinations thereof.

In some embodiments, chemotherapy and/or chemotherapeutic agents may be selected from any one or more of cytotoxic antibiotics, antimetabolites, anti-mitotic agents, alkylating agents, arsenic compounds, DNA topoisomerase inhibitors, taxanes, nucleoside analogues, plant alkaloids, and toxins; and synthetic derivatives thereof. Exemplary compounds include, but are not limited to, alkylating agents: treosulfan, and trofosfamide; plant alkaloids: vinblastine, paclitaxel, docetaxol; DNA topoisomerase inhibitors: doxorubicin, epirubicin, etoposide, camptothecin, topotecan, irinotecan, teniposide, crisnatol, and mitomycin; anti-folates: methotrexate, mycophenolic acid, and hydroxyurea; pyrimidine analogs: 5-fluorouracil, doxifluridine, and cytosine arabinoside; purine analogs: mercaptopurine and thioguanine; DNA antimetabolites: 2'-deoxy-5-fluorouridine, aphidicolin glycinate, and pyrazoloimidazole; and antimitotic agents: halichondrin, colchicine, and rhizoxin. Compositions comprising one or more chemotherapeutic agents (e.g., FLAG, CHOP) may also be used. FLAG comprises fludarabine, cytosine arabinoside (Ara-C) and G-CSF. CHOP comprises cyclophosphamide, vincristine, doxorubicin, and prednisone. In another embodiment, PARP (e.g., PARP-1 and/or PARP-2) inhibitors are used and such inhibitors are well known in the art (e.g., Olaparib, ABT-888, BSI-201, BGP-15 (N-Gene Research Laboratories, Inc.); INO-1001 (Inotek Pharmaceuticals Inc.); PJ34 (Soriano et al., 2001; Pacher et al., 2002b); 3-aminobenzamide (Trevigen); 4-amino-1,8-naphthalimide; (Trevigen); 6(5H)-phenanthridinone (Trevigen); benzamide (U.S. Pat. Re. 36,397); Abraxane; gemcitabine; and NU1025 (Bowman et al.).

In various embodiments, radiation therapy can be ionizing radiation. Radiation therapy can also be gamma rays, X-rays, or proton beams. Examples of radiation therapy include, but are not limited to, external-beam radiation therapy, interstitial implantation of radioisotopes (I-125, palladium, iridium), radioisotopes such as strontium-89, thoracic radiation therapy, intraperitoneal P-32 radiation therapy, and/or total abdominal and pelvic radiation therapy. For a general overview of radiation therapy, see Hellman, Chapter 16: Principles of Cancer Management: Radiation Therapy, 6th edition, 2001, DeVita et al., eds., J. B. Lippencott Company, Philadelphia. The radiation therapy can be administered as external beam radiation or tele-therapy wherein the radiation is directed from a remote source. The radiation treatment can also be administered as internal therapy or brachytherapy wherein a radioactive source is placed inside the body close to cancer cells or a tumor mass. Also encompassed is the use of photodynamic therapy comprising the administration of photosensitizers, such as hematoporphyrin and its derivatives, Vertoporfin (BPD-MA), phthalocyanine, photosensitizer Pc4, demethoxy-hypocrellin A; and 2BA-2-DMHA.

In various embodiments, immunotherapy may comprise, for example, use of cancer vaccines and/or sensitized antigen presenting cells. In some embodiments, therapies include targeting cells in the tumor microenvironment or targeting immune cells. The immunotherapy can involve passive immunity for short-term protection of a host, achieved by the administration of pre-formed antibody directed against a cancer antigen or disease antigen (e.g., administration of a monoclonal antibody, optionally linked to a chemotherapeutic agent or toxin, to a tumor antigen). Immunotherapy can also focus on using the cytotoxic lymphocyte-recognized epitopes of cancer cell lines or tumor-associated macrophages and combinations thereof. Immunotherapy can also include methods that alter the immune microenvironment using agents that alter cytokines, chemokines.

In various embodiments, hormonal therapy can include, for example, hormonal agonists, hormonal antagonists (e.g., flutamide, bicalutamide, tamoxifen, raloxifene, leuprolide acetate (LUPRON), LH-RH antagonists), inhibitors of hormone biosynthesis and processing, and steroids (e.g., dexamethasone, retinoids, deltoids, betamethasone, cortisol, cortisone, prednisone, dehydrotestosterone, glucocorticoids, mineralocorticoids, estrogen, testosterone, progestins), vitamin A derivatives (e.g., all-trans retinoic acid (ATRA)); vitamin D3 analogs; antigestagens (e.g., mifepristone, onapristone), or antiandrogens (e.g., cyproterone acetate).

Method for Treating a Disease in a Subject

A method for treating a disease in a subject in whom the presence of one or more cleavage products has been detected, comprising: providing a subject diagnosed with the disease in whom the presence of one or more cleavage products has been detected; and administering a treatment to the subject.

Systems and Computers

In various embodiments, the present invention provides a system for obtaining a proteolytic profile of a subject, comprising: a mass spectrometer configured for acquiring mass spectrometry (MS) data on one or more cleavage products derived from one or more natriuretic peptides in a sample from the subject, wherein the sample comprises one or more natriuretic peptides and one or more proteases; and a computer configured for using the MS data to measure or quantify the amount of one or more cleavage products formed in the sample over a period of time; and for identifying the one or more cleavage products so as to obtain the proteolytic profile of the subject, wherein the mass spectrometer and the computer are connected via a communication link.

In some embodiments, the computer comprises a memory configured for storing a program; and a processor configured for executing the program, wherein the program comprises instructions for using the MS data to measure or quantify the amount of one or more cleavage products formed in the sample over a period of time; and for identifying the one or more cleavage products so as to obtain the proteolytic profile of the subject.

A non-transitory computer-readable storage medium, wherein the non-transitory computer-readable storage medium is configured for storing a program, wherein the program is configured for execution by a processor of a computer, and wherein the program comprises instructions for using mass spectrometry (MS) data to measure or quantify the amount of one or more cleavage products derived from one or more natriuretic peptides in a sample from a subject over a period of time; and for identifying the one or more cleavage products, wherein the sample from the subject comprises one or more natriuretic peptides and one or more proteases.

A computer, comprising: a memory configured for storing a program; and a processor configured for executing the program, wherein the program comprises instructions for processing mass spectrometry (MS) data to measure or quantify the amount of one or more cleavage products derived from one or more natriuretic peptides in a sample from a subject over a period of time; and for identifying the one or more cleavage products, wherein the sample from the subject comprises one or more natriuretic peptides and one or more proteases.

A computer implemented method, comprising providing a computer, wherein the computer comprises a memory configured for storing a program; and a processor configured for executing the program, wherein the program comprises instructions for processing mass spectrometry (MS) data to measure or quantify the amount of one or more cleavage products derived from one or more natriuretic peptides in a sample from a subject over a period of time; and for identifying the one or more cleavage products, wherein the sample from the subject comprises one or more natriuretic peptides and one or more proteases; inputting MS data into the computer; and operating the computer to process the MS data to measure or quantify the amount of one or more cleavage products derived from one or more natriuretic peptides in the sample over a period of time; and for identifying the one or more cleavage products.

In various embodiments, the present invention provides a system for obtaining a proteolytic profile of a subject, comprising: a mass spectrometer configured for acquiring mass spectrometry (MS) data on one or more L-natriuretic peptide cleavage products derived from one or more L-natriuretic peptides in a sample from the subject, wherein the sample comprises one or more L-natriuretic peptides, an internal standard, and one or more proteases, wherein the internal standard comprises one or more non-natural natriuretic peptides, one or more non-natural cleavage peptidoforms, or combination thereof; and a computer configured for using the MS data to measure or quantify the amount of one or more L-natriuretic peptide cleavage products formed in the sample over a period of time; and for identifying the one or more L-natriuretic peptide cleavage products so as to obtain the proteolytic profile of the subject, wherein the mass spectrometer and the computer are connected via a communication link.

In some embodiments, the computer comprises a memory configured for storing a program; and a processor configured for executing the program, wherein the program comprises instructions for using the MS data to measure or quantify the amount of L-natriuretic peptide or one or more L-natriuretic peptide cleavage products formed in the sample over a period of time relative to the internal standard; and for identifying the one or more L-natriuretic peptide cleavage products so as to obtain the proteolytic profile of the subject.

In various embodiments, the present invention provides non-transitory computer-readable storage medium, wherein the non-transitory computer-readable storage medium is configured for storing a program, wherein the program is configured for execution by a processor of a computer, and wherein the program comprises instructions for using mass spectrometry (MS) data to measure or quantify the amount of L-natriuretic peptide or one or more L-natriuretic peptide cleavage products derived from one or more L-natriuretic peptides in a sample from a subject over a period of time relative to the internal standard; and for identifying the one or more L-natriuretic peptide cleavage products, wherein the sample from the subject comprises one or more L-natriuretic peptides, an internal standard, and one or more proteases, wherein the internal standard comprises one or more non-natural natriuretic peptides, one or more non-natural cleavage peptidoforms, or combination thereof.

In various embodiments, the present invention provides a computer, comprising: a memory configured for storing a program; and a processor configured for executing the program, wherein the program comprises instructions for processing mass spectrometry (MS) data to measure or quantify the amount of L-natriuretic peptide or one or more L-natriuretic peptide cleavage products derived from one or more L-natriuretic peptides in a sample from a subject over a period of time relative to an internal standard; and for identifying the one or more L-natriuretic peptide cleavage products, wherein the sample from the subject comprises one or more L-natriuretic peptides, an internal standard, and one or more proteases, wherein the internal standard comprises one or more non-natural natriuretic peptides, one or more non-natural cleavage peptidoforms, or combination thereof.

In various embodiments, the present invention provides a computer implemented method, comprising providing a computer, wherein the computer comprises a memory configured for storing a program; and a processor configured for executing the program, wherein the program comprises instructions for processing mass spectrometry (MS) data to measure or quantify the amount of L-natriuretic peptides or one or more L-natriuretic peptide cleavage products derived from one or more L-natriuretic peptides in a sample from a subject over a period of time relative to an internal standard; and for identifying the one or more L-natriuretic peptide cleavage products, wherein the sample from the subject comprises one or more L-natriuretic peptides, an internal standard, and one or more proteases, wherein the internal standard comprises one or more non-natural natriuretic peptides, one or more non-natural cleavage peptidoforms, or combination thereof; inputting MS data into the computer; and operating the computer to process the MS data to measure or quantify the amount of L-natriuretic peptides, one or more L-natriuretic peptide cleavage products derived from one or more L-natriuretic peptides in the sample over a period of time relative to the internal standard; and for identifying the one or more L-natriuretic peptide cleavage products.

In accordance with the present invention, a "communication link," as used in this disclosure, means a wired and/or wireless medium that conveys data or information between at least two points. The wired or wireless medium may include, for example, a metallic conductor link, a radio frequency (RF) communication link, an Infrared (IR) communication link, an optical communication link, or the like, without limitation. The RF communication link may include, for example, WiFi, WiMAX, IEEE 802.11, DECT, 0G, 1G, 2G, 3G or 4G cellular standards, Bluetooth, and the like.

Computers and computing devices typically include a variety of media, which can include computer-readable storage media and/or communications media, in which these two terms are used herein differently from one another as follows.

Computer-readable storage media can be any available storage media that can be accessed by the computer, is typically of a non-transitory nature, and can include both volatile and nonvolatile media, removable and non-removable media. By way of example, and not limitation, computer-readable storage media can be implemented in connection with any method or technology for storage of information such as computer-readable instructions, program modules, structured data, or unstructured data. Computer-readable storage media can include, but are not limited to, RAM, ROM, EEPROM, flash memory or other memory technology, CD-ROM, digital versatile disk (DVD) or other optical disk storage, magnetic cassettes, magnetic tape, magnetic disk storage or other magnetic storage devices, or other tangible and/or non-transitory media which can be used to store desired information. Computer-readable storage media can be accessed by one or more local or remote computing devices, e.g., via access requests, queries or other data retrieval protocols, for a variety of operations with respect to the information stored by the medium.

On the other hand, communications media typically embody computer-readable instructions, data structures, program modules or other structured or unstructured data in a data signal that can be transitory such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

Stored on any one or on a combination of computer readable media, the exemplary embodiments of the present disclosure may include software for controlling the devices and subsystems of the exemplary embodiments, for driving the devices and subsystems of the exemplary embodiments, for enabling the devices and subsystems of the exemplary embodiments to interact with a human user, and the like. Such software can include, but is not limited to, device drivers, firmware, operating systems, development tools, applications software, database management software, and the like. Computer code devices of the exemplary embodiments can include any suitable interpretable or executable code mechanism, including but not limited to scripts, interpretable programs, dynamic link libraries (DLLs), Java classes and applets, complete executable programs, and the like. Moreover, processing capabilities may be distributed across multiple processors for better performance, reliability, cost, or other benefits.

To provide aspects of the present disclosure, embodiments may employ any number of programmable processing devices that execute software or stored instructions. Physical processors and/or machines employed by embodiments of the present disclosure for any processing or evaluation may include one or more networked (Internet, cloud, WAN, LAN, satellite, wired or wireless (RF, cellular, WiFi, Bluetooth, etc.)) or non-networked general purpose computer systems, microprocessors, filed programmable gate arrays (FPGAs), digital signal processors (DSPs), micro-controllers, smart devices (e.g., smart phones), computer tablets, handheld computers, and the like, programmed according to the teachings of the exemplary embodiments. In addition, the devices and subsystems of the exemplary embodiments can be implemented by the preparation of application-specific integrated circuits (ASICs) or by interconnecting an appropriate network of conventional component circuits. Thus, the exemplary embodiments are not limited to any specific combination of hardware circuitry and/or software.

Kits

In various embodiments, the present invention provides a kit for assessing risk of cardiovascular disease in a subject in need thereof. The kit comprises components to assess the risk of cardiovascular disease in the subject and instructions for use.

The exact nature of the components configured in the inventive kit depends on its intended purpose. In one embodiment, the kit is configured particularly for human subjects. In further embodiments, the kit is configured for veterinary applications, treating subjects such as, but not limited to, farm animals, domestic animals, and laboratory animals. In further embodiments, the kit is configured for research and/or veterinary applications, treating subjects such as, but not limited to, farm animals, domestic animals, and laboratory animals (e.g., mouse or mice).

Instructions for use may be included in the kit. "Instructions for use" typically include a tangible expression describing the technique to be employed in using the components of the kit to effect a desired outcome, such as to assess the risk of cardiovascular disease in a subject. Optionally, the kit also contains other useful components, such as, measuring tools, diluents, buffers, pharmaceutical compositions, pharmaceutically acceptable carriers, syringes or other useful paraphernalia as will be readily recognized by those of skill in the art.

The materials or components assembled in the kit can be provided to the practitioner stored in any convenient and suitable ways that preserve their operability and utility. For example, the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well-known methods, preferably to provide a sterile, contaminant-free environment. As used herein, the term "package" refers to a suitable solid matrix or material such as glass, plastic, paper, foil, and the like, capable of holding the individual kit components. The packaging material generally has an external label which indicates the contents and/or purpose of the kit and/or its components.

In various embodiments, the present invention provides a kit for identifying a subject at risk of developing a cardiovascular disease, the kit comprising one or more natriuretic peptides. In some embodiments, the kit further comprises instructions for using the kit to identify whether the subject is at risk of developing the cardiovascular disease.

In various embodiments, the present invention provides a kit for obtaining a proteolytic profile of one or more cleavage products of one or more natriuretic peptides for a subject, the kit comprising one or more natriuretic peptides. In some embodiments, the kit further comprises instructions for using the kit to obtain the proteolytic profile of the subject.

In various embodiments, the present invention provides a kit, comprising: an internal standard, wherein the internal standard comprises one or more non-natural natriuretic peptides, or one or more non-natural cleavage peptidoforms, or combination thereof; and instructions for using the kit. In some embodiments, the kit further comprises one or more L-natriuretic peptides. In some embodiments, the kit further comprises one or more L-natriuretic peptide cleavage peptidoforms. In some embodiments, the kit further comprises reagents and instructions for sample processing and preparation. In some embodiments, the non-natural natriuretic peptide is isotopically labeled. In some embodiments, the non-natural natriuretic peptide is not isotopically labeled. In some embodiments, the amount of the non-natural natriuretic peptide and the amount of the L-natriuretic peptide is the same. In some embodiments, the amount of the non-natural cleavage peptidoform and the L-natriuretic peptide is the same. In some embodiments, the amount of the non-natural natriuretic peptide and the amount of the L-natriuretic peptide is different. In some embodiments, the amount of the non-natural cleavage peptidoform and the L-natriuretic peptide is the different.

In various embodiments, the present invention provides a kit, comprising: an internal standard, wherein the internal standard comprises one or more non-natural natriuretic peptides, or one or more non-natural cleavage peptidoforms, or combination thereof; one or more L-natriuretic peptides; and instructions for using the kit. In some embodiments, the kit further comprises one or more L-natriuretic peptide cleavage peptidoforms. In some embodiments, the kit further comprises reagents and instructions for sample processing and preparation. In some embodiments, the non-natural natriuretic peptide is isotopically labeled. In some embodiments, the non-natural natriuretic peptide is not isotopically labeled. In some embodiments, the amount of the non-natural natriuretic peptide and the amount of the L-natriuretic peptide is the same. In some embodiments, the amount of the non-natural cleavage peptidoform and the L-natriuretic peptide is the same. In some embodiments, the amount of the non-natural natriuretic peptide and the amount of the L-natriuretic peptide is different. In some embodiments, the amount of the non-natural cleavage peptidoform and the L-natriuretic peptide is the different.

Kit for Obtaining a Proteolytic Profile

A kit for obtaining a proteolytic profile from a sample comprising: (a) an internal standard, wherein the internal standard comprises one or more non-natural natriuretic peptides, wherein the non-natural natriuretic peptides comprise one or more D-amino acids; (b) one or more L-natriuretic peptides; and (c) instructions for using the kit to obtain the proteolytic profile for the sample. In some embodiments, the kit further comprises one or more L-natriuretic peptide cleavage peptidoforms. In some embodiments, the kit further comprises reagents and instructions for sample processing and preparation. In some embodiments, the non-natural natriuretic peptide is isotopically labeled. In some embodiments, the non-natural natriuretic peptide is not isotopically labeled. In some embodiments, the amount of the non-natural natriuretic peptide and the amount of the L-natriuretic peptide is the same. In some embodiments, the amount of the non-natural cleavage peptidoform and the L-natriuretic peptide is the same. In some embodiments, the amount of the non-natural natriuretic peptide and the amount of the L-natriuretic peptide is different. In some embodiments, the amount of the non-natural cleavage peptidoform and the L-natriuretic peptide is the different.

In various embodiments, the present invention provides a kit for obtaining a proteolytic profile of one or more cleavage products of one or more L-natriuretic peptides for a subject, the kit comprising one or more L-natriuretic peptides; and an internal standard, wherein the internal standard comprises one or more non-natural natriuretic peptides, or one or more non-natural cleavage peptidoforms, or combination thereof. In some embodiments, the kit further comprises instructions for using the kit to obtain the proteolytic profile of the subject. In some embodiments, the kit further comprises reagents and instructions for sample processing and preparation. In some embodiments, the kit further comprises reagents and instructions for sample processing and preparation. In some embodiments, the non-natural natriuretic peptide is isotopically labeled. In some embodiments, the non-natural natriuretic peptide is not isotopically labeled.

Kit for Identifying and/or Assessing a Condition

In various embodiments, the present invention provides a kit for identifying and/or assessing a condition of a subject, the kit comprising: (a) an internal standard, wherein the internal standard comprises one or more non-natural natriuretic peptides, wherein the non-natural natriuretic peptides comprise one or more D-amino acids; (b) one or more L-natriuretic peptides; (c) reagents and instructions for sample processing and preparation; (d) instructions for using the kit to obtain a proteolytic profile for the subject; (e) one or more reference proteolytic profiles characteristic for one or more diseases; and (f) instructions for using the kit to identify and/or assess the condition of the subject.

Kit for Assessing and/or Determining State of Health

In various embodiments, the present invention provides a kit for assessing and/or determining state of health of a subject, the kit comprising: (a) an internal standard, wherein the internal standard comprises one or more non-natural natriuretic peptides, wherein the non-natural natriuretic peptides comprise one or more D-amino acids; (b)) one or more L-natriuretic peptides; (c) reagents and instructions for sample processing and preparation; (d) instructions for using the kit to obtain a proteolytic profile for the subject; (e) one or more reference proteolytic profiles characteristic for one or more diseases; and (f) instructions for using the kit assess and/or determine the state of health of the subject.

In various embodiments, the present invention provides a kit for assessing risk of a disease in a subject in need thereof. The kit comprises components to assess the risk of a disease in the subject and instructions for use.

In various embodiments, the kit instructions may include instructions on how to add the internal standard and/or L-natriuretic peptide to a sample. In various embodiments, the kit instructions may include instructions on how relative quantitative signatures of the L-natriuretic peptide cleavage products at a given time point are indicative of endogenous enzymatic activity.

Kit for Identifying a Subject at Risk of Developing a Disease

In various embodiments, the present invention provides a kit for identifying a subject at risk of developing a disease, the kit comprising one or more L-natriuretic peptides; and an internal standard, wherein the internal standard comprises one or more non-natural natriuretic peptides, or one or more non-natural cleavage peptidoforms, or combination thereof. In some embodiments, the kit further comprises instructions for using the kit to identify whether the subject is at risk of developing the disease. In some embodiments, the kit further comprises reagents and instructions for sample processing and preparation. In some embodiments, the non-natural natriuretic peptide is isotopically labeled. In some embodiments, the non-natural natriuretic peptide is not isotopically labeled. In some embodiments, the disease is a cardiovascular disease.

Kit for Diagnosing a Disease

In some embodiments, the present invention provides a kit for diagnosing a disease in a subject, the kit comprising one or more L-natriuretic peptides; and an internal standard, wherein the internal standard comprises one or more non-natural natriuretic peptides, or one or more non-natural cleavage peptidoforms, or combination thereof. In some embodiments, the kit further comprises instructions for using the kit to diagnose the disease in the subject. In some embodiments, the kit further comprises reagents and instructions for sample processing and preparation. In some embodiments, the non-natural natriuretic peptide is isotopically labeled. In some embodiments, the non-natural natriuretic peptide is not isotopically labeled. In some embodiments, the disease is a cardiovascular disease.

Assays

Assay for Monitoring and/or Assessing Efficacy of a Treatment

In various embodiments, the present invention provides an assay for monitoring and/or assessing efficacy of a treatment and/or therapy of a subject, comprising: obtaining a sample comprising one or more proteases from the subject, wherein the subject is being and/or has been treated and/or is/has received therapy for a disease; adding an amount of one or more L-natriuretic peptides to the sample; adding an amount of an internal standard to the sample, wherein the internal standard comprises one or more non-natural natriuretic peptides, one or more non-natural cleavage peptidoforms, or combination thereof; detecting and/or measuring an amount of one or more L-natriuretic peptide cleavage products over a period of time; detecting and/or measuring an amount of the internal standard over a period of time; quantifying the amount of one or more L-natriuretic peptide cleavage products by comparing the amount of one or more L-natriuretic peptide cleavage products with the amount of the internal standard to obtain the proteolytic profile of the subject; and comparing the proteolytic profile from the subject to a proteolytic profile from a reference sample, wherein a change in the proteolytic profile from the subject relative to the proteolytic profile from the reference sample provides for monitoring of the treatment/therapy and/or provides an assessment of the efficacy of the treatment/ therapy. In some embodiments, the detecting and/or measuring of the internal standard comprises detecting and/or measuring the amount of the non-natural natriuretic peptide or the amount of the non-natural cleavage peptidoform. In some embodiments, the quantifying the amount of one or more L-natriuretic peptide cleavage products by comparing the amount of one or more L-natriuretic peptide cleavage products with the amount of the internal standard to obtain the proteolytic profile of the subject, comprises quantifying the amount of one or more L-natriuretic peptide cleavage products by comparing the amount of one or more L-natriuretic peptide cleavage products with the amount of the non-natural natriuretic peptide or the amount of the non-natural cleavage peptidoform.

Assay for Assessing the Risk of Developing a Disease

In various embodiments, the present invention provides an assay for assessing the risk of developing a disease in a subject, comprising: obtaining a sample comprising one or more proteases from the subject; adding an amount of one or more L-natriuretic peptides to the sample; adding an amount of an internal standard to the sample, wherein the internal standard comprises one or more non-natural natriuretic peptides, one or more non-natural cleavage peptidoforms, or combination thereof; detecting and/or measuring an amount of one or more L-natriuretic peptide cleavage products over a period of time; detecting and/or measuring an amount of the internal standard over a period of time; quantifying the amount of one or more L-natriuretic peptide cleavage products by comparing the amount of one or more L-natriuretic peptide cleavage products with the amount of the internal standard, where an increase in the amount of one or more L-natriuretic peptide cleavage products over a period of time is indicative of increased protease activity; determining that the subject has an increased risk of developing a disease if the protease activity is increased over the period of time relative to a reference value; and determining that the subject has a decreased risk of developing a disease if the protease activity is decreased over the period of time relative to the reference value. In some embodiments, the assay further comprises selecting a treatment for the subject if the increased risk of developing a disease is determined. In some embodiments, the assay further comprises detecting and/or measuring an amount of the one or more L-natriuretic peptides over a period of time. In some embodiments, the assay further comprises quantifying the amount of the one or more L-natriuretic peptides over time by comparing the amount of one or more L-natriuretic peptides with the amount of the internal standard, wherein a decrease in the amount of one or more L-natriuretic peptides over a period of time is indicative of increased protease activity. In some embodiments, the disease is a cardiovascular disease. In some embodiments, the assay further comprises treating the subject at risk of developing the disease. In some embodiments, the detecting and/or measuring of the internal standard comprises detecting and/or measuring the amount of the non-natural natriuretic peptide or the amount of the non-natural cleavage peptidoform.

Assay for Obtaining a Proteolytic Profile

In various embodiments, the present invention provides an assay for obtaining a proteolytic profile of one or more cleavage products of one or more L-natriuretic peptides for a subject, the method comprising: obtaining a sample comprising one or more proteases from the subject; adding an amount of one or more L-natriuretic peptides to the sample; adding an amount of an internal standard to the sample, wherein the internal standard comprises one or more non-natural natriuretic peptides, one or more non-natural cleavage peptidoforms, or combination thereof; detecting and/or measuring an amount of one or more L-natriuretic peptides over a period of time; detecting and/or measuring an amount of the internal standard over a period of time; and quantifying the amount of one or more L-natriuretic peptide cleavage products by comparing the amount of one or more L-natriuretic peptide cleavage products with the amount of the internal standard to obtain the proteolytic profile of the subject. In some embodiments, the assay further comprises detecting and/or measuring an amount of the one or more L-natriuretic peptides over a period of time. In some embodiments, the assay further comprises quantifying the amount of the one or more L-natriuretic peptides over time by comparing the amount of one or more L-natriuretic peptides with the amount of the internal standard to obtain the proteolytic profile of the subject. In some embodiments, the detecting and/or measuring of the internal standard comprises detecting and/or measuring the amount of the non-natural natriuretic peptide or the amount of the non-natural cleavage peptidoform. In some embodiments, the quantifying the amount of one or more L-natriuretic peptide cleavage products by comparing the amount of one or more L-natriuretic peptide cleavage products with the amount of the internal standard to obtain the proteolytic profile of the subject, comprises quantifying the amount of one or more L-natriuretic peptide cleavage products by comparing the amount of one or more L-natriuretic peptide cleavage products with the amount of the non-natural natriuretic peptide or the amount of the non-natural cleavage peptidoform.

In some embodiments, the assay further comprises comparing the proteolytic profile from the subject to a proteolytic profile from a reference sample. In some embodiments, the assay further comprises making an assessment of the subject based on the comparison, wherein the assessment is a diagnosis of a disease. In some embodiments, the assay further comprises treating the subject based on the assessment. In some embodiments, the assay further comprises treating the subject for the disease based on the assessment. In some embodiments, the disease is a cardiovascular disease.

In some embodiments, the assay further comprises comparing the proteolytic profile from the subject to a proteolytic profile from a reference sample. In some embodiments, the assay further comprises making an assessment of the subject based on the comparison, wherein the assessment is a prognosis of a disease. In some embodiments, the assay further comprises treating the subject based on the assessment. In some embodiments, the disease is a cardiovascular disease.

In some embodiments, the assay further comprises comparing the proteolytic profile from the subject to a proteolytic profile from a reference sample, wherein a difference between the proteolytic profile of the subject and the proteolytic profile of the reference sample is indicative of a cardiovascular disease.

In some embodiments, the assay further comprises comparing the proteolytic profile from the subject to a proteolytic profile from a reference sample, wherein a difference between the proteolytic profile of the subject and the proteolytic profile of the reference sample is an assessment of the subject, wherein the assessment is a diagnosis of a disease. In some embodiments, the assay further comprises treating the subject based on the assessment. In some embodiments, the assay further comprises treating the subject for the disease based on the assessment. In some embodiments, the disease is a cardiovascular disease.

In some embodiments, the assay further comprises comparing the proteolytic profile from the subject to a proteolytic profile from a reference sample, wherein a difference between the proteolytic profile of the subject and the proteolytic profile of the reference sample is an assessment of the subject, wherein the assessment is a prognosis of developing a disease. In some embodiments, the assay further comprises treating the subject based on the assessment. In some embodiments, the disease is a cardiovascular disease.

In some embodiments, the assay further comprises making an assessment of the subject based on the proteolytic profile, wherein the assessment is a diagnosis of a disease. In some embodiments, the assay further comprises treating the subject based on the assessment. In some embodiments, the assay further comprises making an assessment of the subject based on the proteolytic profile, wherein the assessment is a diagnosis of a disease; and treating the subject based on the assessment. In some embodiments, the disease is a cardiovascular disease.

In some embodiments, the assay further comprises making an assessment of the subject based on the proteolytic profile, wherein the assessment is a prognosis of developing a disease. In some embodiments, the assay further comprises treating the subject based on the assessment. In some embodiments, the assay further comprises making an assessment of the subject based on the proteolytic profile, wherein the assessment is a prognosis of developing a disease; and treating the subject based on the assessment. In some embodiments, the disease is a cardiovascular disease.

In various embodiments, the present invention provides an assay for assessing the efficacy of a treatment, comprising: comparing a proteolytic profile from a subject to a proteolytic profile from a reference sample, wherein a change in the proteolytic profile from the subject relative to the proteolytic profile from the reference sample is indicative of the efficacy of the treatment.

In some embodiments of the present invention, the reference sample is obtained from a control subject, wherein the control subject does not have a disease (e.g., a cardiovascular disease). In some embodiments of the present invention, the reference sample is obtained from the subject before the subject is treated for a disease (e.g., a cardiovascular disease). In some embodiments of the present invention, the reference sample is from a subject that has been treated for a disease (e.g., a cardiovascular disease). In some embodiments of the present invention, the reference sample is obtained from the subject at an earlier time.

Assay for Diagnosing a Disease

In various embodiments, the present invention provides an assay for diagnosing a disease in a subject, comprising obtaining a sample comprising one or more proteases from the subject; adding an amount of one or more L-natriuretic peptides to the sample; adding an amount of an internal standard to the sample, wherein the internal standard comprises one or more non-natural natriuretic peptides, one or more non-natural cleavage peptidoforms, or combination thereof; detecting and/or measuring an amount of one or more L-natriuretic peptide cleavage products of the one or more L-natriuretic peptides over a period of time; detecting and/or measuring an amount of the internal standard over a period of time; and quantifying the amount of one or more L-natriuretic peptide cleavage products by comparing the amount of one or more L-natriuretic peptide cleavage products with the amount of the internal standard to obtain the proteolytic profile of the subject; and comparing the proteolytic profile from the subject to a proteolytic profile from a reference sample, wherein a change in the proteolytic profile from the subject relative to the proteolytic profile from the reference sample is indicative of a disease in the subject. In some embodiments, the detecting and/or measuring of the internal standard comprises detecting and/or measuring the amount of the non-natural natriuretic peptide or the amount of the non-natural cleavage peptidoform. In some embodiments, the quantifying the amount of one or more L-natriuretic peptide cleavage products by comparing the amount of one or more L-natriuretic peptide cleavage products with the amount of the internal standard to obtain the proteolytic profile of the subject, comprises quantifying the amount of one or more L-natriuretic peptide cleavage products by comparing the amount of one or more L-natriuretic peptide cleavage products with the amount of the non-natural natriuretic peptide or the amount of the non-natural cleavage peptidoform.

Assay for Assessing and/or Determining the Risk of Developing a Disease

In various embodiments, the present invention provides an assay for assessing and/or determining the risk of developing a disease in a subject, comprising: obtaining a sample comprising one or more proteases from the subject; adding an amount of one or more L-natriuretic peptides to the sample; adding an amount of an internal standard to the sample, wherein the internal standard comprises one or more non-natural natriuretic peptides, one or more non-natural cleavage peptidoforms, or combination thereof; detecting and/or measuring an amount of one or more L-natriuretic cleavage products of the one or more L-natriuretic peptides over a period of time; detecting and/or measuring an amount of the internal standard over a period of time; and quantifying the amount of one or more L-natriuretic peptide cleavage products by comparing the amount of one or more L-natriuretic peptide cleavage products with the amount of the internal standard to obtain the proteolytic profile of the subject; and comparing the proteolytic profile from the subject to a proteolytic profile from a reference sample, wherein a change in the proteolytic profile from the subject relative to the proteolytic profile from the reference sample is indicative of an increased risk of the subject developing the disease. In some embodiments, the detecting and/or measuring of the internal standard comprises detecting and/or measuring the amount of the non-natural natriuretic peptide or the amount of the non-natural cleavage peptidoform. In some embodiments, the quantifying the amount of one or more L-natriuretic peptide cleavage products by comparing the amount of one or more L-natriuretic peptide cleavage products with the amount of the internal standard to obtain the proteolytic profile of the subject, comprises quantifying the amount of one or more L-natriuretic peptide cleavage products by comparing the amount of one or more L-natriuretic peptide cleavage products with the amount of the non-natural natriuretic peptide or the amount of the non-natural cleavage peptidoform.

Assay for Assessing and/or Determining State of Health

In various embodiments, the present invention provides an assay for assessing and/or determining state of health of a subject, comprising: obtaining a sample comprising one or more proteases from the subject; adding an amount of one or more L-natriuretic peptides to the sample; adding an amount of an internal standard to the sample, wherein the internal standard comprises one or more non-natural natriuretic peptides, one or more non-natural cleavage peptidoforms, or combination thereof; detecting and/or measuring an amount of one or more L-natriuretic peptide cleavage products of the one or more L-natriuretic peptides over a period of time; detecting and/or measuring an amount of the internal standard over a period of time; and quantifying the amount of one or more L-natriuretic peptide cleavage products by comparing the amount of one or more L-natriuretic peptide cleavage products with the amount of the internal standard to obtain the proteolytic profile of the subject; comparing the proteolytic profile from the subject to a proteolytic profile from one or more reference samples; and assessing the state of health of the subject based on the comparison. In some embodiments, the detecting and/or detecting and/or measuring of the internal standard comprises detecting and/or measuring the amount of the non-natural natriuretic peptide or the amount of the non-natural cleavage peptidoform. In some embodiments, the quantifying the amount of one or more L-natriuretic peptide cleavage products by comparing the amount of one or more L-natriuretic peptide cleavage products with the amount of the internal standard to obtain the proteolytic profile of the subject, comprises quantifying the amount of one or more L-natriuretic peptide cleavage products by comparing the amount of one or more L-natriuretic peptide cleavage products with the amount of the non-natural natriuretic peptide or the amount of the non-natural cleavage peptidoform.

Assay for Identifying and/or Assessing a Condition

In various embodiments, the present invention provides an assay for identifying and/or assessing a condition of a subject, comprising: obtaining a sample comprising one or more proteases from the subject; adding an amount of one or more L-natriuretic peptides to the sample; adding an amount of an internal standard to the sample, wherein the internal standard comprises one or more non-natural natriuretic peptides, one or more non-natural cleavage peptidoforms, or combination thereof; detecting and/or measuring an amount of one or more L-natriuretic peptide cleavage products of the one or more L-natriuretic peptides over a period of time; detecting and/or measuring an amount of the internal standard over a period of time; and quantifying the amount of one or more L-natriuretic peptide cleavage products by comparing the amount of one or more L-natriuretic peptide cleavage products with the amount of the internal standard to obtain the proteolytic profile of the subject; comparing the proteolytic profile from the subject to a proteolytic profile from one or more reference samples; and identifying and/or assessing the condition of the subject based on the comparison. In some embodiments, the detecting and/or measuring of the internal standard comprises detecting and/or measuring the amount of the non-natural natriuretic peptide or the amount of the non-natural cleavage peptidoform. In some embodiments, the quantifying the amount of one or more L-natriuretic peptide cleavage products by comparing the amount of one or more L-natriuretic peptide cleavage products with the amount of the internal standard to obtain the proteolytic profile of the subject, comprises quantifying the amount of one or more L-natriuretic peptide cleavage products by comparing the amount of one or more L-natriuretic peptide cleavage products with the amount of the non-natural natriuretic peptide or the amount of the non-natural cleavage peptidoform.

Assay for Diagnosing and/or Prognosing State of Health

In various embodiments, the present invention provides an assay for diagnosing and/or prognosing state of health of a subject, comprising: obtaining a sample comprising one or more proteases from the subject; adding an amount of one or more L-natriuretic peptides to the sample; adding an amount of an internal standard to the sample, wherein the internal standard comprises one or more non-natural natriuretic peptides, one or more non-natural cleavage peptidoforms, or combination thereof; detecting and/or measuring an amount of one or more L-natriuretic peptide cleavage products of the one or more L-natriuretic peptides over a period of time; detecting and/or measuring an amount of the internal standard over a period of time; and quantifying the amount of one or more L-natriuretic peptide cleavage products by comparing the amount of one or more L-natriuretic peptide cleavage products with the amount of the internal standard to obtain the proteolytic profile of the subject; comparing the proteolytic profile from the subject to a proteolytic profile from one or more reference samples; and diagnosing and/or prognosing the state of health of the subject based on the comparison. In some embodiments, the detecting and/or measuring of the internal standard comprises detecting and/or measuring the amount of the non-natural natriuretic peptide or the amount of the non-natural cleavage peptidoform. In some embodiments, the quantifying the amount of one or more L-natriuretic peptide cleavage products by comparing the amount of one or more L-natriuretic peptide cleavage products with the amount of the internal standard to obtain the proteolytic profile of the subject, comprises quantifying the amount of one or more L-natriuretic peptide cleavage products by comparing the amount of one or more L-natriuretic peptide cleavage products with the amount of the non-natural natriuretic peptide or the amount of the non-natural cleavage peptidoform.

Assay for Diagnosing and/or Prognosing a Condition

In various embodiments, the present invention provides a method of diagnosing and/or prognosing a condition in subject, comprising: obtaining a sample comprising one or more proteases from the subject; adding an amount of one or more L-natriuretic peptides to the sample; adding an amount of an internal standard to the sample, wherein the internal standard comprises one or more non-natural natriuretic peptides, one or more non-natural cleavage peptidoforms, or combination thereof; detecting and/or measuring an amount of one or more L-natriuretic peptide cleavage products of the one or more L-natriuretic peptides over a period of time; detecting and/or measuring an amount of the internal standard over a period of time; and quantifying the amount of one or more L-natriuretic peptide cleavage products by comparing the amount of one or more L-natriuretic peptide cleavage products with the amount of the internal standard to obtain the proteolytic profile of the subject; comparing the proteolytic profile from the subject to a proteolytic profile from one or more reference sample; and diagnosing and/or prognosing the condition of the subject based on the comparison. In some embodiments, the detecting and/or measuring of the internal standard comprises detecting and/or measuring the amount of the non-natural natriuretic peptide or the amount of the non-natural cleavage peptidoform. In some embodiments, the quantifying the amount of one or more L-natriuretic peptide cleavage products by comparing the amount of one or more L-natriuretic peptide cleavage products with the amount of the internal standard to obtain the proteolytic profile of the subject, comprises quantifying the amount of one or more L-natriuretic peptide cleavage products by comparing the amount of one or more L-natriuretic peptide cleavage products with the amount of the non-natural natriuretic peptide or the amount of the non-natural cleavage peptidoform.

Assay for Determining the Amount of L-Natriuretic Peptides and/or L-Natriuretic Peptide Cleavage Products In various embodiments, the present invention provides an assay for determining the amount of one or more L-natriuretic peptides and/or one or more L-natriuretic peptide cleavage products of one or more L-natriuretic peptides in a sample from a subject, the assay comprising: obtaining a sample comprising one or more proteases from the subject; adding an amount of an internal standard to the sample, wherein the internal standard comprises one or more non-natural natriuretic peptides, one or more non-natural cleavage peptidoforms, or combination thereof; detecting and/or measuring an amount of one or more L-natriuretic peptides and/or one or more L-natriuretic peptide cleavage products over a period of time; detecting and/or measuring an amount of the internal standard over a period of time; and quantifying the amount of one or more L-natriuretic peptides and/or one or more L-natriuretic peptide cleavage products by comparing the amount of one or more L-natriuretic peptides and/or one or more L-natriuretic peptide cleavage products with the amount of the internal standard to determine the amount of one or more L-natriuretic peptides and/or one or more L-natriuretic peptide cleavage products. In some embodiments, the detecting and/or measuring of the internal standard comprises detecting and/or measuring the amount of the non-natural natriuretic peptide or the amount of the non-natural cleavage peptidoform.

Some embodiments of the present invention can be defined as any of the following numbered paragraphs:

1. A method, for determining the risk of developing cardiovascular disease in a subject, comprising:
   obtaining a biological sample comprising one or more proteases from the subject;
   adding a quantity of one or more natriuretic peptides to the biological sample; and
   detecting the presence of one or more cleavage products of the one or more natriuretic peptides over a period of time, wherein the presence of one or more cleavage products is indicative of an increased risk of the subject developing cardiovascular disease.

2. The method of paragraph 1, further comprising selecting one or more treatments for the subject if the increased risk of developing cardiovascular disease is determined.

3. The method of paragraph 1, wherein the natriuretic peptides are any one or more of Brain natriuretic peptide (BNP), Atrial natriuretic peptide (ANP), C-type natriuretic peptide (CNP) or combinations thereof.

4. The method of paragraph 1, wherein the proteases are any one or more of neutral endopeptidase, dipeptidylpeptidase IV, insulin degrading enzyme or combination thereof.

5. The method of paragraph 1, wherein the sample is plasma, blood, or serum.

6. The method of paragraph 1, wherein the period of time is up to 1 hour.

7. The method of paragraph 1, wherein the period of time is up to 14 hours.

8. The method of paragraph 1, wherein the cleavage products are any one or more of BNP 3-30, BNP 3-29, BNP 3-32, BNP 1-30 or combinations thereof.

9. The method of paragraph 1, wherein the cleavage products are any one or more of BNP 3-30, BNP 3-29, BNP 3-32, BNP 1-30, BNP 5-29, BNP 4-29, BNP 1-28, BNP 1-29, BNP 4-31, BNP 4-32 or combinations thereof.

10. The method of paragraph 1, wherein the cleavage products are any one or more of BNP 3-30, BNP 3-29, BNP 3-32, BNP 1-30, BNP 1-29, BNP 1-28, BNP 2-31, BNP 3-30, BNP 4-30, BNP 4-29, BNP 4-27, BNP 5-32, BNP 5-31, BNP 5-29, BNP 4-32, BNP 4-31, or combinations thereof.

11. The method of paragraph 1, wherein the cleavage products are any one or more of 30-32, 25-30, 20-25, 25-32, 15-20, 10-15, 5-10, 10-20 or 20-30 consecutive amino acids of the natriuretic peptides.

12. The method of any one of paragraphs 8, 9, 10, or 11 wherein the cleavage products are not modified.

13. The method of any one of paragraphs 8, 9, 10, or 11, wherein the cleavage products are modified.

14. The method of paragraph 13, wherein the modification is oxidation at the methionine residue.

15. The method of paragraph 1, wherein the cleavage products are detected using any one or more of capillary electrophoresis/electrospray ionization-mass spectrometry (CESI-MS), capillary electrophoresis-mass spectrometry (CE-MS), liquid chromatography mass spectrometry (LC-MS), high pressure liquid chromatography mass spectrometry (HPLC-MS), or combinations thereof.

16. The method of paragraph 1, wherein the quantity of one or more natriuretic peptides added to the sample is about any one or more of 10 ng/µL, 50 ng/µL, 75 ng/µL, 100 ng/µL, 125 ng/µL, 150 ng/µL, 175 ng/µL, 200 ng/µL, 225 ng/µL, 250 ng/µL, 275 ng/µL, 300 ng/µL, 350 ng/µL, 375 ng/µL, 400 ng/µL, 450 ng/µL, 475 ng/µL, 500 ng/µL or combinations thereof.

17. The method of paragraph 1, wherein the cardiovascular disease is heart failure, arterial fibrillation or combination thereof.

18. The method of paragraph 1, further comprising: comparing the presence of one or more cleavage products of the one or more natriuretic peptides from the subject to the presence of one or more cleavage products of the one or more natriuretic peptides from a reference sample.

19. The method of paragraph 18, further comprising: making an assessment of the subject based on the comparison, wherein the assessment is a determination of the risk of developing cardiovascular disease.

20. The method of paragraph 18, wherein the reference sample is obtained from a healthy subject.

21. The method of paragraph 18, wherein the reference sample is obtained from a subject that has been treated for the cardiovascular disease.

22. The method of paragraph 18, wherein the reference sample is obtained from the subject at an earlier point in time.

23. The method of paragraph 18, wherein the reference sample is obtained from the subject before the subject is treated for the cardiovascular disease.

24. The method of paragraph 1, further comprising detecting the presence of one or more natriuretic peptides over a period of time.

Some embodiments of the present invention can be defined as any of the following numbered paragraphs:

25. A non-natural natriuretic peptide comprising one or more D-amino acids.

26. The non-natural natriuretic peptide of paragraph 25, wherein the non-natural natriuretic peptide is any one or more of non-natural brain natriuretic peptides (non-natural B-type natriuretic peptides), non-natural atrial natriuretic peptides (non-natural A-type natriuretic peptides), non-natural C-type natriuretic peptides, or combinations thereof.

27. The non-natural natriuretic peptide of paragraph 25, wherein at least one of the D-amino acids are isotopically labeled.

28. The non-natural natriuretic peptide of paragraph 25, wherein the D-amino acids are not isotopically labeled.

29. The non-natural natriuretic peptide of paragraph 25, wherein the one or more D-amino acids are selected from the group consisting of D-enantiomers of Ala, Ile, Leu, Met, Val, Phe, Trp, Tyr, Asn, Cys, Gln, Ser, Thr, Asp, Glu, Arg, His, Lys, and Pro.

30. The non-natural natriuretic peptide of paragraph 25, further comprising one or more L-amino acids.

31. The non-natural natriuretic peptide of paragraph 30, wherein at least one of the L-amino acids are isotopically labeled.

32. The non-natural natriuretic peptide of paragraph 30, wherein the L-amino acids are not isotopically labeled.

33. The non-natural natriuretic peptide of paragraph 30, wherein the one or more L-amino acids are selected from the group consisting of L-enantiomers of Ala, Ile, Leu, Met, Val, Phe, Trp, Tyr, Asn, Cys, Gln, Ser, Thr, Asp, Glu, Arg, His, Lys, and Pro.

34. A kit, comprising:
    (a) an internal standard, wherein the internal standard comprises one or more non-natural natriuretic peptides, or one or more non-natural cleavage peptidoforms, or combination thereof;
    (b) one or more L-natriuretic peptides; and
    (c) instructions for using the kit.

35. A kit for obtaining a proteolytic profile from a sample comprising:
    (a) an internal standard, wherein the internal standard comprises one or more non-natural natriuretic peptides, wherein the non-natural natriuretic peptides comprise one or more D-amino acids;
    (b) one or more L-natriuretic peptides; and
    (c) instructions for using the kit to obtain the proteolytic profile for the sample.

36. A kit for identifying and/or assessing a condition of a subject, the kit comprising:
    (a) an internal standard, wherein the internal standard comprises one or more non-natural natriuretic peptides, wherein the non-natural natriuretic peptides comprise one or more D-amino acids;
    (b) one or more L-natriuretic peptides;
    (c) reagents and instructions for sample processing and preparation;
    (d) instructions for using the kit to obtain a proteolytic profile for the subject;
    (e) one or more reference proteolytic profiles characteristic for one or more diseases; and
    (f) instructions for using the kit to identify and/or assess the condition of the subject.

37. The kit of paragraph 36, wherein the condition is a disease.

38. The kit of paragraph 37, wherein the disease is a cardiovascular disease.

39. The kit of any one of paragraphs 34, 35 or 36, wherein the non-natural natriuretic peptide is non-natural brain natriuretic peptide, non-natural atrial natriuretic peptide, or non-natural C-type natriuretic peptide, or combinations thereof.

40. The kit of any one of paragraphs 34, 35 or 36, wherein the L-natriuretic peptide is a natural natriuretic peptide, or a cleavable synthetic natriuretic peptide, or combination thereof.

41. The kit of paragraph 40, wherein the natural natriuretic peptide is natural brain natriuretic peptide, natural atrial natriuretic peptide, or natural C-type natriuretic peptide, or combinations thereof.

42. The kit of paragraph 40, wherein the cleavable synthetic natriuretic peptide is cleavable synthetic brain natriuretic peptide, cleavable synthetic atrial natriuretic peptide, or cleavable synthetic C-type natriuretic peptide, or combinations thereof.

43. The kit of paragraph 34, wherein the non-natural natriuretic peptide comprises one or more D-amino acids.

44. The kit of any one of paragraphs 35, 36 or 43, wherein at least one of the D-amino acids are isotopically labeled.

45. The kit of any one of paragraphs 35, 36 or 43, wherein the D-amino acids are not isotopically labeled.

46. The kit of any one of paragraphs 35, 36 or 43, wherein the D-amino acids are selected from the group consisting of D-enantiomers of Ala, Ile, Leu, Met, Val, Phe, Trp, Tyr, Asn, Cys, Gln, Ser, Thr, Asp, Glu, Arg, His, Lys, and Pro.

47. The kit of any one of paragraphs 34, 35 or 36, wherein an amount of non-natural natriuretic peptide and an amount of L-natriuretic peptide are the same.

48. The kit of any one of paragraphs 35, 36 or 43, wherein the non-natural natriuretic peptide further comprises one or more L-amino acids.

49. The kit of paragraph 48, wherein at least one of the L-amino acids are isotopically labeled.

50. The kit of paragraph 48, wherein the L-amino acids are not isotopically labeled.

51. The kit of paragraph 48, wherein the one or more L-amino acids are selected from the group consisting of L-enantiomers of Ala, Ile, Leu, Met, Val, Phe, Trp, Tyr, Asn, Cys, Gln, Ser, Thr, Asp, Glu, Arg, His, Lys, and Pro.

52. A pharmaceutical composition, comprising: one or more non-natural natriuretic peptides of paragraph 25; and a pharmaceutically acceptable carrier.

53. A method of obtaining a proteolytic profile of one or more cleavage products of one or more L-natriuretic peptides for a subject, the method comprising:
obtaining a sample comprising one or more proteases from the subject;
adding an amount of one or more L-natriuretic peptides to the sample;
adding an amount of an internal standard to the sample, wherein the internal standard comprises one or more non-natural natriuretic peptides, one or more non-natural cleavage peptidoforms, or combination thereof;
detecting and/or measuring an amount of one or more L-natriuretic peptides over a period of time;
detecting and/or measuring an amount of the internal standard over a period of time; and
quantifying the amount of one or more L-natriuretic peptide cleavage products by comparing the amount of one or more L-natriuretic peptide cleavage products with the amount of the internal standard to obtain the proteolytic profile of the subject.

54. The method of paragraph 53, further comprising comparing the proteolytic profile from the subject to a proteolytic profile from a reference sample, and making an assessment of the subject based on the comparison, wherein the assessment is a diagnosis of a disease.

55. The method of paragraph 54, further comprising treating the subject, selecting a treatment for the subject, and/or providing a treatment for the subject based on the assessment.

56. The method of paragraph 54, wherein the disease is a cardiovascular disease.

57. A method for diagnosing a disease in a subject, comprising:
obtaining a sample comprising one or more proteases from the subject;
adding an amount of one or more L-natriuretic peptides to the sample;
adding an amount of an internal standard to the sample, wherein the internal standard comprises one or more non-natural natriuretic peptides, one or more non-natural cleavage peptidoforms, or combination thereof;
detecting and/or measuring an amount of one or more L-natriuretic peptide cleavage products of the one or more L-natriuretic peptides over a period of time;
detecting and/or measuring an amount of the internal standard over a period of time;
quantifying the amount of one or more L-natriuretic peptide cleavage product by comparing the amount of one or more L-natriuretic peptide cleavage products with the amount of the internal standard to obtain the proteolytic profile of the subject; and
comparing the proteolytic profile from the subject to a proteolytic profile from a reference sample, wherein a change in the proteolytic profile from the subject relative to the proteolytic profile from the reference sample is indicative of a disease in the subject.

58. The method of paragraph 57, further comprising treating the subject and/or selecting at treatment for the subject and/or providing a treatment for the subject.

59. A method for assessing and/or determining the risk of developing a disease in a subject, comprising:
obtaining a sample comprising one or more proteases from the subject;
adding an amount of one or more L-natriuretic peptides to the sample;
adding an amount of an internal standard to the sample, wherein the internal standard comprises one or more non-natural natriuretic peptides, one or more non-natural cleavage peptidoforms, or combination thereof;
detecting and/or measuring an amount of one or more L-natriuretic peptide cleavage products of the one or more L-natriuretic peptides over a period of time;
detecting and/or measuring an amount of the internal standard over a period of time;
quantifying the amount of one or more L-natriuretic peptide cleavage product by comparing the amount of one or more L-natriuretic peptide cleavage products with the amount of the internal standard to obtain the proteolytic profile of the subject; and
comparing the proteolytic profile from the subject to a proteolytic profile from a reference sample, wherein a change in the proteolytic profile from the subject relative to the proteolytic profile from the reference sample is indicative of an increased risk of the subject developing the disease.

60. A method of diagnosing and/or prognosing a condition in a subject, comprising:
obtaining a sample comprising one or more proteases from the subject;
adding an amount of one or more L-natriuretic peptides to the sample;
adding an amount of an internal standard to the sample, wherein the internal standard comprises one or more non-natural natriuretic peptides, one or more non-natural cleavage peptidoforms, or combination thereof;
detecting and/or measuring an amount of one or more L-natriuretic peptide cleavage products of the one or more L-natriuretic peptides over a period of time;
detecting and/or measuring an amount of the internal standard over a period of time;
quantifying the amount of one or more L-natriuretic peptide cleavage products by comparing the amount of one or more L-natriuretic peptide cleavage products with the amount of the internal standard to obtain the proteolytic profile of the subject;
comparing the proteolytic profile from the subject to a proteolytic profile from one or more reference samples; and
diagnosing and/or prognosing the condition of the subject based on the comparison.

61. The method of paragraph 60, wherein the reference sample is from a diseased subject having one or more diseases.

62. The method of paragraph 60, wherein the reference sample is from a healthy subject.

63. The method of paragraph 60, further comprising treating the subject and/or selecting a treatment and/or providing a treatment and/or selecting a preventative treatment and/or providing a preventative treatment for the subject based on the diagnosis and/or prognosis.

64. The method of paragraph 60, wherein the condition is a disease.

65. The method of paragraph 64, wherein the disease is a cardiovascular disease.

66. The method of any one of paragraphs 54, 57, 59 or 60, wherein the reference sample is obtained from a control subject, wherein the control subject does not have the disease.

67. The method of any one of paragraphs 54, 57, 59 or 60, wherein the reference sample is obtained from the subject before the subject is treated for the disease.

68. The method of any one of paragraphs 54, 57, 59 or 60, wherein the reference sample is from a subject that has been successfully treated for the disease.

69. The method of any one or paragraphs 53, 57, 59 or 60, wherein the non-natural natriuretic peptide is non-natural brain natriuretic peptide, non-natural atrial natriuretic peptide, or non-natural C-type natriuretic peptide, or combinations thereof.

70. The method of any one or paragraphs 53, 57, 59 or 60, wherein the L-natriuretic peptide is a natural natriuretic peptide, or a cleavable synthetic natriuretic peptide, or combination thereof.

71. The method of paragraph 70, wherein the natural natriuretic peptide is natural brain natriuretic peptide, natural atrial natriuretic peptide, or natural C-type natriuretic peptide, or combinations thereof.

72. The method of paragraph 70, wherein the cleavable synthetic natriuretic peptide is cleavable synthetic brain natriuretic peptide, cleavable synthetic atrial natriuretic peptide, or cleavable synthetic C-type natriuretic peptide, or combinations thereof.

73. The method of any one or paragraphs 53, 57, 59 or 60, wherein the non-natural natriuretic peptide comprises one or more D-amino acids.

74. The method of any one or paragraphs 53, 57, 59 or 60, wherein the non-natural natriuretic peptide is isotopically labeled.

75. The method of any one or paragraphs 53, 57, 59 or 60, wherein the non-natural natriuretic peptide is not isotopically labeled.

76. The method of paragraph 73, wherein at least one of the D-amino acids are isotopically labeled.

77. The method of paragraph 73, wherein the D-amino acids are not isotopically labeled.

78. The method of paragraph 73, wherein the D-amino acids are selected from the group consisting of D-enantiomers of Ala, Ile, Leu, Met, Val, Phe, Trp, Tyr, Asn, Cys, Gln, Ser, Thr, Asp, Glu, Arg, His, Lys, and Pro.

79. The method of any one or paragraphs 53, 57, 59 or 60, wherein an amount of non-natural natriuretic peptide and an amount of L-natriuretic peptide are the same.

80. The method of any one or paragraphs 53, 57, 59 or 60, wherein the non-natural natriuretic peptide further comprises one or more L-amino acids.

81. The method of paragraph 80, wherein at least one of the L-amino acids are isotopically labeled.

82. The method of paragraph 80, wherein the one or more L-amino acids are selected from the group consisting of L-enantiomers of Ala, Ile, Leu, Met, Val, Phe, Trp, Tyr, Asn, Cys, Gln, Ser, Thr, Asp, Glu, Arg, His, Lys, and Pro.

83. The method of any one of paragraphs 53, 57, 59 or 60, further comprising detecting and/or measuring the amount of one or more L-natriuretic peptides over a period of time; and quantifying the amount of one or more L-natriuretic peptides by comparing the amount of one or more L-natriuretic peptides with the amount of the internal standard.

84. A non-natural natriuretic peptide comprising a plurality of amino acids, wherein the amino acids are selected from chiral amino acids and non-chiral amino acids, wherein each chiral amino acid is a D-amino acid.

85. The non-natural natriuretic peptide of claim 84, wherein the non-natural natriuretic peptide is any one or more of non-natural brain natriuretic peptides, non-natural atrial natriuretic peptides, non-natural C-type natriuretic peptides, or combinations thereof.

86. The non-natural natriuretic peptide of paragraph 84, wherein at least one of the D-amino acids are isotopically labeled.

87. The non-natural natriuretic peptide of paragraph 84, wherein the D-amino acids are not isotopically labeled.

88. The non-natural natriuretic peptide of paragraph 84, wherein the D-amino acids are selected from the group consisting of D-enantiomers of Ala, Ile, Leu, Met, Val, Phe, Trp, Tyr, Asn, Cys, Gln, Ser, Thr, Asp, Glu, Arg, His, Lys, and Pro.

89. The non-natural natriuretic peptide of paragraph 84, wherein the non-chiral amino acid is Gly.

90. The method of any one of paragraphs 53, 57, 59, 60 or 83, wherein the L-natriuretic peptides and/or the L-natriuretic peptide cleavage products are measured and/or quantified and/or detected using any one or more of capillary electrophoresis (CE), mass spectrometry (MS), capillary electrophoresis/electrospray ionization-mass spectrometry (CESI-MS), capillary electrophoresis-mass spectrometry (CE-MS), liquid chromatography mass spectrometry (LC-MS), high pressure liquid chromatography mass spectrometry (HPLC-MS), or combinations thereof.

91. The method of any one of paragraphs 53, 57, 59, 60 or 83, wherein the non-natural natriuretic peptides and/or the non-natural cleavage peptidoforms are measured and/or quantified and/or detected using any one or more of capillary electrophoresis (CE), mass spectrometry (MS), capillary electrophoresis/electrospray ionization-mass spectrometry (CESI-MS), capillary electrophoresis-mass spectrometry (CE-MS), liquid chromatography mass spectrometry (LC-MS), high pressure liquid chromatography mass spectrometry (HPLC-MS), or combinations thereof.

92. The method of any one of paragraphs 53, 57, 59 or 60, wherein the proteases are any one or more of neutral endopeptidase (NEP), dipeptidylpeptidase IV (DPPIV), and insulin degrading enzyme (IDE), or combination thereof.

93. The non-natural natriuretic peptide of paragraph 25, further comprising one or more Gly amino acids.

94. The kit of any one of paragraphs 35, 36, or 43, wherein the non-natural natriuretic peptide further comprises one or more Gly amino acids.

Various embodiments of the present invention are described in the ensuing examples. The examples are intended to be illustrative and in no way restrictive.

EXAMPLES

The invention is further illustrated by the following examples which are intended to be purely exemplary of the invention, and which should not be construed as limiting the invention in any way. The following examples are illustrative only, and are not intended to limit, in any manner, any of the aspects described herein. The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

The following examples are not intended to limit the scope of the claims to the invention, but are rather intended to be exemplary of certain embodiments. Any variations in the exemplified methods which occur to the skilled artisan are intended to fall within the scope of the present invention.

EXPERIMENTAL METHODS

Recombinant human $BNP_{1-32}$ was purchased from Sigma-Aldrich Cat #B5900, and dissolved in Optima grade water (Fisher Scientific W6500) at 2.5 mg/mL. These $BNP_{1-32}$ standards were stored at −80° C. in 10λ aliquots prior to use. Artificial plasma consisted of 2.25 g bovine serum albumin (Recho Ref #: 03117332001) dissolved in 50 mL 1×PBS pH 7.4 (Quality Biological Cat #:119-069-131, Lot #: 720744) with 1 tablet of protease inhibitors (Thermo Scientific Cat #:88266). Human plasma was purchased from Bioreclamation, including human heparin plasma (Cat #: HMPLNAHP, Lot #: BRH181304) and human EDTA plasma (Cat #: HMPLEDTA, Lot #: BRH1120184).

Plasma Sample Preparation.

All plasma samples were centrifuged through a 0.22 μm spin filter (E&K scientific, Cat #: EK-680850) for 15 min at 16100 g. Filtered plasma was stored at −80° C. in 10λ aliquots. Plasma aliquots were thawed on ice immediately prior to a CE-MS experiment, and mixed with a designated $BNP_{1-32}$ solutions to achieve a final $BNP_{1-32}$ concentration of 250 ng/μL (unless the concentration is otherwise stated).

Capillary Electrophoresis and Mass Spectrometry.

CE System: CE experiments were carried out using a CESI 8000 High Performance Separation-ESI Module (Sciex Separations, Brea, Calif.). The capillary and sample storage temperatures were maintained at 25° C. The capillary used in this study was the OptiMS Neutral Surface Cartridge (Sciex Separations, Brea, Calif.). Prior to use, the capillary was first washed by 0.1M hydrochloric acid (Sigma-Aldrich, Cat #258148), then rinsed with background electrolyte (BGE) consisting of 10% acetic acid (Fisher Scientific, Cat #: A38-500), and finally rinsed with deionized water for 30 min at 100 psi and stored overnight filled with water. Before each run, the capillary was rinsed with 0.1M HCl and flushed with fresh BGE for 10 min at 100 psi. Unless otherwise stated, samples were injected by 10 kV voltage for 5 sec and the BGE spacer was added between samples by hydrodynamic injection. A separation voltage of 30 kV was applied across the capillary with a supplemental forward pressure of 1.5 psi.

Mass Spectrometry.

CESI-MS experiments were performed using a Q Exactive+ mass spectrometer (Thermo Fisher Scientific, San Jose, USA). The electrospray voltage used was 1.8 kV. Data were acquired with automatic gain control of $3\times10^6$ and a maximum injection time of 100 msec. The scan range was set to 200-1200m/z. The MS resolution was set to 70K for the full $MS^1$ scans, respectively, and the default charge was 4.

Data Analysis.

We performed peptide mapping analysis for the identification and confirmation of BNP peptidoforms using Biopharmfinder 1.0 SP1 software (Thermofisher Scientific, San Jose, USA). Accurate $MS^1$ quantitation of identified peptidoforms was accomplished using Tracefinder 3.1 (Thermofisher Scientific, San Jose, USA).

This study provides a mass spectrometry-based method capable of reproducibly analyzing $BNP_{1-32}$ proteolysis profile in a plasma matrix with an overarching longer term vision of providing a deeper understanding of heart failure. In keeping with this goal, we identified the following constraints that our method would have to overcome. First, because a bottom-up proteomics approach (Zhang, Y.; Fonslow, B. R.; Shan, B.; Baek, M. C.; Yates, J. R., 3rd, Protein analysis by shotgun/bottom-up proteomics. *Chem Rev* 2013, 113 (4), 2343-94) could directly impact the diversity of the cleavage peptidoforms we seek to detect, our method necessarily must be top-down analysis (Cai, W.; Tucholski, T. M.; Gregorich, Z. R.; Ge, Y., Top-down Proteomics: Technology Advancements and Applications to Heart Diseases. *Expert Rev Proteomics* 2016, 13 (8), 717-30) of intact proteins. Second, the concentration of endogenous BNP peptidoforms in plasma is estimated in the sub-pg/μL range (Maisel, A., B-type natriuretic peptide levels: diagnostic and prognostic in congestive heart failure: what's next? *Circulation* 2002, 105 (20), 2328-31). In our initial screening experiments, this concentration was within the reach of nano flow LC-MS for the analysis of standard $BNP_{1-32}$ reconstituted in a clean aqueous matrix. Unfortunately, achieving this level of sensitivity with sufficient accuracy and reproducibility in plasma samples requires enrichment strategies as well as sample cleanup, and/or fractionation. Finally, while catabolic processes in plasma remain active, sources for secretion of newly synthesized $BNP_{1-32}$ are absent in sampled blood. Therefore, analytical accuracy and reproducibility for endogenous BNP peptidoforms may be secondary to the disruption inherent to sample extraction.

Our approach aims to simultaneously circumvent these constraints by applying a pulse of exogenous standard $BNP_{1-32}$, followed by direct sampling and analysis of BNP peptidoforms resulting from those intact catabolic processes in a plasma sample. We based our method on a CESI-MS platform for several key reasons: First, BNP is a small protein with a pI of 11, thus carrying a charge across a wide pH range (Table 1). This basic characteristic inherent to BNP and its fragment peptidoforms endows it with an electrophoretic mobility that exceeds a majority of other plasma proteins, which helps minimize interfering signals and plasma matrix effect. Second, the low sample consumption of a given CE run provides an opportunity for multiple successive sampling at different time points from a single vial. Third, CE methods can be built to include MSI, where multiple sample injections separated by short background electrolyte spacers can be simultaneously run and analyzed. The increase in throughput afforded by MSI is an especially attractive feature where the analysis of multiple time points, potential enzyme kinetics, and/or larger clinical cohorts are concerned.

Our experimental strategy involved the following approach: 1. Establish CESI-MS conditions for the analysis of standard $BNP_{1-32}$. 2. Transfer these conditions to the analysis of standard $BNP_{1-32}$ pulsed into plasma. 3. Optimize the method for the simultaneous detection of cleavage peptidoforms in plasma. 4. Explore the application of CESI-MS in one-hour BNP proteolytic profile.

CESI-MS for Standard BNP Analysis.

Eleven putative BNP cleavage peptidoforms have previously been described in the literature (Niederkofler, E. E.; Kiernan, U. A.; O'Rear, J.; Menon, S.; Saghir, S.; Protter, A. A.; Nelson, R. W.; Schellenberger, U., Detection of endogenous B-type natriuretic peptide at very low concentrations in patients with heart failure. *Circ Heart Fail* 2008, 1 (4), 258-64). These are derived from at least three known BNP-specific proteolytic enzymes; Neutral endopeptidase (NEP), dipeptidylpeptidase IV (DPPIV), and insulin degrading enzyme (IDE) (Volpe, M.; Rubattu, S.; Burnett, J., Jr., Natriuretic peptides in cardiovascular diseases: current use and perspectives. *Eur Heart J* 2014, 35 (7), 419-25). Table 1 summarizes the theoretical isoelectric points of these peptidoforms in contrast with those of the BNP proteolytic enzymes. Given that our goal was direct sampling from plasma, where the pH falls between the theoretical pI of our panel of potential target analytes and that of the proteolytic enzymes, we built our CE method with electrokinetic sample injection. The use of electrokinetic injection in a neutral pH sample endows our method with the ability to selectively introduce high pI analytes which include all potential BNP peptidoforms, while excluding the lower pI catabolic enzymes responsible for their generation. This technique also simultaneously serves as an endogenous cleanup step that decreases dynamic range and sample plug complexity.

TABLE 1

Theoretical pI values for BNP peptidoforms and known plasma proteolytic enzymes wuth uniprot accession number.

| BNP peptidoform | Theoretical pI |
| --- | --- |
| $BNP_{1-32}$ | 12.14 |
| $BNP_{3-32}$ | 12.14 |
| $BNP_{3-29}$ | 11.49 |
| $BNP_{3-30}$ | 11.90 |
| $BNP_{1-30}$ | 11.90 |
| $BNP_{5-29}$ | 9.50 |
| $BNP_{4-29}$ | 9.50 |
| $BNP_{1-28}$ | 9.85 |
| $BNP_{1-29}$ | 9.85 |
| $BNP_{4-31}$ | 10.86 |
| $BNP_{4-32}$ | 10.86 |
| Neutral endopeptidase (P08473) | 5.54 |
| Dipeptidylpeptidase IV (P27487) | 5.67 |
| Insulin degrading enzyme (P14735) | 6.16 |

Figure 14:
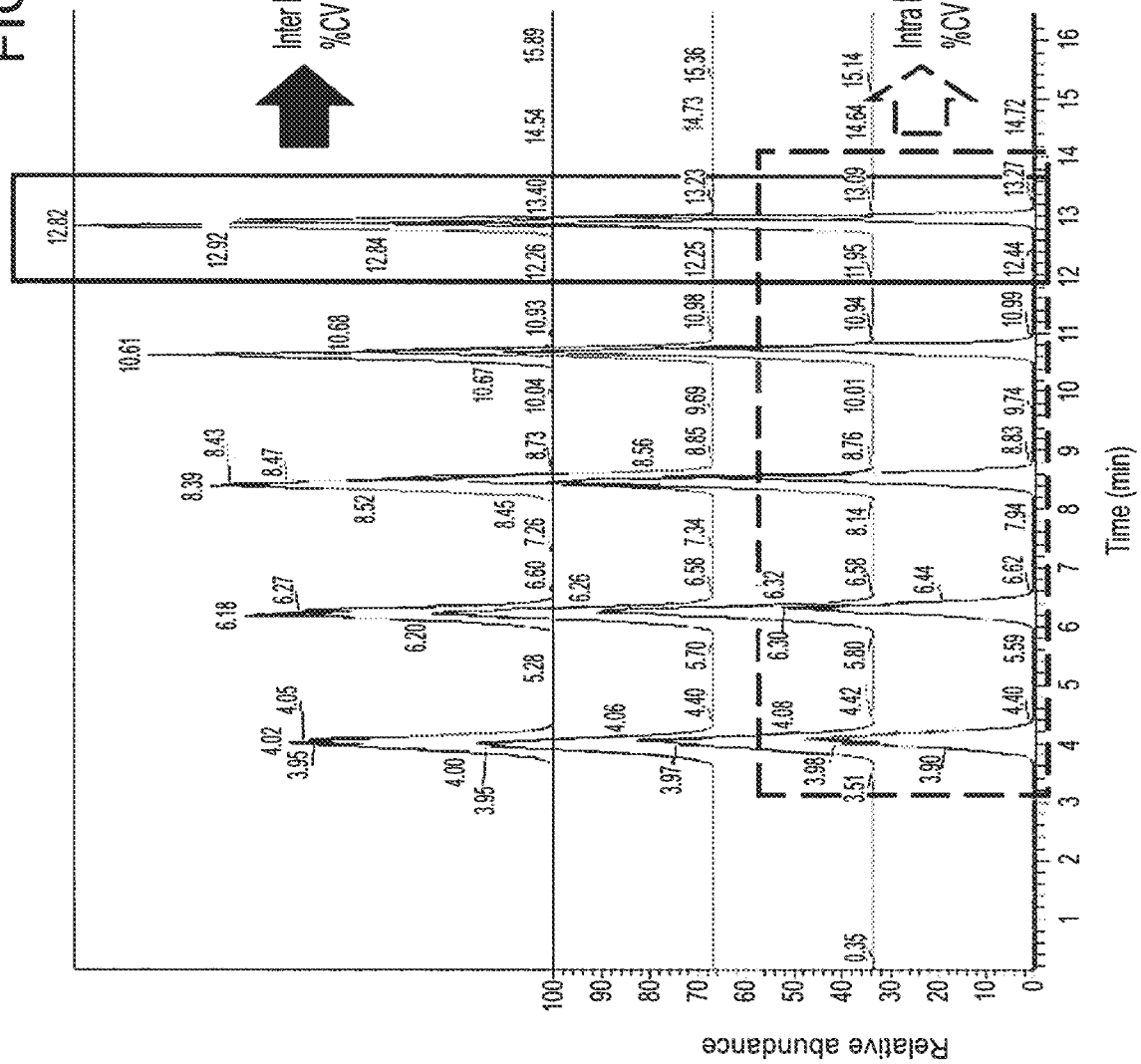
FIG. 14 depicts in accordance with various embodiments of the invention, the reproducibility of $BNP_{1-32}$ electropherograms of 5-segment electrokinetically injected multi-segment injection runs. The overlaid total ion chromatogram of four experiments, each consisting of 5 segments from recombinant $BNP_{1-32}$ protein in water (250 ng/mL). Intra-run reproducibility was assessed by comparing individual MSI segments within a run, while Inter-run reproducibility was assessed by comparing the same peak across four successive runs, both with respect to migration times (table, top left table) and peak area (table, bottom left). Segments were injected in 3 minute intervals within each run, and successive runs were performed at 1 hr intervals.

Capillary electrophoresis was performed using commercially available neutral CESI capillaries (Sun, L.; Knierman, M. D.; Zhu, G.; Dovichi, N. J., Fast top-down intact protein characterization with capillary zone electrophoresis-electrospray ionization tandem mass spectrometry. *Anal Chem* 2013, 85 (12), 5989-95; Neuberger, S.; Rafai, A.; Neususs, C., Screening of Small Intact Proteins by Capillary Electrophoresis Electrospray Ionization-Mass Spectrometry (CE-ESI-MS). *Methods Mol Biol* 2016, 1466, 43-56) that prevent adsorption and interaction of basic BNP peptidoforms and of intact cationic plasma proteins with the anionic silanol groups that constitute the inner surface of uncoated fused silica capillaries. We established baseline parameters by developing a method for CESI-MS analysis of standard $BNP_{1-32}$ dissolved in water. This sample was electrokinetically (Hirokawa, T.; Okamoto, H.; Gas, B., High-sensitive capillary zone electrophoresis analysis by electrokinetic injection with transient isotachophoretic preconcentration: electrokinetic supercharging. *Electrophoresis* 2003, 24 (3), 498-504) injected at 5 kV for 10 seconds into a capillary filled with a BGE of 10% acetic acid, and a separation voltage of 30 kV supplemented with a forward pressure of 0.5 psi was applied throughout the run. We tested the performance of our CESI-MS method by simultaneously analyzing peak migration times (Table 2) and peak areas (Table 3) for four successive runs consisting of five MSI segments each (FIG. 14). These experiments resulted in an average percent of coefficient of variance (% CV) between runs of 7% (N=4), and an average % CV between segments within a run of 21.6% (N=5). The overall average % CV for the combination of all segments and all runs was 20%. We found the migration time of the multiply injected peaks, the ESI spray, and the MS signal throughout the CE run to be stable and reproducible.

TABLE 2

Intra-run and inter-run migration time of $BNP_{1-32}$ of CESI-MS with 5 MSI

| | Migration time (min) | | | | |
| --- | --- | --- | --- | --- | --- |
| Run | MSI 1 | MSI 2 | MSI 3 | MSI 4 | MSI 5 |
| 1 | 4.02 | 6.18 | 8.39 | 10.61 | 12.82 |
| 2 | 4.00 | 6.20 | 8.52 | 10.68 | 12.92 |
| 3 | 4.06 | 6.23 | 8.45 | 10.67 | 12.86 |
| 4 | 4.08 | 6.32 | 8.56 | 10.73 | 12.97 |
| Std dev (inter-run) | 0.04 | 0.06 | 0.08 | 0.05 | 0.07 |

TABLE 3

Intra-run and inter-run peak area of $BNP_{1-32}$ by CESI-MS with MSI.

| | Peak Area | | | | | % CV (intra-run) | % CV (all runs combined) |
| --- | --- | --- | --- | --- | --- | --- | --- |
| Run | MSI 1 | MSI 2 | MSI 3 | MSI 4 | MSI 5 | | |
| 1 | 3.4E+08 | 3.4E+08 | 3.3E+08 | 2.9E+08 | 2.9E+08 | 8% | 20% |
| 2 | 3.7E+08 | 3.5E+08 | 3.6E+08 | 3.4E+08 | 3.1E+08 | 7% | |
| 3 | 3.1E+08 | 3.3E+08 | 3.3E+08 | 3.0E+08 | 2.8E+08 | 6% | |
| 4 | 2.2E+08 | 2.0E+08 | 2.2E+08 | 1.9E+08 | 1.8E+08 | 7% | |
| % CV (inter-run) | 22% | 23% | 20% | 22% | 21% | | |

Figure 15:
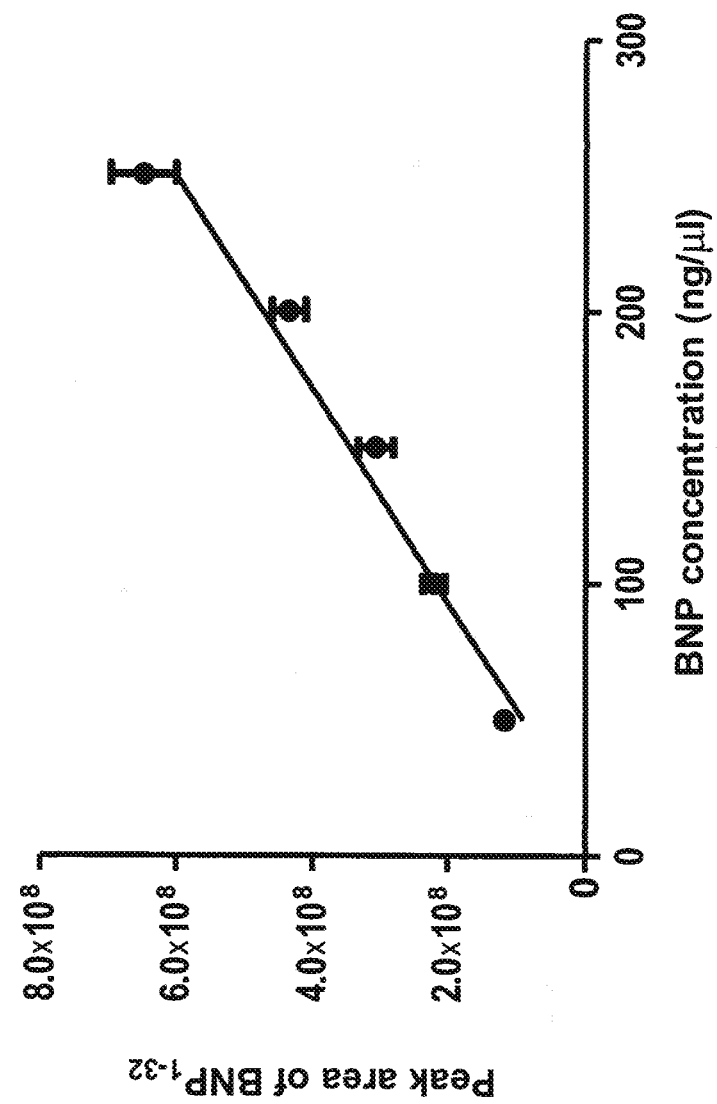
FIG. 15 depicts in accordance with various embodiments of the invention, the BNP dilution curve. The calibration curve is produced from three separate CESI-MS runs with electrokinetically injected multi-segment injection, each consisting of five segments of increasing recombinant $BNP_{1-32}$ concentrations separated by a background electrolyte spacer. Curve is based on all data points (mean+/−Std Dev).

We applied our method to analyze a dilution series of recombinant $BNP_{1-32}$ and generated a linear 5-point standard curve in a single run with five MSI sample injections (FIG. 15). The concentration range of $BNP_{1-32}$ for this curve was between 50 ng/µL to 250 ng/µL, and all concentrations produced well resolved Gaussian peaks. All five concentration points resulted in CVs under 15% (N=3) and accuracies between 89%-108% with the exception of the lowest concentration (50 ng/µL) whose accuracy was 130% (Table 4).

TABLE 4

Reproducibility and Accuracy of five $BNP_{1-32}$ calibration curves constructed as 5 MSI per curve.

| $BNP_{1-32}$ Concentration (ng/µL) | % CV | % Accuracy* |
|---|---|---|
| 50 | 12% | 130% |
| 100 | 13% | 101% |
| 150 | 15% | 89% |
| 200 | 10% | 92% |
| 250 | 13% | 108% |

*% accuracy is defined as the quantitative value of each peak from the calibration curve relative to its theoretical concentration, and is calculated using the average of replicates at the same concentration level.

CESI-MS for BNP Proteolytic Profiling in Plasma.

Figure 16:
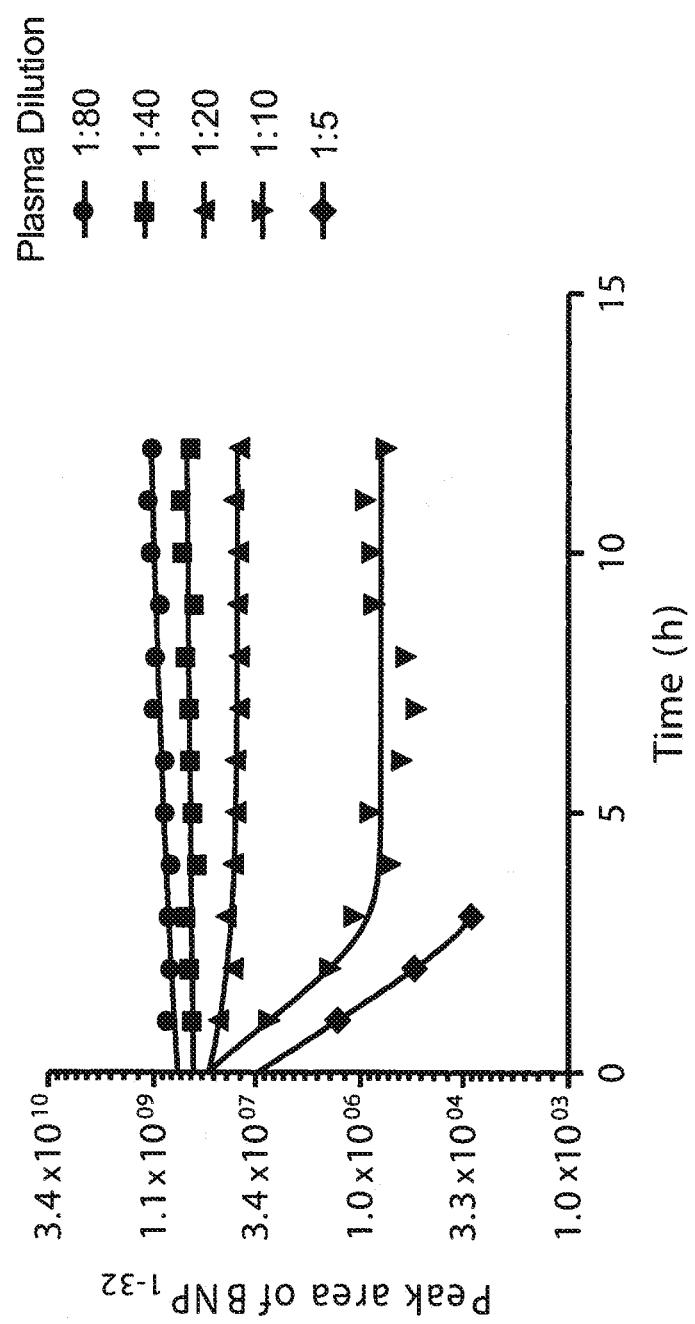
FIG. 16 depicts in accordance with various embodiments of the invention, Enzymatic profile of BNP. Profile of $BNP_{1-32}$ (250 ng/µL) pulsed into 5 different plasma dilutions (plasma:total volume). Samples were incubated inside the CE instrument at 25° C. and analyzed every hour for a sequence of 12 successive runs, each consisting of 5 simultaneously analyzed MSI segments representing $BNP_{1-32}$ from every plasma dilution. No quantifiable $BNP_{1-32}$ peak was detected beyond 4 hrs in the 1:5 plasma dilution.

In order to determine the optimal ratio at which enzymatic components in plasma degrade an exogenous pulse of $BNP_{1-32}$ while still being able to monitor substrate, we monitored $BNP_{1-32}$ in five parallel plasma dilutions that were analyzed simultaneously with MSI. Segments were injected electrokinetically into the capillary in decreasing order of dilution. Aside from the initial sample preparation and dilution, the incubation and successive overnight analyses were performed within and by the CE instrument as part of a sequence protocol. To our knowledge, this experiment represents the first analysis of proteins from a plasma matrix using a neutral-coated CESI-MS with MSI. This experiment demonstrated that overly diluted plasma (beyond 1:20) did not result in any appreciable $BNP_{1-32}$ degradation. Conversely, we could not detect $BNP_{1-32}$ beyond 12 hrs when plasma dilutions were 1:5 or less. A ratio of 1:10 allowed us to monitor decreasing $BNP_{1-32}$ peaks which remained quantifiable for 12 successive injections spanning 12 hrs (FIG. 16).

Figure 17A:
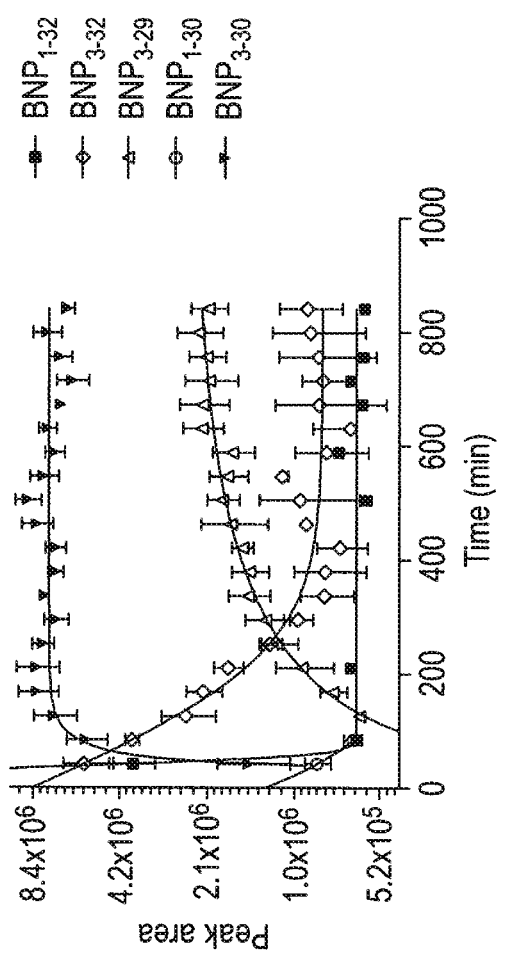
FIG. 17A-FIG. 17B depicts in accordance with various embodiments of the invention, Enzymatic proteolysis curves of BNP peptidoforms. Simultaneous profiling of five peptidoforms from 20 consecutive CESI-MS runs sampled after an initial 250 ng/µL pulse of $BNP_{1-32}$ into a plasma.
Figure 17B:
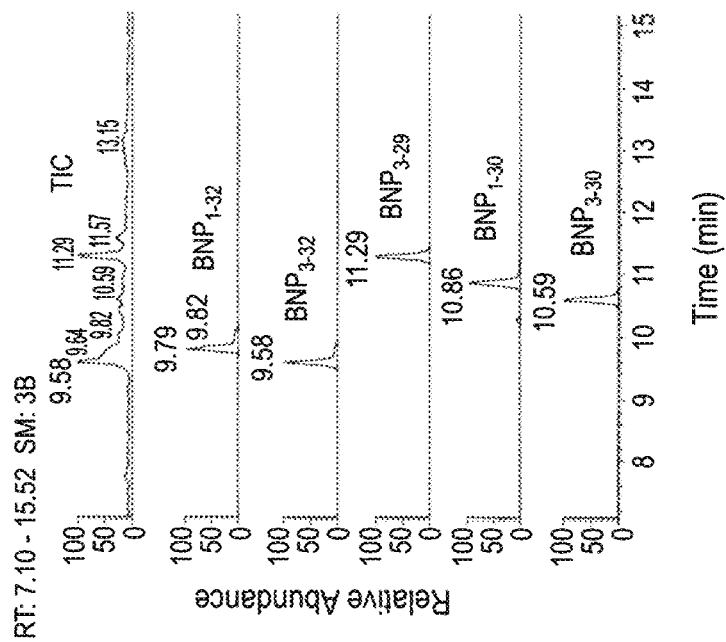

Over the course of our dilution series experiments, we observed the time-dependent appearance of additional BNP peaks as the degradation reaction proceeded, which we subsequently identified as BNP cleavage peptidoforms with the BioPharma Finder 1.0 Mass Informatics platform (ThermoFisher). We ultimately found that successive sampling across 14 hrs from an individual reaction vial enabled the quantitative detection and profiling of a total of five BNP peptidoforms enzymatically generated in plasma, namely $BNP_{1-32}$ and four of its cleavage peptidoforms: $BNP_{3-32}$, $BNP_{3-29}$, $BNP_{1-30}$, and $BNP_{3-30}$. Interestingly, the profiles with which these peptidoforms are detected suggest that products of one cleavage reaction may serve as substrates for other reactions. Accordingly, we propose that the simultaneous measurement of BNP peptidoforms over time is a measure of the collective enzymatic processes that catabolize BNP in a plasma sample (FIG. 17A-FIG. 17B).

One-Hour Proteolytic Profile by CESI-MS with MSI.

The prospective application of our proteolytic profiling technique for discovery and research cohorts, warrants the quantitative detection and profiling of as many peptidoforms as possible. The disadvantage inherent to a comprehensive characterization of $BNP_{1-32}$ along with its four BNP cleavage peptidoforms is its requirement for a 14 hr protocol to allow sufficient reaction time for the generation of slower-forming cleavage peptidoforms. We propose that incorporating MSI into the method can increase throughput by enabling the simultaneous analysis of multiple different plasma samples within a single MS run, thereby achieving a faster turnaround. Conversely, we also applied MSI orthogonally to sample a single individual reaction vial every 3 minutes for a total of 5 closely spaced time points. This iteration of our method can provide an acute quantitative profile of primary BNP proteolysis products, which we depict as the ratio of $BNP_{3-32}$:$BNP_{1-32}$, from plasma in less than one hour, including sample preparation. Although this 1 hr method under the current conditions can detect other peptidoforms, the short reaction time precludes a reliable signal with sufficient intensity for their quantitative analysis. Alternatively, adjusting the plasma dilution ratio may facilitate the quantitative analysis of slower-forming BNP peptidoforms within this 1 hr timeframe.

Figure 18:
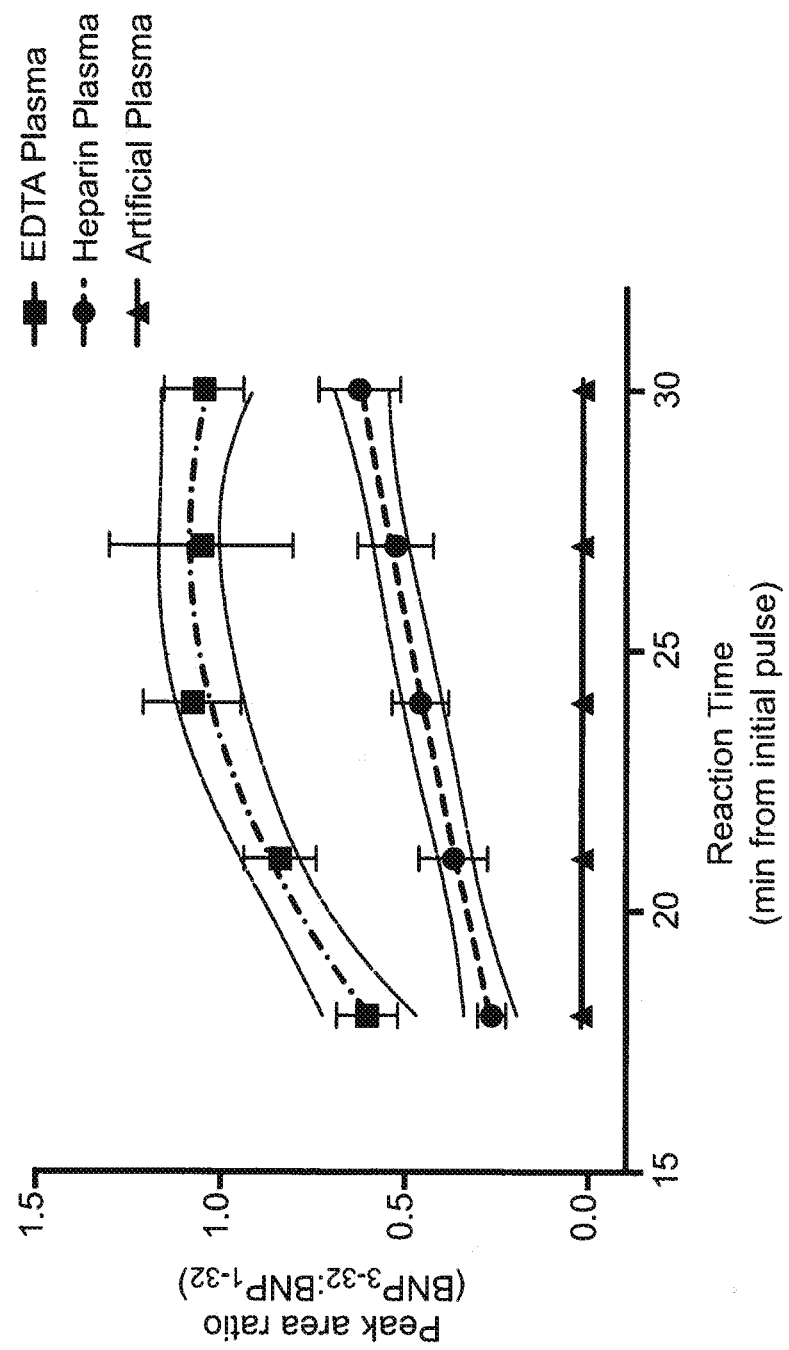
FIG. 18 depicts in accordance with various embodiments of the invention, the effect of Heparin versus EDTA plasma. Proteolytic profiles of exogenous $BNP_{1-32}$ (250 ng/µL) pulsed into 10× diluted EDTA, Heparin, and artificial plasma using neutral-coated CESI-MS with MSI (n=5, each). Samples were incubated on the CE autosampler at 25° C. for 18 min prior to selective electrokinetic injection of BNP peptidoforms using MSI with 3 min intervals (5 segments per run). Datapoints depict mean+/−Std Dev lines of best fit reflect quadratic nonlinear regression with 95% CI.
Figure 19:
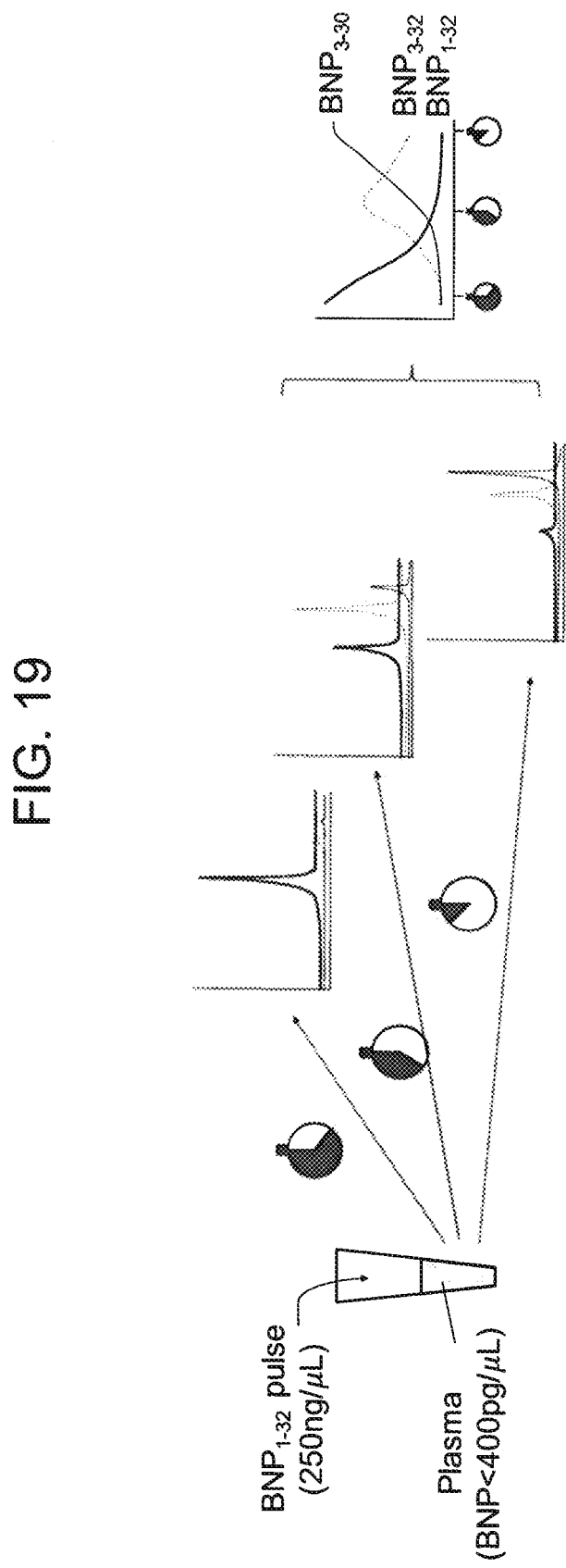
FIG. 19 depicts in accordance with various embodiment of the invention, the concept of our invention. Namely, we simultaneously analyze $BNP_{1-32}$, $BNP_{1-30}$, $BNP_{3-32}$, $BNP_{3-30}$, and $BNP_{3-29}$ from the sequential analyses of a sample into which $BNP_{1-32}$ is pulsed.
Figure 20:
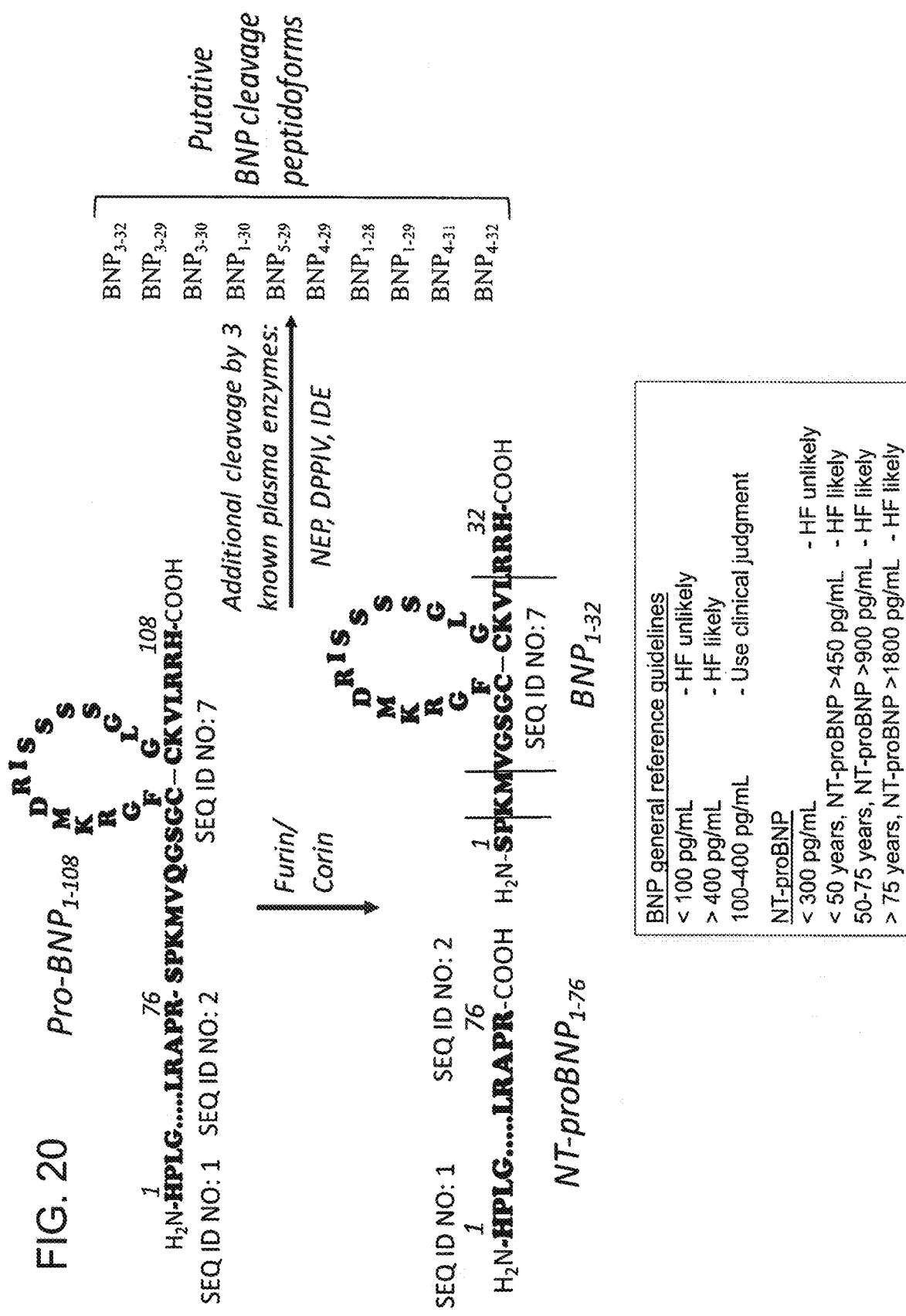
FIG. 20 depicts in accordance with various embodiments of the invention, the known physiological steps involved in $BNP_{1-32}$ secretion, as well as the known circulating enzymes involved in its further cleavage to ten putative cleavage peptidoforms, namely Neutral Endopeptidase (NEP), Dipeptidyl peptidase IV (DPPIV), and Insulin Degrading Enzyme (IDE).
Figure 21:
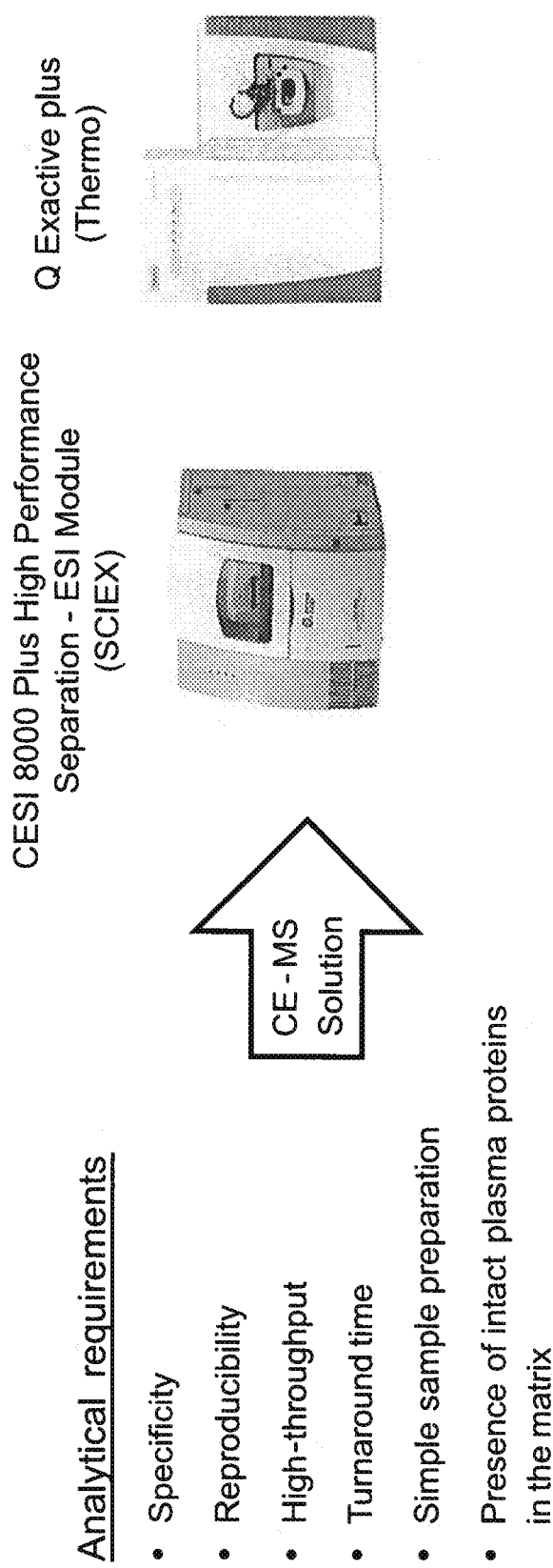
FIG. 21 depicts in accordance with various embodiments of the invention, the analytical requirements identified at the outset of the invention process (left) and the analytical setup used to address these (Right). Conclusion: linking Capillary Electrophoresis with Mass Spectrometry addresses the simplified sample preparation and intact proteins inherent to the method.
Figure 23:
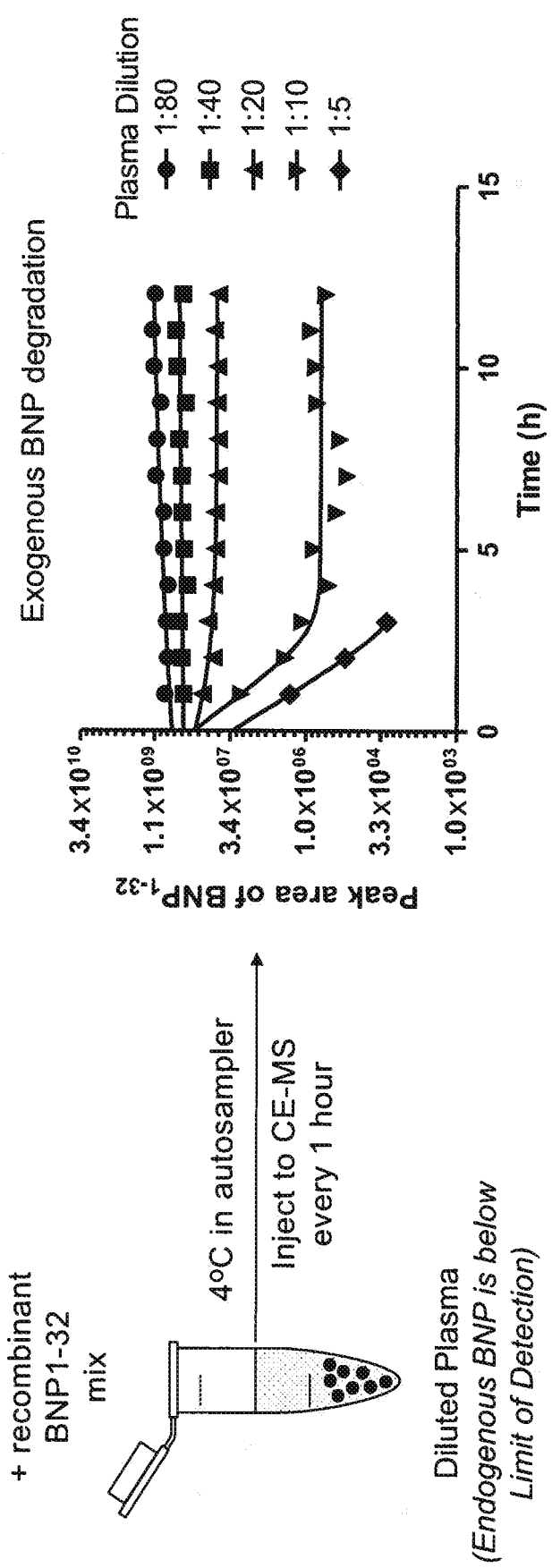
FIG. 23 depicts in accordance with various embodiments of the invention, the experimental outline used to define the useable plasma dilution. Conclusion: the 1:10 dilution provides a readout of $BNP_{1-32}$ degradation over a 12 hour timespan.
Figure 24:
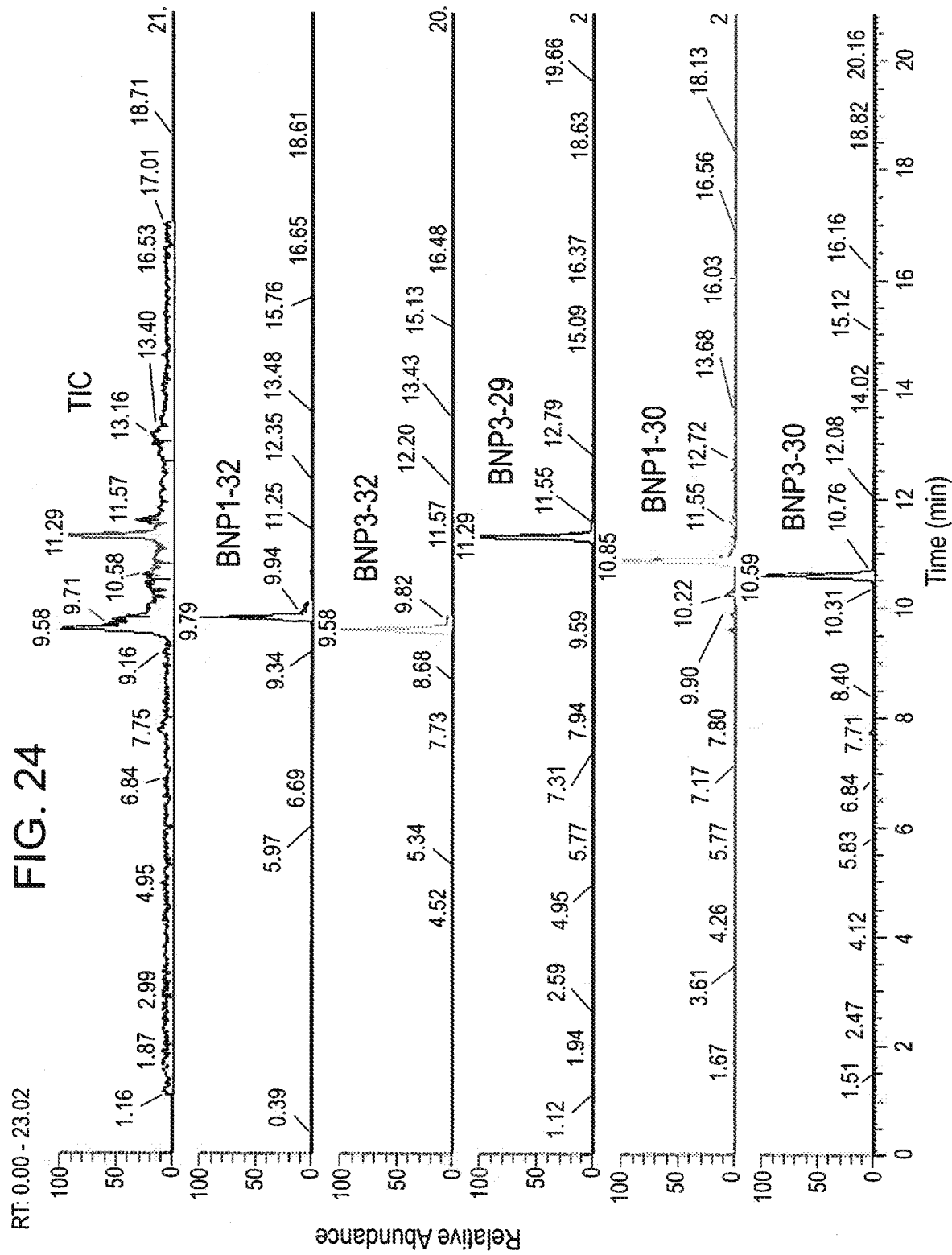
FIG. 24 depicts in accordance with various embodiments of the invention, total ion and extracted ion electropherograms for $BNP_{1-32}$, $BNP_{3-32}$, $BNP_{3-29}$, $BNP_{1-30}$ and $BNP_{3-30}$ from a single sample injection plug, showing the ability of the CESI-MS method to resolve the five peptidoforms of BNP, namely $BNP_{1-32}$, $BNP_{3-32}$, $BNP_{3-29}$, $BNP_{1-30}$, and $BNP_{3-30}$.
Figure 25:
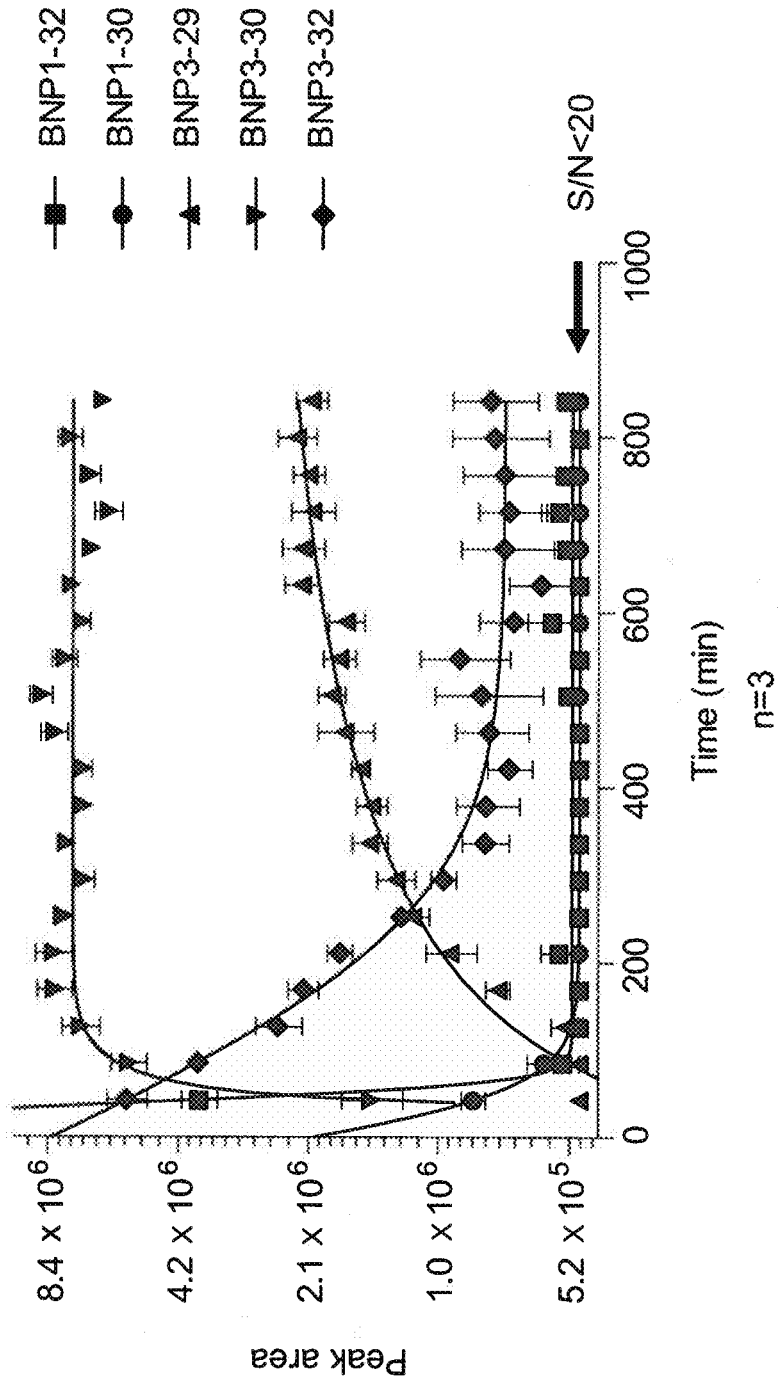
FIG. 25 depicts in accordance with various embodiments of the invention, the time course profile of $BNP_{1-32}$, $BNP_{3-32}$, $BNP_{3-29}$, $BNP_{1-30}$ and $BNP_{3-30}$ as individual peak areas over a total of 14 hrs post-pulse (n=3).
Figure 26:
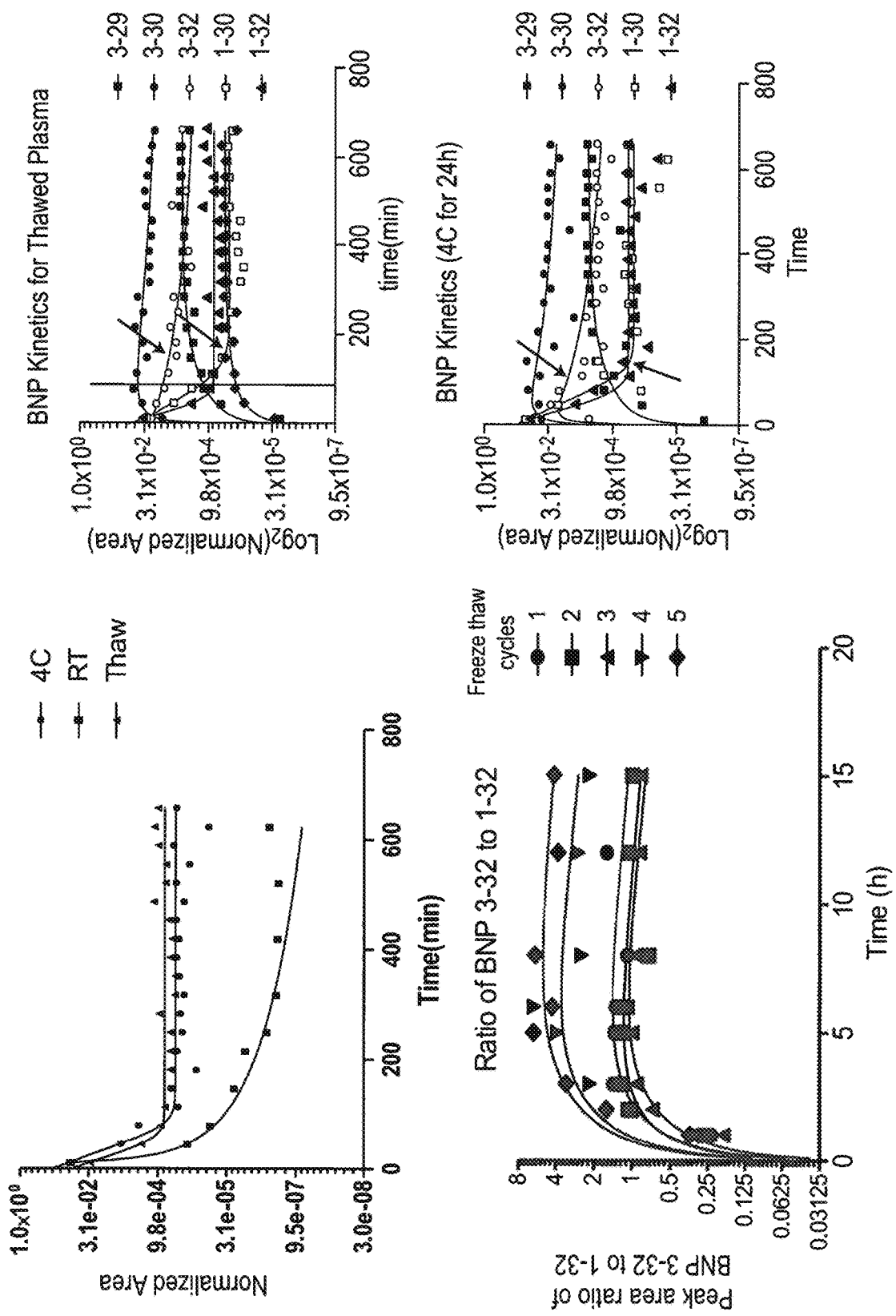
FIG. 26 depicts in accordance with various embodiments of the invention, the ability of our assay to distinguish BNP cleavage profiles according to different storage conditions over a 12 h timespan. Upper right panel: profile shows that plasma stored frozen (−80° C.) and thawed prior to analysis shows an equivalent cleavage profile for $BNP_{1-32}$ as plasma stored at 4° C. for 24 h, while plasma storage at room temperature showed an altered profile. Lower left panel: Cleavage profiles are similar up to 3 freeze-thaw cycles, but adversely affected by 4 or more freeze-thaw cycles. Right panels: Likewise, fresh-frozen plasma analyzed immediately upon thawing (upper right) resulted in a qualitatively dissimilar profile over 12 hrs to plasma stored for 24 hrs at 4° C. (right panels). Conclusion: This assay requires consistency in plasma storage; plasma should be stored at −80° C. upon sampling, and thawed immediately prior to analysis.
Figure 27:
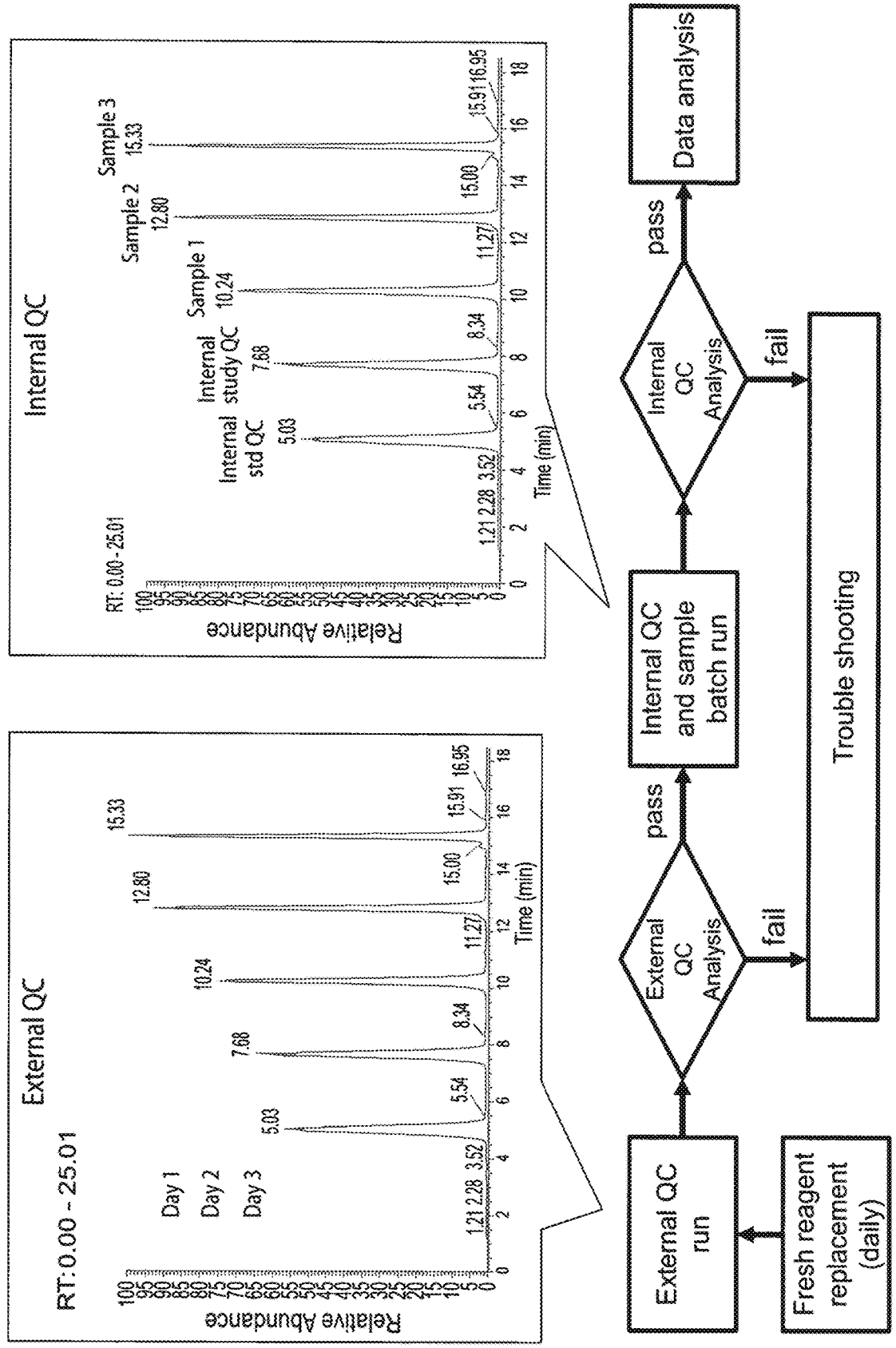
FIG. 27 depicts in accordance with various embodiments of the invention, a workflow, inherent to multi-segment injection, designed to incorporate external (day-to-day) and internal (analytical) QC. By incorporating one segment for an internal standard QC to monitor analytical and instrument performance, and a second segment for internal study QC to monitor non-enzymatic degradation, each run can be independently assessed for quality. An additional daily analysis of an external QC of freshly prepared $BNP_{1-32}$ in water can further evaluate instrument performance prior to routine clinical analysis.
Figure 28:
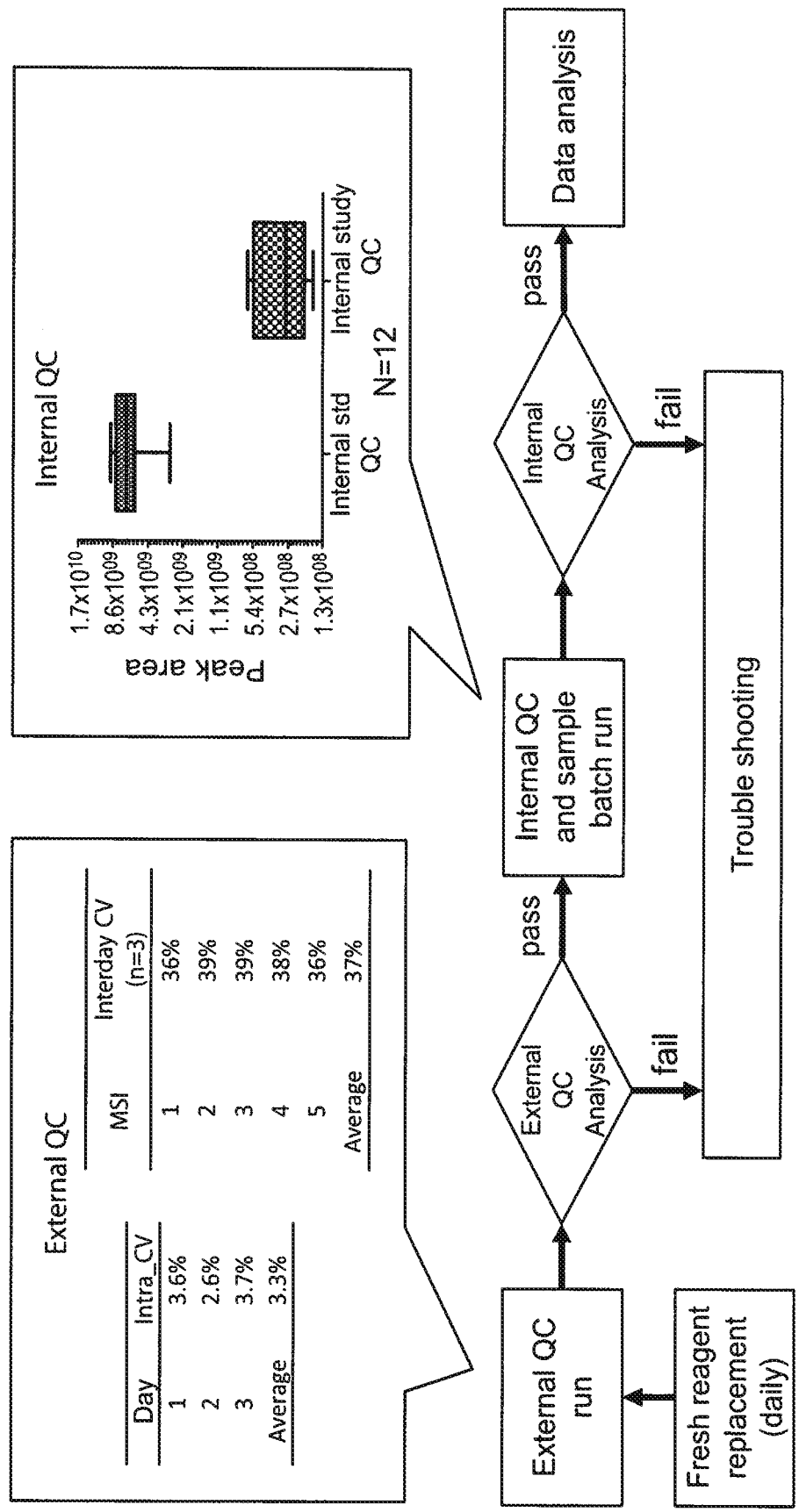
FIG. 28 depicts in accordance with various embodiments of the invention, representative results of incorporating internal standard QC and internal study QC metrics as two separate segments for multi-segment injection CESI-MS for BNP cleavage profiling in plasma.
Figure 29:
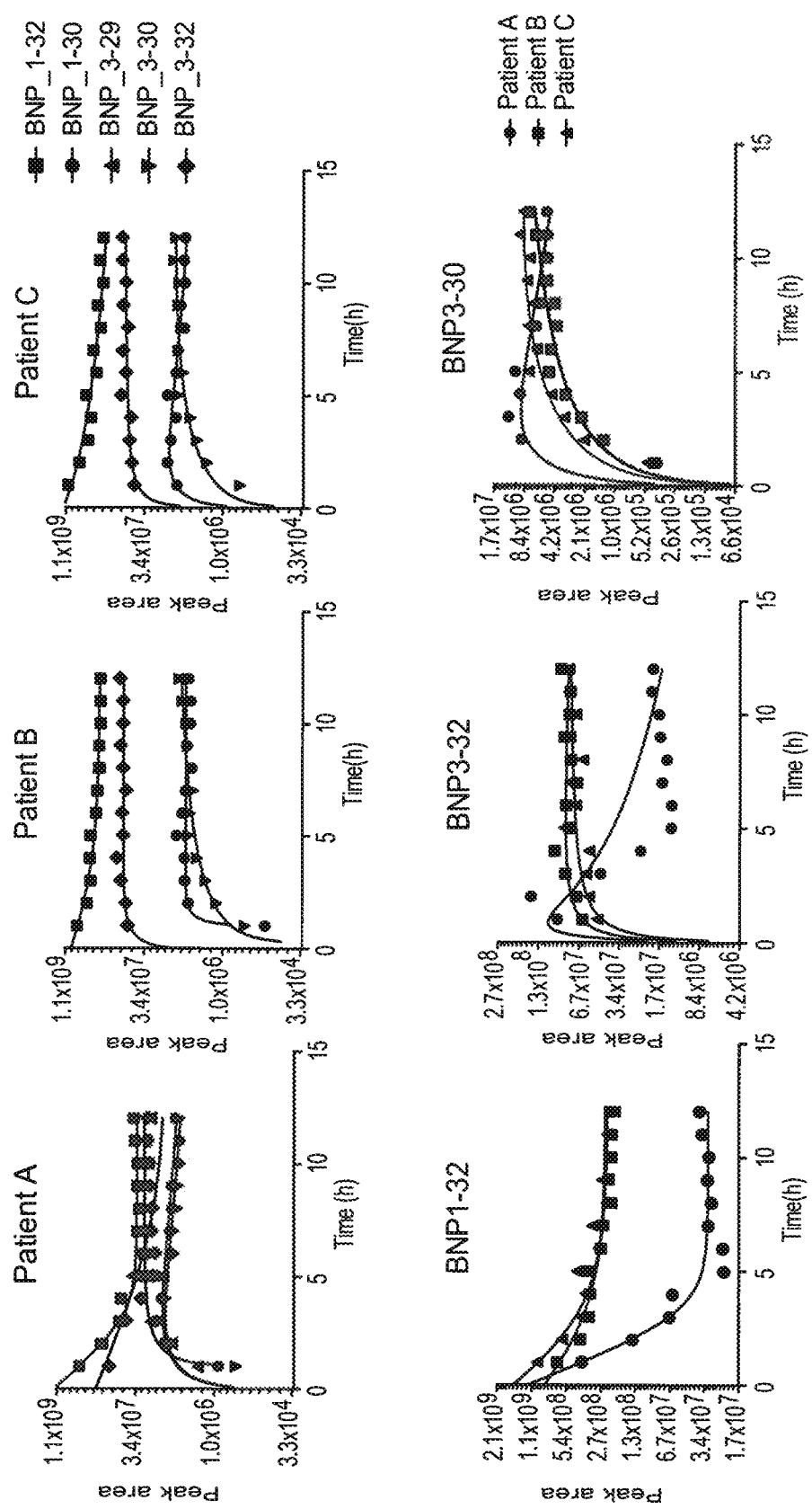
FIG. 29 depicts in accordance with various embodiments of the invention, differential BNP peptidoform profiles for three patients across a 12 hr timeframe. Upper panels show qualitative differences in the combined profiles for $BNP_{1-32}$, and its cleavage peptidoforms $BNP_{1-30}$, $BNP_{3-29}$, $BNP_{3-30}$, and $BNP_{3-32}$, within plasma three different patients. Lower panels separately show differential profiles for $BNP_{1-32}$, $BNP_{3-32}$, $BNP_{3-30}$ between three patients.
Figure 31:
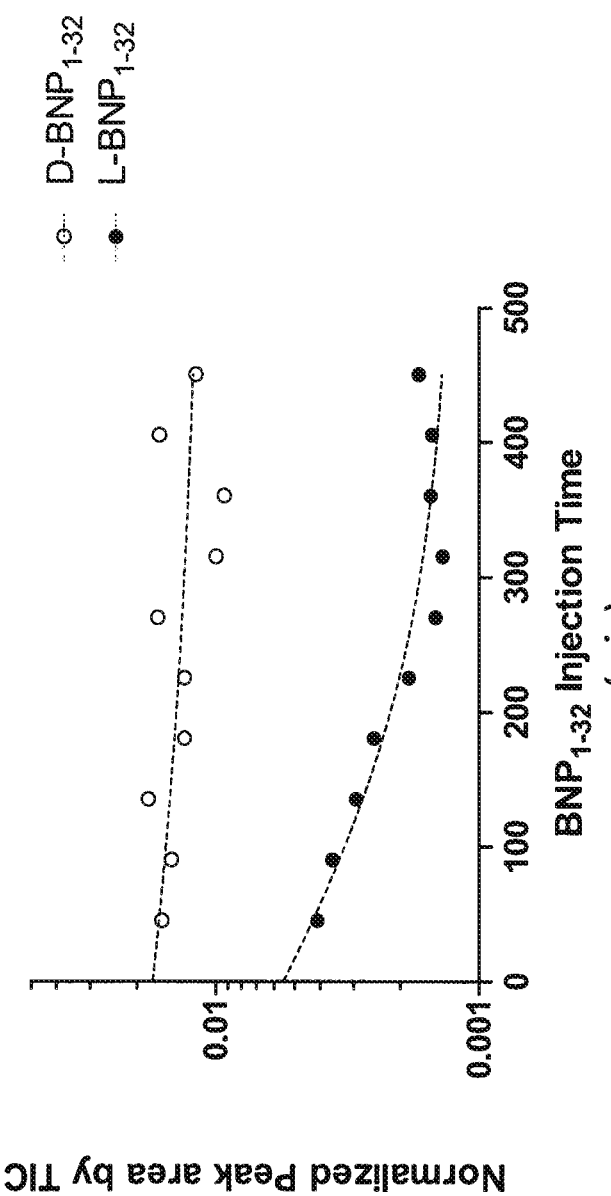
FIG. 31 depicts in accordance with various embodiments of the invention, $L-BNP_{1-32}$ and $D-BNP_{1-32}$ enantiomer degradation profiles in plasma.
Figure 32:
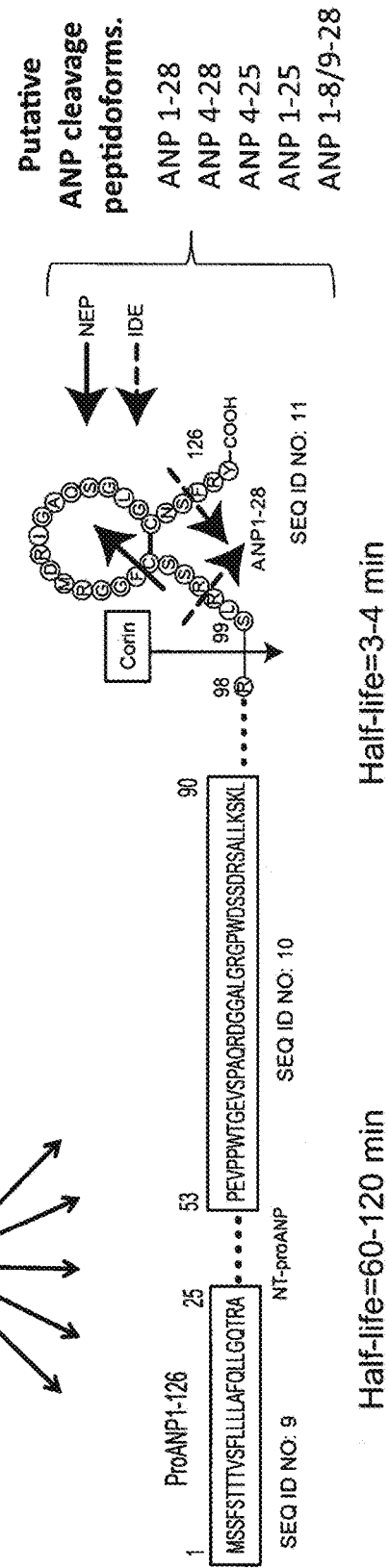
FIG. 32 depicts in accordance with various embodiments of the invention, a representation of Atrial Natriuretic Peptide (ANP) as well as its putative cleavage peptidoforms.
Figure 33:
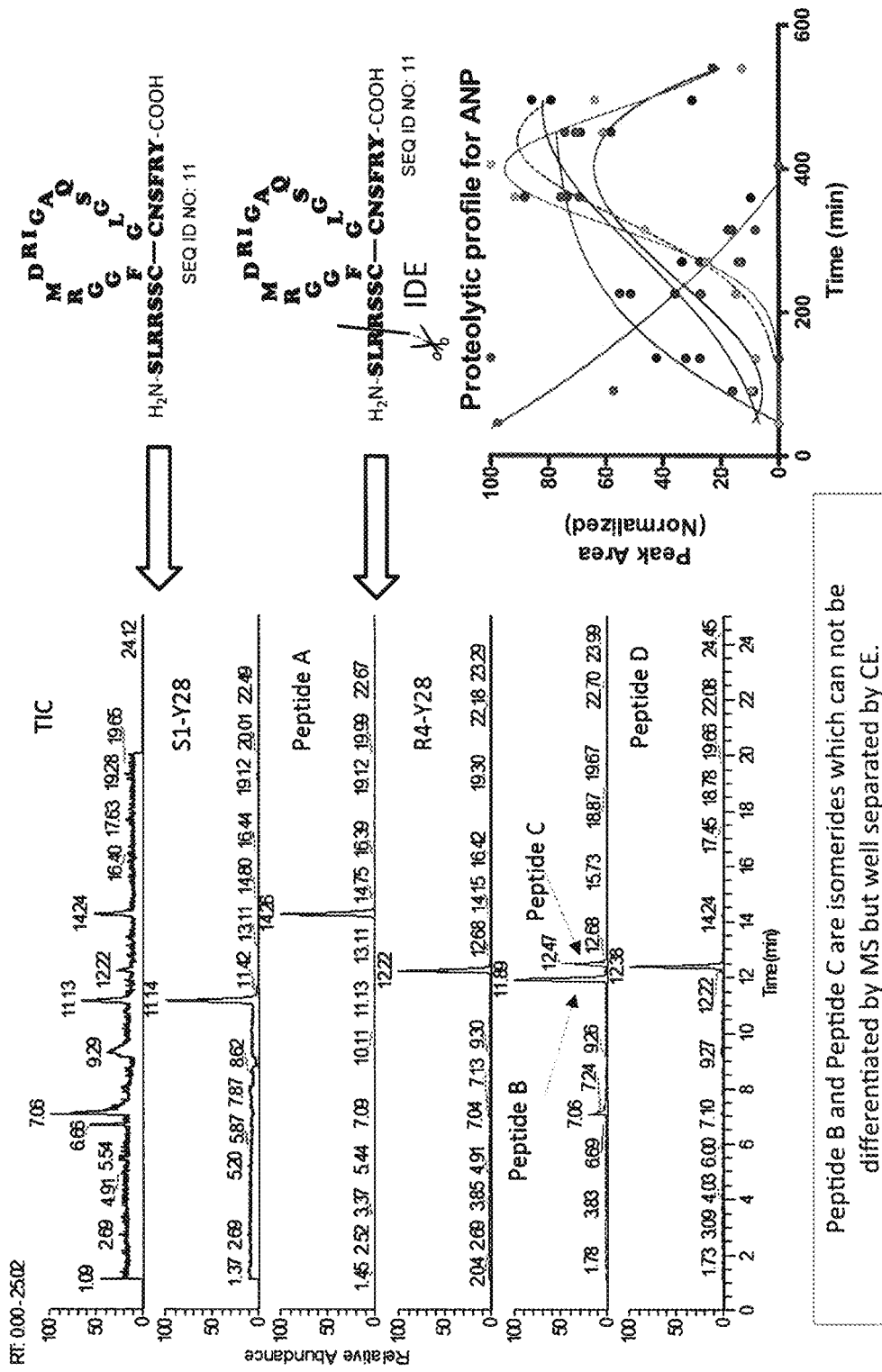
FIG. 33 depicts in accordance with various embodiments of the invention, the total ion chromatograph as well as the extracted ion chromatographs of Atrial Natriuretic Peptide (ANP) and four of its proteolytic peptides resulting from cleavage in plasma (left panel). The proteolytic profiles of these peptides, as they are generated in a plasma sample, were analyzed across ten time points and plotted on the lower left panel. This analysis was performed using Capillary Electrophoresis-Mass Spectrometry as described in this patent application.

EDTA and heparin collection tubes are commonplace for plasma sampling in the hospital setting. Buckley et al (Belenky, A.; Smith, A.; Zhang, B.; Lin, S.; Despres, N.; Wu, A. H.; Bluestein, B. I., The effect of class-specific protease inhibitors on the stabilization of B-type natriuretic peptide in human plasma. Clin Chim Acta 2004, 340 (1-2), 163-72) suggested EDTA collection tubes be employed where BNP analysis from plasma is concerned when using traditional radioimmunoassay-based methods. While our results clearly indicate that endogenous plasma proteases retain their ability to cleave $BNP_{1-32}$ after plasma collection, our study was not designed to assess the extent to which protease activities alter the quantitative accuracy of immunoassay-based methods. Neither was this study designed to assess the suitability of various sampling tubes as they pertain to CESI-MS-based profiling of BNP proteolysis. Nevertheless, our assay provides a measure of the outcome of all plasma proteases that degrade BNP, providing a biological readout of the underlying physiology or pathophysiology. Furthermore, as an initial application for our 1-hr detection method, we performed a pilot side-by-side analysis to compare human plasma collected in either Heparin tubes or EDTA tubes (FIG. 18). In one hour, our method clearly describes a difference in the profiles of $BNP_{1-32}$:$BNP_{3-32}$ between plasma collected in these two common tubes. Among the enzymes known to cleave BNP, both insulin degrading enzyme (IDE) and neutral endopeptidase (NEP) are known to use $Zn^{2+}$ as a cofactor (Shen, Y.; Joachimiak, A.; Rosner, M. R.; Tang, W. J., Structures of human insulin-degrading enzyme reveal a new substrate recognition mechanism. Nature 2006, 443 (7113), 870-4; Oefner, C.; Rogues, B. P.; Fournie-Zaluski, M. C.; Dale, G. E., Structural analysis of neprilysin with various specific and potent inhibitors. Acta Crystallogr D Biol Crystallogr 2004, 60 (Pt 2), 392-6; Oefner, C.; Pierau, S.; Schulz, H.; Dale, G. E., Structural studies of a bifunctional inhibitor of neprilysin and DPP-IV. Acta Crystallogr D Biol Crystallogr 2007, 63 (Pt 9), 975-81). IDE can cut the last 3 amino acids from the C-terminal of BNP while NEP can cleavage between the fourth and fifth amino acids from N-terminal in reactions required to produce the primary proteolysis products of BNP (Volpe, M.; Rubattu, S.; Burnett, J., Jr., Natriuretic peptides in cardiovascular diseases: current use and perspectives. Eur Heart J 2014, 35 (7), 419-25). We have previously detected $BNP_{3-29}$ in plasma from heparin collection tubes within an hour, but not from EDTA tubes which require substantially longer incubation times. Without being bound by theory, we hypothesize that the activity of IDE may be partially inhibited by EDTA due to its chelation of Zinc ions.

Both the plasma dilution series and the absence of $BNP_{1-32}$ degradation was the product of previously described enzymatic activities in plasma samples, we measured the time-dependent ratio of $BNP_{1-32}$:$BNP_{3-32}$ of the $BNP_{1-32}$ pulsed into a commercially available human plasma matrix along with the same ratio that is also pulsed into an artificial plasma matrix consisting of albumin dissolved in PBS. In contrast with the human plasma matrix, a small amount of $BNP_{3-32}$ was consistently detected in the artificial plasma group, but the $BNP_{1-32}$:$BNP_{3-32}$ ratio was stable (FIG. 18). We did not detect any signals for $BNP_{3-29}$, $BNP_{1-30}$, or $BNP_{3-30}$ in artificial plasma across the timespan of this experiment, and without being bound by theory we hypothesize that the residual $BNP_{3-32}$ peak represents a low-level degradation product. However, these data confirm that the degradation of $BNP_{1-32}$ that we detect in human plasma is enzyme mediated.

In this study, we present a novel approach in which BNP cleavage peptidoforms are profiled using CESI-MS, as they are enzymatically generated over time in minimally processed plasma. In our approach, standard exogenous $BNP_{1-32}$ is pulsed into a plasma sample, where endogenous plasma peptidases cleave BNP to produce various product peptidoforms. This reaction can proceed in a temperature-controlled sample vial, and selectively sampled into a capillary using electrokinetic injection at any desired time interval. We present the first use of MSI with CESI-MS using a neutral coated capillary for proteins in plasma. The use of MSI can endow this method with increased throughput via parallel analysis of multiple plasma samples. In this case, each parallel sample would be represented by an individual sequentially injected segment, and successive CESI-MS runs would provide a time course profile for BNP peptidoform formation across an entire CE sequence. Similarly, we applied MSI orthogonally to the same sample, producing a multi-point BNP peptidoform profile from an individual plasma sample across the protracted timeframe of a single CESI-MS run. This second iteration of our method produces a 5-point profile in under an hour, including all sample preparation steps.

Example 1

250 ng/uL D-BNP and 250 ng/uL L-BNP were separately spiked in the same human plasma sample containing EDTA. The samples were incubated inside the CE instrument at 25° C. and analyzed every 45 min for a sequence of 10 successive runs. After 450 min, L-BNP was significantly degraded, while D-BNP maintained its concentration generally and no degradation product was detected (see FIG. 1). In this example, each chiral amino acid (or chiral amino acid residue) in the D-BNP was a D-amino acid (or D-amino acid residue). In other words, the D-BNP used in this specific example did not contain any L-amino acids (or L-amino acid residues).

Example 2

Add non-natural $BNP_{1-32}$ into human plasma, in parallel with cleavable synthetic $BNP_{1-32}$. Sequentially sample and analyze this mixture with CESI-MS to determine the extent to which either or both peptides are cleaved within one hour.

Example 3

Add non-natural $BNP_{1-32}$ into human plasma, in parallel with cleavable synthetic $BNP_{1-32}$. Sequentially sample and analyze this mixture with CESI-MS to determine the extent to which either or both peptides are cleaved overnight.

Example 4

Mix equimolar ratios of non-natural $BNP_{1-32}$ and cleavable synthetic $BNP_{1-32}$ into water and perform CESI-MS. Without being bound by theory, the non-natural $BNP_{1-32}$ and the cleavable synthetic $BNP_{1-32}$ have equivalent electrophoretic mobilities and are indistinguishable in the MS.

Example 5

Without being bound by theory, synthesize all detectable and relevant BNP peptidoforms in their non-natural, non-enzymatically cleavable enantiomeric forms. In other words, artificially synthesize any non-natural BNP peptidoforms, wherein one or more L-amino acids (or L-amino acid residues) in the natural BNP peptidoform is replaced with one or more D-amino acids (or D-amino acid residues).

Example 6

Endogenous BNP and its cleavage products are directly detected in the sample. Without being bound by theory, this is performed using highly sensitive instrumentation or by enrichment of the endogenous BNP and/or its cleavage products using an antibody (or any capture method). In this example, the enrichment is performed using an anti-BNP antibody directed to the loop or central region that is common to endogenous BNP and the majority of the cleavage products that are produced in vivo. The quantification of endogenous BNP and/or any of its cleavage products are achieved by adding in D-BNP and/or one or more of its artificially synthesized cleavage peptidoforms prior to or after enrichment of the endogenous BNP and/or its cleavage products. The analysis of the endogenous BNP and/or any of its cleavage products, and the D-BNP and/or one or more of its artificially synthesized cleavage peptidoforms is analyzed using mass spectrometry.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention.

What is claimed is:

1. A method of detecting two or more cleavage products of one or more natriuretic peptides in a biological sample, comprising:
    obtaining a biological sample from a subject, wherein the biological sample comprises one or more proteases, wherein the biological sample is plasma, blood, or serum, and wherein the subject is at risk of developing cardiovascular disease;
    adding a quantity of one or more natriuretic peptides to the biological sample, wherein the natriuretic peptides are selected from the group consisting of brain natriuretic peptide (BNP) and atrial natriuretic peptide (ANP);
    incubating the biological sample to form an incubated sample;
    injecting the incubated sample into a separation capillary of a capillary electrophoresis/electrospray ionization mass spectrometer;
    operating the capillary electrophoresis/electrospray ionization mass spectrometer to detect two or more cleavage products of the one or more natriuretic peptides over a period of time; and
    detecting the two or more cleavage products of the one or more natriuretic peptides, wherein the cleavage products are selected from the group consisting of BNP 3-30, BNP 3-29, BNP 3-32, BNP 1-30, BNP 1-29, BNP 1-28, BNP 2-31, BNP 4-30, BNP 4-29, BNP 4-27, BNP 5-32, BNP 5-31, BNP 5-29, BNP 4-32, BNP 4-31, ANP 4-28, ANP 4-25, ANP 1-25, ANP 1-8, and ANP 9-28.

2. The method of claim 1, further comprising selecting a treatments for cardiovascular disease for the subject, wherein the treatment is selected from the group consisting of pharmacological therapy, surgery, and combinations thereof.

3. The method of claim 1, wherein the proteases are selected from the group consisting of neutral endopeptidase, dipeptidylpeptidase IV, and insulin degrading enzyme.

4. The method of claim 1, wherein the period of time is up to 1 hour.

5. The method of claim 1, wherein the period of time is up to 14 hours.

6. The method of claim 1, wherein the cleavage products are selected from the group consisting of BNP 3-30, BNP 3-29, BNP 3-32, and BNP 1-30.

7. The method of claim 1, wherein the cleavage products are selected from the group consisting of BNP 3-30, BNP 3-29, BNP 3-32, BNP 1-30, BNP 5-29, BNP 4-29, BNP 1-28, BNP 1-29, BNP 4-31, and BNP 4-32.

8. The method of claim 6, wherein the cleavage products are not modified.

9. The method of claim 6, wherein the cleavage products are modified.

10. The method of claim 9, wherein the modification is oxidation at the methionine residue.

11. The method of claim 1, wherein the quantity of one or more natriuretic peptides added to the sample is about any one or more of 10 ng/µL, 50 ng/µL, 75 ng/µL, 100 ng/µL, 125 ng/µL, 150 ng/µL, 175 ng/µL, 200 ng/µL, 225 ng/µL, 250 ng/µL, 275 ng/µL, 300 ng/µL, 350 ng/µL, 375 ng/µL, 400 ng/µL, 450 ng/µL, 475 ng/µL, or 500 ng/µL.

12. The method of claim 1, wherein the cardiovascular disease is heart failure, arterial fibrillation or combination thereof.

13. The method of claim 1, further comprising: comparing the two or more cleavage products of the one or more natriuretic peptides from the subject to two or more cleavage products of one or more natriuretic peptides from a reference sample.

14. The method of claim 13, further comprising: making an assessment of the subject based on the comparison, wherein the assessment is a determination of the risk of developing cardiovascular disease.

15. The method of claim 13, wherein the reference sample is obtained from a healthy subject.

16. The method of claim 13, wherein the reference sample is obtained from a subject that has been treated for cardiovascular disease.

17. The method of claim 13, wherein the reference sample is obtained from the subject at an earlier point in time.

18. The method of claim 13, wherein the reference sample is obtained from the subject before the subject is treated for cardiovascular disease.

19. The method of claim 1, further comprising detecting the one or more natriuretic peptides over a period of time.

20. A method of obtaining a proteolytic profile of two or more cleavage products of one or more L-natriuretic peptides, in a biological sample, the method comprising:
   obtaining a biological sample from a subject, wherein the biological sample comprises one or more proteases, and wherein the biological sample is plasma, blood, or serum;
   adding an amount of one or more L-natriuretic peptides to the biological sample, wherein the L-natriuretic peptides are selected from the group consisting of natural brain natriuretic peptide (natural BNP), natural atrial natriuretic peptide (natural ANP), cleavable synthetic brain natriuretic peptide (cleavable synthetic BNP), and cleavable synthetic atrial natriuretic peptide (cleavable synthetic ANP);
   adding an amount of an internal standard to the biological sample, wherein the internal standard comprises one or more non-natural natriuretic peptides, one or more non-natural cleavage peptidoforms, or a combination thereof;
   incubating the biological sample to form an incubated sample;
   injecting the incubated sample into a separation capillary of a capillary electrophoresis/electrospray ionization mass spectrometer;
   operating the capillary electrophoresis/electrospray ionization mass spectrometer to detect an amount of two or more cleavage products of the one or more L-natriuretic peptides and an amount of the internal standard over a period of time; and
   detecting the amount of the two or more cleavage products of the one or more L-natriuretic peptides and the amount of the internal standard, wherein the cleavage products are selected from the group consisting of BNP 3-30, BNP 3-29, BNP 3-32, BNP 1-30, BNP 1-29, BNP 1-28, BNP 2-31, BNP 4-30, BNP 4-29, BNP 4-27, BNP 5-32, BNP 5-31, BNP 5-29, BNP 4-32, BNP 4-31, ANP 4-28, ANP 4-25, ANP 1-25, ANP 1-8, and ANP 9-28.

21. The method of claim 1, further comprising administering a treatment for cardiovascular disease to the subject, wherein the treatment is selected from the group consisting of pharmacological therapy, surgery, and combinations thereof.

22. The method of claim 20, further comprising quantifying the amount of the two or more L-natriuretic peptide cleavage products by comparing the amount of two or more L-natriuretic peptide cleavage products with the amount of the internal standard to obtain a proteolytic profile of the subject.

23. The method of claim 22, further comprising comparing the proteolytic profile from the subject to a proteolytic profile from a reference sample, and making an assessment of the subject based on the comparison, wherein the assessment is a diagnosis of cardiovascular disease.

24. The method of claim 23, further comprising administering a treatment for cardiovascular disease to the subject, selecting a treatment for cardiovascular disease for the subject, or providing a treatment for cardiovascular disease for the subject based on the assessment, wherein the treatment is selected from the group consisting of pharmacological therapy, surgery, and combinations thereof.

* * * * *

SEQUENCE LISTING

```
<160> NUMBER OF SEQ ID NOS: 12

<210> SEQ ID NO 1
<211> LENGTH: 4
<212> TYPE: PRT
<213> ORGANISM: Artificial Sequence
<220> FEATURE:
<223> OTHER INFORMATION: Synthetic

<400> SEQUENCE: 1

His Pro Leu Gly
1

<210> SEQ ID NO 2
<211> LENGTH: 5
<212> TYPE: PRT
<213> ORGANISM: Artificial Sequence
<220> FEATURE:
<223> OTHER INFORMATION: Synthetic

<400> SEQUENCE: 2

Leu Arg Ala Pro Arg
1               5

<210> SEQ ID NO 3
<211> LENGTH: 30
```

```
<212> TYPE: PRT
<213> ORGANISM: Artificial Sequence
<220> FEATURE:
<223> OTHER INFORMATION: Synthetic

<400> SEQUENCE: 3

Ser Pro Lys Met Val Gly Ser Gly Cys Phe Cys Arg Lys Met Asp Arg
1               5                   10                  15

Ile Ser Ser Ser Gly Leu Cys Cys Lys Val Leu Arg Arg His
            20                  25                  30

<210> SEQ ID NO 4
<211> LENGTH: 134
<212> TYPE: PRT
<213> ORGANISM: Artificial Sequence
<220> FEATURE:
<223> OTHER INFORMATION: preproBNP

<400> SEQUENCE: 4

Met Asp Pro Gln Thr Ala Pro Ser Arg Ala Leu Leu Leu Leu Leu Phe
1               5                   10                  15

Leu His Leu Ala Phe Leu Gly Gly Arg Ser His Pro Leu Gly Ser Pro
            20                  25                  30

Gly Ser Ala Ser Asp Leu Glu Thr Ser Gly Leu Gln Glu Gln Arg Asn
        35                  40                  45

His Leu Gln Gly Lys Leu Ser Glu Leu Gln Val Glu Gln Thr Ser Leu
    50                  55                  60

Glu Pro Leu Gln Glu Ser Pro Arg Pro Thr Gly Val Trp Lys Ser Arg
65                  70                  75                  80

Glu Val Ala Thr Glu Gly Ile Arg Gly His Arg Lys Met Val Leu Tyr
                85                  90                  95

Thr Leu Arg Ala Pro Arg Ser Pro Lys Met Val Gln Gly Ser Gly Cys
            100                 105                 110

Phe Gly Arg Lys Met Asp Arg Ile Ser Ser Ser Gly Leu Gly Cys
        115                 120                 125

Lys Val Leu Arg Arg His
        130

<210> SEQ ID NO 5
<211> LENGTH: 108
<212> TYPE: PRT
<213> ORGANISM: Artificial Sequence
<220> FEATURE:
<223> OTHER INFORMATION: proBNP

<400> SEQUENCE: 5

His Pro Leu Gly Ser Pro Gly Ser Ala Ser Asp Leu Glu Thr Ser Gly
1               5                   10                  15

Leu Gln Glu Gln Arg Asn His Leu Gln Gly Lys Leu Ser Glu Leu Gln
            20                  25                  30

Val Glu Gln Thr Ser Leu Glu Pro Leu Gln Glu Ser Pro Arg Pro Thr
        35                  40                  45

Gly Val Trp Lys Ser Arg Glu Val Ala Thr Glu Gly Ile Arg Gly His
    50                  55                  60

Arg Lys Met Val Leu Tyr Thr Leu Arg Ala Pro Arg Ser Pro Lys Met
65                  70                  75                  80

Val Gln Gly Ser Gly Cys Phe Gly Arg Lys Met Asp Arg Ile Ser Ser
                85                  90                  95

Ser Ser Gly Leu Gly Cys Lys Val Leu Arg Arg His
```

```
              100                 105
```

<210> SEQ ID NO 6
<211> LENGTH: 76
<212> TYPE: PRT
<213> ORGANISM: Artificial Sequence
<220> FEATURE:
<223> OTHER INFORMATION: NT-proBNP

<400> SEQUENCE: 6

```
His Pro Leu Gly Ser Pro Gly Ser Ala Ser Asp Leu Glu Thr Ser Gly
1               5                   10                  15

Leu Gln Glu Gln Arg Asn His Leu Gln Gly Lys Leu Ser Glu Leu Gln
            20                  25                  30

Val Glu Gln Thr Ser Leu Glu Pro Leu Gln Glu Ser Pro Arg Pro Thr
        35                  40                  45

Gly Val Trp Lys Ser Arg Glu Val Ala Thr Glu Gly Ile Arg Gly His
    50                  55                  60

Arg Lys Met Val Leu Tyr Thr Leu Arg Ala Pro Arg
65                  70                  75
```

<210> SEQ ID NO 7
<211> LENGTH: 32
<212> TYPE: PRT
<213> ORGANISM: Artificial Sequence
<220> FEATURE:
<223> OTHER INFORMATION: BNP

<400> SEQUENCE: 7

```
Ser Pro Lys Met Val Gln Gly Ser Gly Cys Phe Gly Arg Lys Met Asp
1               5                   10                  15

Arg Ile Ser Ser Ser Ser Gly Leu Gly Cys Lys Val Leu Arg Arg His
            20                  25                  30
```

<210> SEQ ID NO 8
<211> LENGTH: 27
<212> TYPE: PRT
<213> ORGANISM: Artificial Sequence
<220> FEATURE:
<223> OTHER INFORMATION: Synthetic

<400> SEQUENCE: 8

```
Lys Met Val Gln Gly Ser Gly Cys Phe Gly Arg Lys Met Asp Arg Ile
1               5                   10                  15

Ser Ser Ser Ser Gly Leu Gly Cys Lys Val Leu
            20                  25
```

<210> SEQ ID NO 9
<211> LENGTH: 25
<212> TYPE: PRT
<213> ORGANISM: Artificial Sequence
<220> FEATURE:
<223> OTHER INFORMATION: Synthetic

<400> SEQUENCE: 9

```
Met Ser Ser Phe Ser Thr Thr Thr Val Ser Phe Leu Leu Leu Leu Ala
1               5                   10                  15

Phe Gln Leu Leu Gly Gln Thr Arg Ala
            20                  25
```

<210> SEQ ID NO 10
<211> LENGTH: 38
<212> TYPE: PRT

```
<213> ORGANISM: Artificial Sequence
<220> FEATURE:
<223> OTHER INFORMATION: Synthetic Construct

<400> SEQUENCE: 10

Pro Glu Val Pro Pro Trp Thr Gly Glu Val Ser Pro Ala Gln Arg Asp
1               5                   10                  15

Gly Gly Ala Leu Gly Arg Gly Pro Trp Asp Ser Ser Asp Arg Ser Ala
            20                  25                  30

Leu Leu Lys Ser Lys Leu
        35

<210> SEQ ID NO 11
<211> LENGTH: 28
<212> TYPE: PRT
<213> ORGANISM: Artificial Sequence
<220> FEATURE:
<223> OTHER INFORMATION: ANP

<400> SEQUENCE: 11

Ser Leu Arg Arg Ser Ser Cys Phe Gly Gly Arg Met Asp Arg Ile Gly
1               5                   10                  15

Ala Gln Ser Gly Leu Gly Cys Asn Ser Phe Arg Tyr
            20                  25

<210> SEQ ID NO 12
<211> LENGTH: 22
<212> TYPE: PRT
<213> ORGANISM: Artificial Sequence
<220> FEATURE:
<223> OTHER INFORMATION: CNP

<400> SEQUENCE: 12

Gly Leu Ser Lys Gly Cys Phe Gly Leu Lys Leu Asp Arg Ile Gly Ser
1               5                   10                  15

Met Ser Gly Leu Gly Cys
            20
```